US009149463B2

(12) United States Patent
Einav et al.

(10) Patent No.: US 9,149,463 B2
(45) Date of Patent: Oct. 6, 2015

(54) **METHODS AND COMPOSITIONS OF TREATING A *FLAVIVIRIDAE* FAMILY VIRAL INFECTION**

(75) Inventors: Shirit Einav, Stanford, CA (US);
Jeffrey S. Glenn, Palo Alto, CA (US);
Wenjin Yang, Foster City, CA (US);
Hadas Dvory-Sobol, Mountain View, CA (US); Ingrid C. Choong, Palo Alto, CA (US); Robert McDowell, San Francisco, CA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 808 days.

(21) Appl. No.: 12/383,071

(22) Filed: Mar. 18, 2009

(65) Prior Publication Data

US 2010/0015093 A1 Jan. 21, 2010

Related U.S. Application Data

(63) Continuation-in-part of application No. PCT/US2008/076806, filed on Sep. 18, 2008.

(60) Provisional application No. 61/092,537, filed on Aug. 28, 2008, provisional application No. 60/973,309, filed on Sep. 18, 2007, provisional application No. 61/088,759, filed on Aug. 14, 2008.

(51) Int. Cl.
| | |
|---|---|
| *A61K 31/535* | (2006.01) |
| *A61K 31/416* | (2006.01) |
| *A61K 31/4439* | (2006.01) |
| *A61K 31/454* | (2006.01) |
| *A61K 31/7056* | (2006.01) |
| *A61K 38/21* | (2006.01) |
| *A61K 45/06* | (2006.01) |
| *C07D 231/56* | (2006.01) |
| *C07D 401/06* | (2006.01) |
| *C07D 401/12* | (2006.01) |
| *C07K 14/005* | (2006.01) |

(52) U.S. Cl.
CPC ........... *A61K 31/416* (2013.01); *A61K 31/4439* (2013.01); *A61K 31/454* (2013.01); *A61K 31/7056* (2013.01); *A61K 38/212* (2013.01); *A61K 45/06* (2013.01); *C07D 231/56* (2013.01); *C07D 401/06* (2013.01); *C07D 401/12* (2013.01); *C07K 14/005* (2013.01); *C12N 2770/24122* (2013.01); *C12N 2770/24222* (2013.01); *G01N 2333/186* (2013.01); *G01N 2500/02* (2013.01)

(58) Field of Classification Search
USPC ............. 548/361.1; 544/111; 514/231.5, 403, 514/231
See application file for complete search history.

(56) References Cited

U.S. PATENT DOCUMENTS

| | | | |
|---|---|---|---|
| 2,684,327 A * | 7/1954 | Passal | ........................... 205/277 |
| 2,689,853 A | 9/1954 | Schenck et al. | |
| 3,265,691 A | 8/1966 | Helmer Richter et al. | |
| 3,428,634 A | 2/1969 | Palazzo | |
| 4,011,322 A | 3/1977 | Rahtz et al. | |
| 4,269,835 A | 5/1981 | Whittle | |
| 5,552,426 A | 9/1996 | Lunn et al. | |
| 6,166,023 A * | 12/2000 | Schindler et al. | ........... 514/234.5 |
| 6,211,177 B1 | 4/2001 | Sperl et al. | |
| 6,369,235 B1 | 4/2002 | Michejda et al. | |
| 6,476,062 B2 | 11/2002 | Chu | |
| 7,495,015 B2 | 2/2009 | Arora et al. | |
| 2002/0128307 A1 | 9/2002 | Chu | |
| 2004/0092575 A1 | 5/2004 | Peuvot et al. | |
| 2004/0097438 A1 | 5/2004 | Hashimoto et al. | |
| 2004/0224876 A1 | 11/2004 | Jost-Price et al. | |
| 2005/0187261 A1 * | 8/2005 | Verner et al. | ................... 514/350 |
| 2005/0192261 A1 | 9/2005 | Jost-Price et al. | |
| 2006/0052602 A1 | 3/2006 | Kim et al. | |
| 2008/0161324 A1 | 7/2008 | Johansen et al. | |
| 2010/0028299 A1 | 2/2010 | Einav et al. | |

FOREIGN PATENT DOCUMENTS

| | | |
|---|---|---|
| DE | 102007028521 A1 | 12/2008 |
| EP | 1400241 A1 | 3/2004 |
| KR | 10-1995-0031074 A | 12/1995 |
| WO | 0204425 A2 | 1/2002 |
| WO | 0207761 A1 | 3/2002 |
| WO | 03060475 A2 | 7/2003 |
| WO | 2005012288 A1 | 2/2005 |
| WO | WO 2005/032329 | 4/2005 |
| WO | 2006010446 A2 | 2/2006 |
| WO | 2006131737 | 12/2006 |

(Continued)

OTHER PUBLICATIONS

Testa; "Prodrug research: futile or fertile?"; 2004; Biochemical Pharmacology; 68: 2097-2106.*
International Search Report and Written Opinion dated Apr. 1, 2009.
Blight, K.J., er al., "Allelic Variation in the Hepatitis C Virus NS4B Protein Dramatically Influences RNA Replication," J. Virology, Jun. 2007, vol. 81, No. 11, pp. 5724-5736.
Einav, S., et al., "A Nucleotide Binding Motif in Hepatitis C Virus (HCV) NS4B Mediates HCV RNA Replication,"J. Virology, Oct. 2004, vol. 78, No. 20, pp. 11288-11295.
Puerstinger, G., et al., "Antiviral 2,5-disubstituted Imidazo[4,5-c]pyridines: From Anti-Pestivirus to Anti-Hepatitis C Virus Activity," Bioorganic * Medicinal Chemistry Letters, Jan. 2007, vol. 17, No. 2, pp. 390-393.

(Continued)

*Primary Examiner* — Rei-tsang Shiao
(74) *Attorney, Agent, or Firm* — Thomas|Horstemeyer, LLP

(57) ABSTRACT

Briefly described, embodiments of this disclosure include compounds (e.g., such as Formula II, Formula II-a, and specific compounds shown in Table 1), pharmaceutical compositions, methods of treating a host infected with a virus from the Flaviviridae family of viruses, methods of inhibiting HCV replication in a host, methods of inhibiting the binding of NS4B polypeptide to the 3'UTR of HCV negative strand RNA in a host, methods of treating liver fibrosis in a host, and the like.

17 Claims, No Drawings

(56) References Cited

FOREIGN PATENT DOCUMENTS

| WO | 2006131737 A2 | 12/2006 |
|---|---|---|
| WO | 2006135383 A2 | 12/2006 |
| WO | WO 2006/131737 A2 | 12/2006 |
| WO | 2007103111 A2 | 9/2007 |
| WO | 2007115077 A2 | 10/2007 |
| WO | 2007117465 A2 | 10/2007 |
| WO | PCT/US2007/019932 | 3/2008 |
| WO | 2009039248 A2 | 3/2009 |

OTHER PUBLICATIONS

Hirashima, S., et al. "Benzimidazole Derivatives Bearing Substituted Biphenyls as Hepatitis C Virus NS5B RNA-Dependent RNA Polymerase Inhibitors: Structure-Activity Relationship Studies and Identification of a Potent and Highly Selective Inhibitor JTK-109," J. Medicinal Chemistry, Jun. 2006, vol. 49, No. 15, pp. 4721-4736.

Korba, B.E., et al. "Nitazoxanide, Tizoaxanide and Other Thiazolides are Potent Inhibitors of Hepatitis B Virus and Hepatitis C Virus Replication," Antiviral Research, Sep. 4, 2007, vol. 77, No. 1, pp. 56-63.

Blight, et al.; Efficient Initiation of HCV RNA Replication in Cell Culture; Science; vol. 290; Dec. 8, 2009, 19721974.

Einav, et al.; A Nucleotide Binding Motif in Hepatitis C Virus (HCV) NS4B Mediates HCV RNA Replication; Journal of Virology; Oct. 2004; vol. 78, No. 20; pp. 1128-11295.

Hwang, et al.; Inhibition of Hepatitis C Virus Replication by Arsenic Trioxide; Antimicrobial Agents and Chemotheraphy; vol. 48, No. 8; Aug. 2004; p. 2876-2882.

Lohmann, et al.; Replication of Subgenomic Hepatitis C Virus RNAs in a Hepatoma Cell Line; Science; vol. 285; Jul. 2, 1999; pp. 110-113.

Maerkl, et al.; A Systems Approach to Measuing the Binding Energy Landscapes of Transcription Factors; Science; vol. 315; Jan. 12, 2007; pp. 233-237.

Takhampunya, et al.; Inhibition of Dengue Virus Replication by Mycophenolic Acid and Ribavirin; Journal of General Virology; Voi. 87; 2006; 1947-1952.

International Search Report and Written Opinion dated Aug. 13, 2009.

The International Search Report and Written Opinion dated Dec. 24, 2010.

The International Search Report and Written Opinion dated Dec. 27, 2010.

Selwood, D.L., et al., "Synthesis and Biological Evaluation of Novel Pyrazoles and Indazoles as Activators of the Nitric Oxide Receptor, Soluable Guanylate Cyclase," Journal of Medicinal Chemistry, 2001, vol. 44, pp. 78-93.

Patel, P.D., et al., "3D QSAR and Molecular Docking Studies of Benzimidazole Derivatives as Hepatitis C Virus NS5B Polymerase Inhibitors." Journal of Chemical Information and Modeling, 2008, vol. 48, pp. 42-55.

Beaulieu, C., et al., "Benzimidazoles as New Potent and Selective DP Antagonists for the Treatment of Allergic Rhinitis," Bioorganic & Medicinal Chemistry Letters, 2004, vol. 14, pp. 3195-3199.

Einav, S., et al., "Discovery of a Hepatitis C Target and its Pharmacological Inhibitors by Microfluidic Affiinity Analysis," Nature Biotechnology, Sep. 2008, vol. 26, No. 9, pp. 1019-1027.

Einav, S., et al., "The Hepatitis C Virus (HCV) NS$B RNA Binding Inhibitor Clemizole is Highly Synergistic with HCV Protease Inhibitors," Anti-HCV Drug Synergy with Clemizole, JID 2010:202 (Jul. 1) pp. 65-74, 2010.

Cho, et al., "Identification of a Class of HCV Inhibitors Directed Against the Nonstructural Protein NS4B," www.scienceTranslationalMedicine.org, Jan. 20, 2010, vol. 2, Issue 15, pp. 1-8.

Cho, et al., Supplementary Materials for "Identification of a Class of HCV Inhibitors Directed Against the Nonstructural Protein NS4B," www.scienceTranslationalMedicine.org, Jan. 20, 2010, vol. 2, Issue 15, pp. 1-23.

The Supplemental European Search Report dated Jul. 2, 2012.

The Supplemental European Search Report dated Aug. 8, 2012.

Einav, et al., Discovery of a Hepatitis C Target and its Pharmacological Inhibitors by Microfluidic Affinity Analysis, Nature Biotechnology, Nature Publishing Group, New York, NY, vol. 26, No. 9, Sep. 1, 2008, pp. 1019-1027.

Caroti, et al., "Synthesis, Antilipidemic and Platelet Antiaggregatory Activity of 2-Aminobenzimidazole Amide Derivatives," II Farmaco, Elsevier France, Scientifiques Et Medicals, IT, vol. 44, No. 3, Jan. 1, 1989, pp. 227-255.

Tuncbilek, et al., "Synthesis and Antimicrobial Activity of Some New Anilino Benzimidazoles," Archiv Der Pharmazie, Wiley, VH Verlag GmBH & Co. KGAA, Dec. 1, 1997, pp. 372-376.

Manganaro, et al., "Activity of Antiinflammatory Steroidal and Nonsteroidal Compounds in Some Experimental Functions, II, Activity of Certain Nonsteroidal Antiinflammatory Agents as Compared with that of Prednisone in Murine Hepatitis Due to MHV3," Inflammation, Plenum Press, New York, NY, vol. Proc. Int. Symp. No. 1968, Jan. 1, 1968, pp. 67-71.

Anonymous, Registry, Dec. 8, 2008, XP007920913.

Anonymous, Registry, Dec. 18, 1984-Dec. 22, 2009, XP007920912.

Anonymous, Registry, Nov. 8, 2004, XP007920909.

Supplemental European Search Report dated Oct. 13, 2011.

Beaulieu, P.L., et al., "Non-nucleoside Inhibitors of the Hepatitis C Virus NS5B polymerase: Discovery and Preliminary SAR of Benzimidazolde Derivatives," Bioorganic & Medicinal Chemistry Letters, Pergamon, Elsevier Science, GB, vol. 14, No. 1, Jan. 1, 2004, pp. 119-124.

Beaulieu, P.L., et al., "Improved Replicon Cellular Activity of Non-Nucleoside Allosteric Inhibitors of HCV NS5B Polymerase: From Benzimidazole to Indole Scaffolds," Bioorganic & Medicinal Chemistry Letters, Pergamon, Elsevier Science, GB, vol. 16, No. 19, Oct. 1, 2006, pp. 4987-4993.

"Martindale, The Complete Drug Reference", 2000, Pharmaceutical Press, XP000002659125, Clemizole Hydrocholoride, p. 406.

Einav, Shirit, et al., "Discovery of a Hepatitis C Target and its Pharmacological Inhibitors of Microfluidic Affinity Analysis," Nature Biotechnology, Nature Publishing Group, NY, vol. 26, No. 9, Sep. 1, 2008, pp. 1019-1027.

Office Action dated Sep. 9, 2013 for Chinese Application Serial No. 201080021845.9, 4 pages.

Office Action dated Sep. 11, 2013 for Chinese Application Serial No. 201080021850.X, 3 pages.

Patani et al. Bioisosterism: A Rational Approach in Drug Design. Chem. Rev. 1996. vol. 96, pp. 3147-3176.

Supplementary European Search Report dated Sep. 19, 2011.

Iacobellis et al. "External validation of biochemical indices for noninvasive evaluation of liver fibrosis in HCV chronic Hepatitis". American Journal of Gastroenterology, 2005, vol. 100, pp. 868-873.

Voronina et al. "Synthesis and pharmaceutical properties of amidine analogs of pyracetatam". Khimiko-Farmatsevticheskii Zhurnal, 1990, vol. 24, 11:26-29. CAPLUS Abstract, AN 1991:101601.

Testa, B.; Prodrug Research: Futile or Fertile; Biochemical Pharacology 68 (2004; 2097-2106.

Schilders G. et al. MPP6 is an exosome-associated RNA-binding protein involved in 5.8S rRNA maturation. Nucleic Acids Research, 2005, vol. 33(21), pp. 6795-6804.

Blight KJ et al. Efficient Initiation of HCV RNA Replication in Cell Culture. Science, 2000, vol. 290, pp. 1972-1974.

Tong X et al. Identification and analysis of fitness of resistance mutations against the HCV protease inhibitor SCH 503034. Antiviral Research, 2006, vol. 70, pp. 28-38.

Lindenbach et al. Complete Replication of Hepatitis C Virus in Cell Culture. Science, 2005, vol. 309, pp. 623-626.

Echeverri, A.C. & Dasgupta, A. Amino Terminal Regions of Poliovirus 2C Protein Mediate Membrane Binding. Virology, 1995. vol. 208, pp. 540-553.

Rodriguez, P.L. & Carrasco L Poliovirus Protein 2C Contains Two Regions Involved in Rna Binding Activity. J. Biol. Chem. 1995, vol. 270 (17), pp. 10105-10112.

Hadd, A.D. et al. Microchip Device for Performing Enzyme Assays. Anal. Chem. 1997, vol. 69, pp. 3407-3412.

(56) References Cited

OTHER PUBLICATIONS

El-Hage, N. & Luo, G. Replication of Hepatitis C Virus RNA Occurs in a Membrane-Bound Replication Complex Containing Nonstructural Viral Proteins and RNA. Journal of General Virology, 2003, vol. 84, pp. 2761-2769.

Park-Lee et al. Characterization of the Interaction between Neuronal RNA-binding Protein HuD and Au-rich RNA. Journal of Biological Chemistry, 2003, vol. 278(41) pp. 39801-39808.

Spangberg, K et al. HuR, a Protein Implicated in Oncogene and Growth Factor mRNA Decay, Binds to the 39 Ends of Hepatitis C Virus RNA of Both Polarities. Virology, 2000, vol. 274, pp. 378-390.

Lundin, M et al. Topology of the Membrane-Associated Hepatitis C Virus Protein NS4B. Journal of Virology, 2003, vol. 77(9), pp. 5428-5438.

Gosert, R. et al. Identification of the Hepatitis C Virus RNA Replication Complex in Huh-7 Cells Harboring Subgenomic Replicons. Journal of Virology, 2003, vol. 77(9), pp. 5487-5492.

Tscherne, D.M. Time- and Temperature-Dependent Activation of Hepatitis C Virus for Low-pH-Triggered Entry. Journal of Virology, 2006, vol. 80(4), pp. 1734-1741.

Elazar, M. et al. An N-Terminal Amphipathic Helix in Hepatitis C Virus (HCV) NS4B Mediates Membrane Association, Correct Localization of Replication Complex Proteins, and HCV RNA Replication. Journal of Virology, 2004, vol. 78(20), pp. 11393-11400.

Dimitrova M. et al. Protein-Protein Interactions between Hepatitis C Virus Nonstructural Proteins. Journal of Virology, 2003, vol. 77(9), pp. 5401-5414.

Glenn J.S. et al. In Vitro-Synthesized Hepatitis Delta Virus RNA Initiates Genome Replication in Cultured Cells. Journal of Virology, 1990, vol. 64(6), pp. 3104-3107.

Huang L. et al. Hepatitis C Virus Nonstructural Protein 5A (NS5A) Is an RNA-binding Protein. Journal of Biological Chemistry, 2005, vol. 280(43) pp. 36414-36428.

Elazar, M. et al. Amphipathic Helix-Dependent Localization of NS5A Mediates Hepatitis C Virus RNA Replication. Journal of Virology, 2003, vol. 77(70), pp. 6055-6061.

Egger D. et al. Expression of Hepatitis C Virus Proteins Induces Distinct Membrane Alterations Including a Candidate Viral Replication Complex. Journal of Virology, 2002, vol. 76(12), pp. 5974-5984.

Kang L. et al. Microfluidics for drug discovery and development: From target selection to product lifecycle management. Drug Discovery Today, 2008, vol. 13 (1/2), pp. 1-13.

Kusov YY. et al. Membrane association and RNA binding of recombinant hepatitis a virus protein 2C. Arch Virol. 1998, vol. 143, pp. 931-944.

Liang, T.J. et al. Pathogenesis, Natural History, Treatment, and Prevention of Hepatitis C, Ann. Intern. Med., 2000, vol. 132, pp. 296-305.

Park, S. et al. HuD RNA Recognition Motifs Play Distinct Roles in the Formation of a Stable Complex with AU-Rich RNA. Mol. Cell. Biol. 2000, vol. 20(13), pp. 4765-4772.

Lee, N. L. et al. Solvent Compatibility of Poly(dimethylsiloxane)-Based Microfluidic Devices. Anal. Chem., 2003, vol. 75, pp. 6544-6554.

Roosild, T.P. et al. NMR Structure of Mistic, a Membrane-Integrating Protein for Membrane Protein Expression. Science, 2005, vol. 307, pp. 1317.

Reed K.E. & Rice C.M. Overview of Hepatitis C Virus Genome Structure, Polyprotein Processing, and Protein Properties. The Hepatitis C Viruses, Current Topics in Microbiology and Immunology, 2000, vol. 242, pp. 55-84.

Overington, J.P. et al. How many drug targets are there? Nat Rev Drug Discov. 2006, vol. 5, pp. 993-996.

Wung, CH et al. Identification of the RNA-binding sites of the triple gene block protein 1 of bamboo mosaic potexvirus. J. Gen. Virol. 1999, vol. 80, pp. 1119-1126.

Toepke, MW, et al. PDMS absorption of small molecules and consequences in microfluidic applications. Lab on a Chip, 2006, vol. 6, pp. 1484-1483.

Whitesides, GM. The origins and the future of microfluidics. Nature 2006, vol. 442, pp. 368-373.

Myer, VE et al. Identification of HuR as a protein implicated in AUUUA-mediated mRNA decay. The EMBO Journal, 1997, vol. 16, pp. 2130-2139.

Burd, CG & Dreyfuss G. Conserved Structures and Diversity of Functions of RNA-Binding Proteins. Science, 1994, vol. 265, pp. 615-621.

Glenn, JS et al. Identification of a Prenylation Site in Delta Virus Large Antigen. Science, 1992, vol. 256, pp. 1331-3.

Gupta AK et al. Antifungal Agents: A overview. Part I. Journal of the American Academy of Dermatology, 1994, vol. 30(5) Part 1, pp. 677-698.

* cited by examiner

SEQUENCE LISTING

```
<160> NUMBER OF SEQ ID NOS: 5

<210> SEQ ID NO 1
<211> LENGTH: 341
<212> TYPE: RNA
<213> ORGANISM: Hepatitis C virus

<400> SEQUENCE: 1
cggucggggg acuaccccg cugugaggug guacuuagug aggggacacu ccuugaugac      60
agaagugcgu cuuucgcaga ucgguaccgc aaucauacuc acagcacguc ggagguccug    120
```

```
ggggggaggg cccucucggu auccagac gccuuggcca cucaugugc cuuaacgguc    180 cugcuggccc aggaaagaac cuauuugggc gaguuacgga ccucuaaacc cgcacggggg    240
cguucugacg aucggcucau cacaacccag cgcuuccgg aacaccauga cggacuaucc    300
cacgaacgcu cacggggccc uccagagcau cuggcacgug g                        341
```

```
<210> SEQ ID NO 2
<211> LENGTH: 261
<212> TYPE: PRT
<213> ORGANISM: Artificial Sequence
<220> FEATURE:
<223> OTHER INFORMATION: Membrane protein sequence

<400> SEQUENCE: 2

Ala Ser His Leu Pro Tyr Ile Glu Gln Gly Met Met Leu Ala Glu Gln
1               5                   10                  15

Phe Lys Gln Lys Ala Leu Gly Leu Leu Gln Thr Ala Ser Arg His Ala
            20                  25                  30

Glu Val Ile Thr Pro Ala Val Gln Thr Asn Trp Gln Lys Leu Glu Val
        35                  40                  45

Phe Trp Ala Lys His Met Trp Asn Phe Ile Ser Gly Ile Gln Tyr Leu
    50                  55                  60

Ala Gly Leu Ser Thr Leu Pro Gly Asn Pro Ala Ile Ala Ser Leu Met
65                  70                  75                  80

Ala Phe Thr Ala Ala Val Thr Ser Pro Leu Thr Thr Gly Gln Thr Leu
                85                  90                  95

Leu Phe Asn Ile Leu Gly Gly Trp Val Ala Ala Gln Leu Ala Ala Pro
            100                 105                 110

Gly Ala Ala Thr Ala Phe Val Gly Ala Gly Leu Ala Gly Ala Ala Ile
        115                 120                 125

Gly Ser Val Gly Leu Gly Lys Val Leu Val Asp Ile Leu Ala Gly Tyr
    130                 135                 140

Gly Ala Gly Val Ala Gly Ala Leu Val Ala Phe Lys Ile Met Ser Gly
145                 150                 155                 160

Glu Val Pro Ser Thr Glu Asp Leu Val Asn Leu Leu Pro Ala Ile Leu
                165                 170                 175

Ser Pro Gly Ala Leu Val Val Gly Val Val Ser Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Ala Ile Leu Ser Ser Leu
225                 230                 235                 240

Thr Val Thr Gln Leu Leu Arg Arg Leu His Gln Trp Ile Ser Ser Glu
                245                 250                 255

Cys Thr Thr Pro Cys
            260

<210> SEQ ID NO 3
<211> LENGTH: 16
<212> TYPE: PRT
<213> ORGANISM: Artificial Sequence
<220> FEATURE:
<223> OTHER INFORMATION: Chemically synthesized primer sequence

<400> SEQUENCE: 3
```

```
Ala Gly Ala Gly Cys Cys Ala Thr Ala Gly Thr Gly Gly Thr Cys Thr
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: Chemically synthesized primer sequence

<400> SEQUENCE: 4

Cys Cys Ala Ala Ala Thr Cys Thr Cys Cys Ala Gly Gly Cys Ala Thr
1               5                   10                  15

Thr Gly Ala Gly Cys
            20

<210> SEQ ID NO 5
<211> LENGTH: 24
<212> TYPE: PRT
<213> ORGANISM: Artificial Sequence
<220> FEATURE:
<223> OTHER INFORMATION: Chemically synthesized primer sequence

<400> SEQUENCE: 5

Cys Ala Cys Cys Gly Gly Ala Ala Thr Thr Gly Cys Cys Ala Gly Gly
1               5                   10                  15

Ala Cys Gly Ala Cys Cys Gly Gly
            20
```

METHODS AND COMPOSITIONS OF TREATING A *FLAVIVIRIDAE* FAMILY VIRAL INFECTION

CROSS-REFERENCE TO RELATED APPLICATION

This application is a continuation in-part application of PCT patent applications US/2008/076804 (entitled "Methods of Treating a Flaviviridae Family Viral Infection, Compositions For Treating A Flaviviridae Family Viral Infection, and Screening Assays for Identifying Compositions For Treating A Flaviviridae Family Viral Infection") and US/2008/076806 (entitled "Methods of Treating A Flaviviridae Family Viral Infection and Compositions For Treating A Flaviviridae Family Viral Infection"), both filed Sep. 18, 2008, which in turn claim priority to U.S. provisional application having Ser. No. 60/973,309 (entitled "Methods for Treating Hepatitis C Virus Infection"), filed on Sep. 18, 2007, U.S. provisional application having Ser. No. 61/088,759 (entitled "Methods and Compositions for Treating Hepatitis C Virus Infection"), filed on Aug. 14, 2008, as well as U.S. provisional application having Ser. No. 61/092,537 (entitled "Methods of Treating a Flaviviridae family viral Infection, Compositions for treating a Flaviviridae family viral Infection, and screening assays for identifying compositions for treating a Flaviviridae family viral Infection") filed on Aug. 28, 2008; all of the foregoing PCT and U.S. provisional applications are entirely incorporated herein by reference.

This application is related to U.S. patent application entitled "Methods and compositions of Treating a Flaviviridae family viral Infection" filed on Mar. 18, 2009, to Einav et al., (Express Mail number EM129179657) which is incorporated herein by reference.

STATEMENT REGARDING FEDERALLY SPONSORED RESEARCH OR DEVELOPMENT

This invention was made with Government support under contract DK066793 awarded by the National Institutes of Health. The Government has certain rights in this invention.

BACKGROUND

Over 150 million people are infected with Hepatitis C Virus (HCV) worldwide. Unfortunately, the current standard care, consisting of administration of a combination of interferon and ribavirin, is often unable to clear HCV infection in many infected individuals. Moreover, this treatment is associated with significant side effects, precluding its use by many individuals. Thus, current therapies are inadequate for the majority of the patients, and there is a pressing need for new drugs to treat HCV infection (See, *Annals Internal Med.* 132:296-305 (2000)).

The 9.6-kb positive single-stranded RNA HCV genome encodes a 3,000-amino-acid polyprotein that is proteolytically processed into structural proteins, which are components of the mature virus, and nonstructural proteins (NS), which are involved in replicating the viral genome (*Curr Top Microbiol Immunol* 242, 55-84 (2000)). Like other positive strand RNA viruses (B. N. Fields, D. M. Knipe, and P. M. Howley (ed.), *Fields Virology*. (Lippincott-Raven Publications, Philadelphia, Pa., 1996, in "The viruses and their replication")), HCV appears to replicate in association with intracellular membrane structures. In the case of HCV, the structures are referred to as the membranous web (*J Virol* 76, 5974-5984 (2002)), the formation of which is believed to be induced by the NS4B protein. NS4B is also used to assemble the other viral NS proteins within the apparent sites of RNA replication (*J Virol* 78, 11393-11400 (2004)). It is not known how viral RNA, especially the negative strand template used for production of progeny genomes, might be incorporated or maintained at these replication sites.

There is an ongoing need in the art for agents that treat HCV infection; and for methods of identifying candidate agents that are suitable for treating HCV infection.

SUMMARY

Briefly described, embodiments of this disclosure include compounds, compositions, pharmaceutical compositions, methods of treating a host infected with a virus from the Flaviviridae family of viruses, methods of treating HCV replication in a host, methods of inhibiting the binding of NS4B polypeptide to the 3'UTR of HCV negative strand RNA in a host, methods of treating liver fibrosis in a host, and the like.

In one embodiment, the present invention provides a method of treating a subject infected with a virus from the Flaviviridae family. The method typically comprises administering to the subject an isostere of a benzimidazole core structure, or a pharmaceutically acceptable salt, an isomer, a tautomer or a prodrug thereof, in an amount that is effective in reducing viral load of said virus in said subject. The virus of the Flaviviridae family can include a flavivirus; a pestivirus; a Hepatitis C virus; a yellow fever virus; a Dengue virus: a Japanese Encephalitis virus; a Murray Valley Encephalitis virus; a St. Louis Encephalitis virus; a West Nile virus; a tick-borne encephalitis virus; a Kunjin virus; a Central European encephalitis virus; a Russian spring-summer encephalitis virus; a Powassan virus; a Kyasanur Forest disease virus; a Omsk hemorrhagic fever virus; and their respective genotypes and subgenotypes.

In another embodiment, the present invention provides a method of inhibiting formation of a complex between NS4B polypeptide and hepatitis C viral (HCV) RNA in a cell. The method comprises administering to the cell an isostere of a benzimidazole core structure, or a pharmaceutically acceptable salt, an isomer, a tautomer or a prodrug thereof, in an amount that is effective in reducing binding of NS4B polypeptide to HCV RNA.

In yet another embodiment, the present invention provides a method of treating liver fibrosis in a subject. The method comprises administering to the subject a therapeutically effective amount of an isostere of a benzimidazole core structure, or a pharmaceutically acceptable salt, an isomer, a tautomer or a prodrug thereof.

In some aspects, any of the methods of the present invention involves administration of an isostere of a benzimidazole core structure having a structure of Formula II:

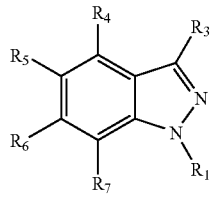

Formula II wherein $R_1$ is selected from the group consisting of: —H,

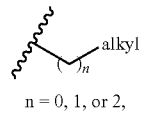

n = 0, 1, or 2, and

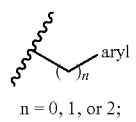

n = 0, 1, or 2;

each of $R_3$, $R_4$, $R_5$, $R_6$, and $R_7$ is independently selected from the group consisting of: —H, —Br, —Cl, —F, —I, —CH$_3$, —CN, —OCH$_3$, —NH$_2$,

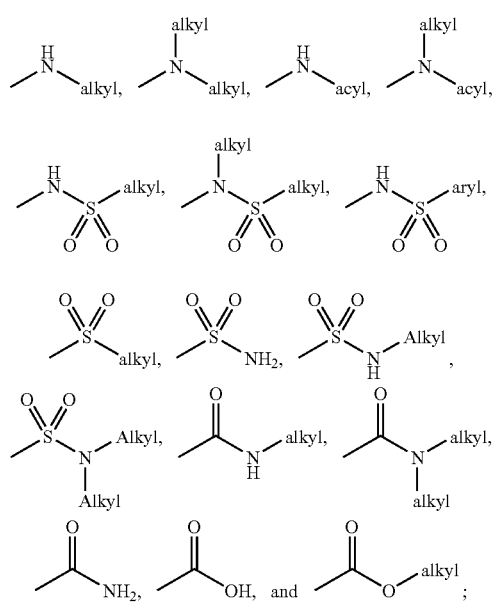

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system. In some embodiments, $R_3$ is H. In other embodiments, $R_1$ is

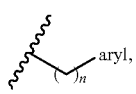

and n is 1.

In yet another aspect, the indazole used in the subject methods is a compound of Formula II-a, or a pharmaceutically acceptable salt or an isomer thereof:

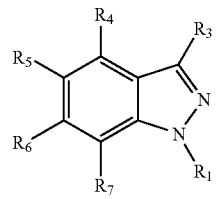

Formula II-a wherein $R_1$ is selected from the group consisting of: —H and

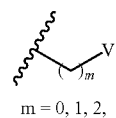

m = 0, 1, 2, wherein V is selected from alkyl, cycloalkyl, heterocyclo, aryl or heteroaryl;

$R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$NH$_2$, —SO$_2$NH(alkyl), NHSO$_2$(alkyl), heteroaryl, N-attached heterocyclo, or C-attached heterocyclo;

each of $R_4$-$R_7$ is independently selected from the group consisting of: —H, —Br, —Cl, —F, —I, —CH$_3$, —CN, —OH, —OCH$_3$, —NO$_2$, —NH$_2$, —OCH$_2$CH$_2$O-alkyl, —NHCO(alkyl), —NHCO(aryl),

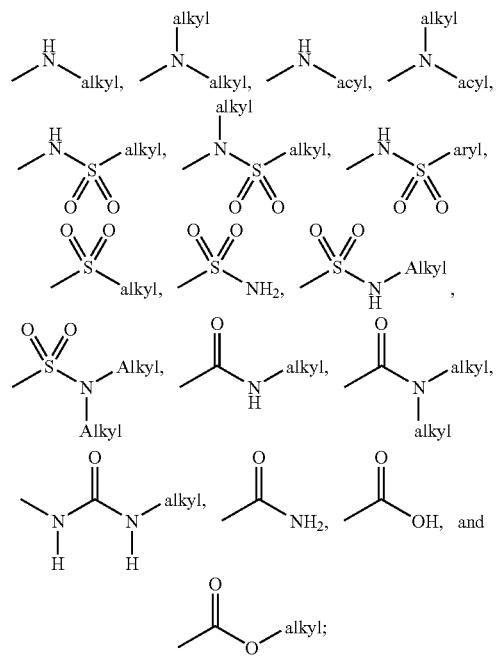

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system. In some embodiments, X is selected from the group consisting of: —OCH$_3$, —OCH$_2$CH$_3$, —OCH$_2$CH$_2$OH, —OCH$_2$CH$_2$OCH$_3$,

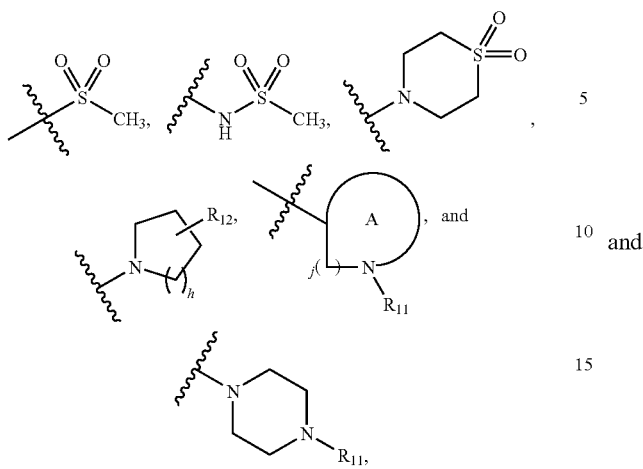

wherein R₁₂ is hydrogen, hydroxy, alkoxy, alkyl, oxo, —(CH₂)ₙ—OH, —C(O)alkyl, —C(O)aryl, or —SO₂alkyl; R₁₁ is hydrogen, —C(O)₂alkyl, —C(O)alkyl, —C(O)aryl, —C(O)NH₂, —C(O)NHalkyl, —C(O)N(alkyl)₂, —SO₂alkyl, —SO₂aryl, —SO₂NH₂, —SO₂NHalkyl, or —SO₂N(alkyl)₂; ring A is a 5-, 6-, or 7-membered ring, j is 0, 1, or 2; and h is 1, 2, or 3. In other embodiments, R₃ is selected from the group consisting of: —O(CH₂)₂NMe₂, —O(CH₂)₂NEt₂, —O(CH₂)₃NMe₂, —O(CH₂)₃NEt₂, and

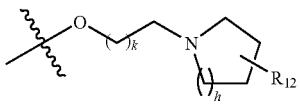

wherein k is 0, 1, or 2, h is 1, 2, or 3, and R₁₂ is hydrogen, hydroxy, alkoxy, alkyl, oxo, —(CH₂)ₙ—OH, —C(O)alkyl, —C(O)aryl, or —SO₂alkyl. Where desired, the indazole compound employed in the subject method can have any of the structures disclosed herein, R₁ is —CH₂V, wherein V is selected from cycloalkyl, heterocyclo, aryl or heteroaryl.

The treatment methods provided herein may further comprise administering one or more additional therapeutic agents selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

The present invention also provides a compound having a structure of Formula II, or a pharmaceutically acceptable salt thereof:

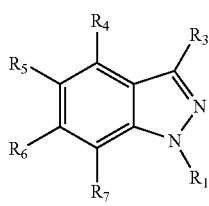

Formula II wherein R₁ is selected from the group consisting of: —H,

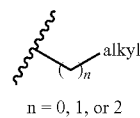

n = 0, 1, or 2 and

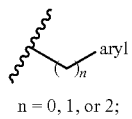

n = 0, 1, or 2;

each of R₃, R₄, R₅, R₆, and R₇ is independently selected from the group consisting of: —H, —Br, —Cl, —F, —I, —CH₃, —CN, —OCH₃, —NH₂, —O-alkyl,

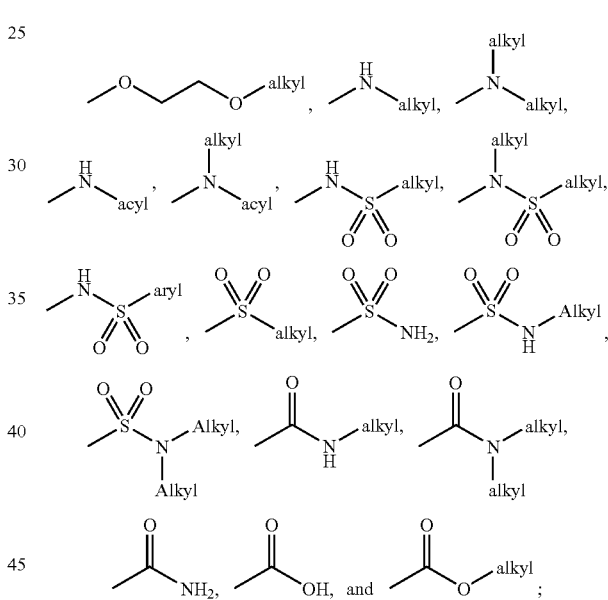

or, optionally, R₄ and R₅, R₅ and R₆, or R₆ and R₇ are joined together with a bond to form a 5, 6, or 7-membered ring; or, optionally, R₄ and R₅, R₅ and R₆, or R₆ and R₇ are joined together to form a 1,2-(methylenedioxy)benzene ring system. In some embodiments, R₃ of the compound is H. In other embodiments, R₁ of the compound is

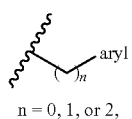

n = 0, 1, or 2, and n is 1.

The present invention further provides a compound of Formula II-a, or a pharmaceutically acceptable salt or an isomer thereof:

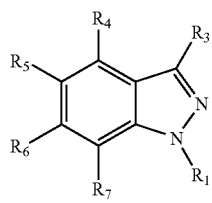

Formula II-a wherein $R_1$ is selected from the group consisting of: —H and

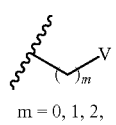

m = 0, 1, 2, wherein V is selected from alkyl, cycloalkyl, heterocyclo, aryl or heteroaryl;

$R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$ NH$_2$, —SO$_2$ NH(alkyl), NHSO$_2$(alkyl), heteroaryl, N-attached heterocyclo, or C-attached heterocyclo;

each of $R_4$-$R_7$ is independently selected from the group consisting of: —H, —Br, —Cl, —F, —I, —CH$_3$, —CN, —OH, —OCH$_3$, —NO$_2$, —NH$_2$, —O-alkyl, —OCH$_2$CH$_2$O-alkyl, —NHCO(alkyl), —NHCO(aryl),

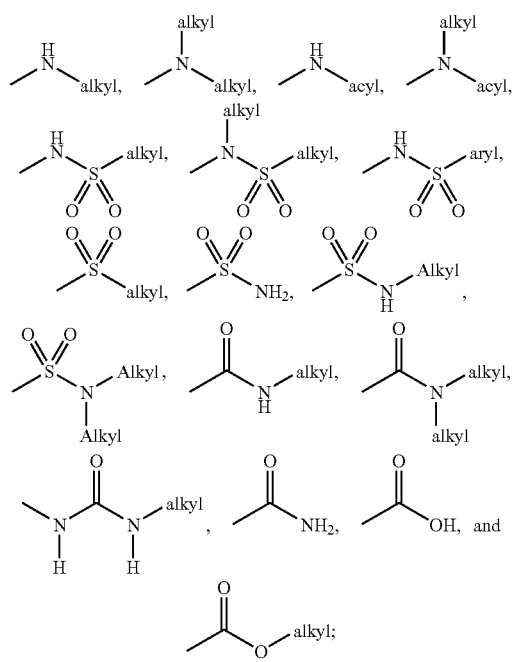

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; provided that the compound of Formula II-a is not

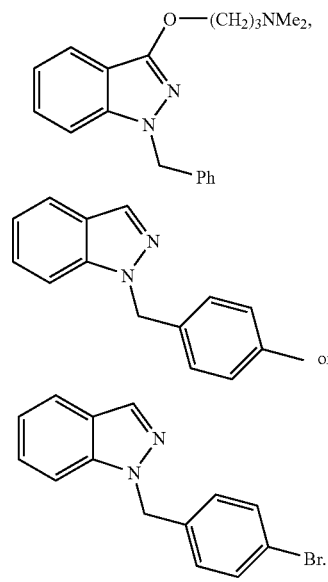

In some embodiments, for the compound of Formula II-a, $R_1$ is

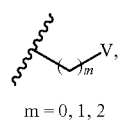

m = 0, 1, 2 and V is aryl. In other embodiments, for the compound of Formula II, $R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, or N-attached heterocyclo. In yet other embodiments, X of Formula II is selected from the group consisting of: —OCH$_3$, —OCH$_2$CH$_3$, —OCH$_2$CH$_2$OH, —OCH$_2$CH$_2$OCH$_3$,

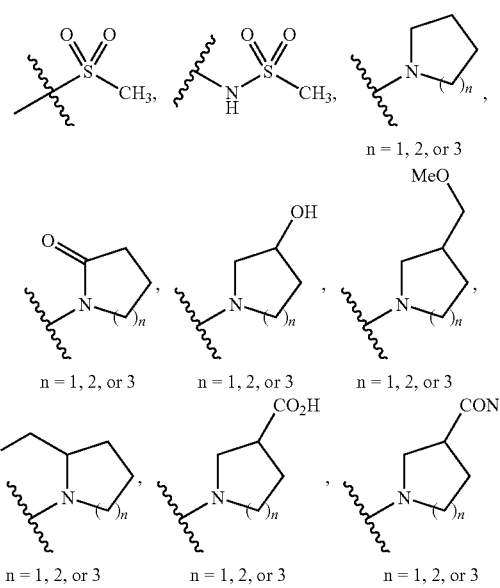

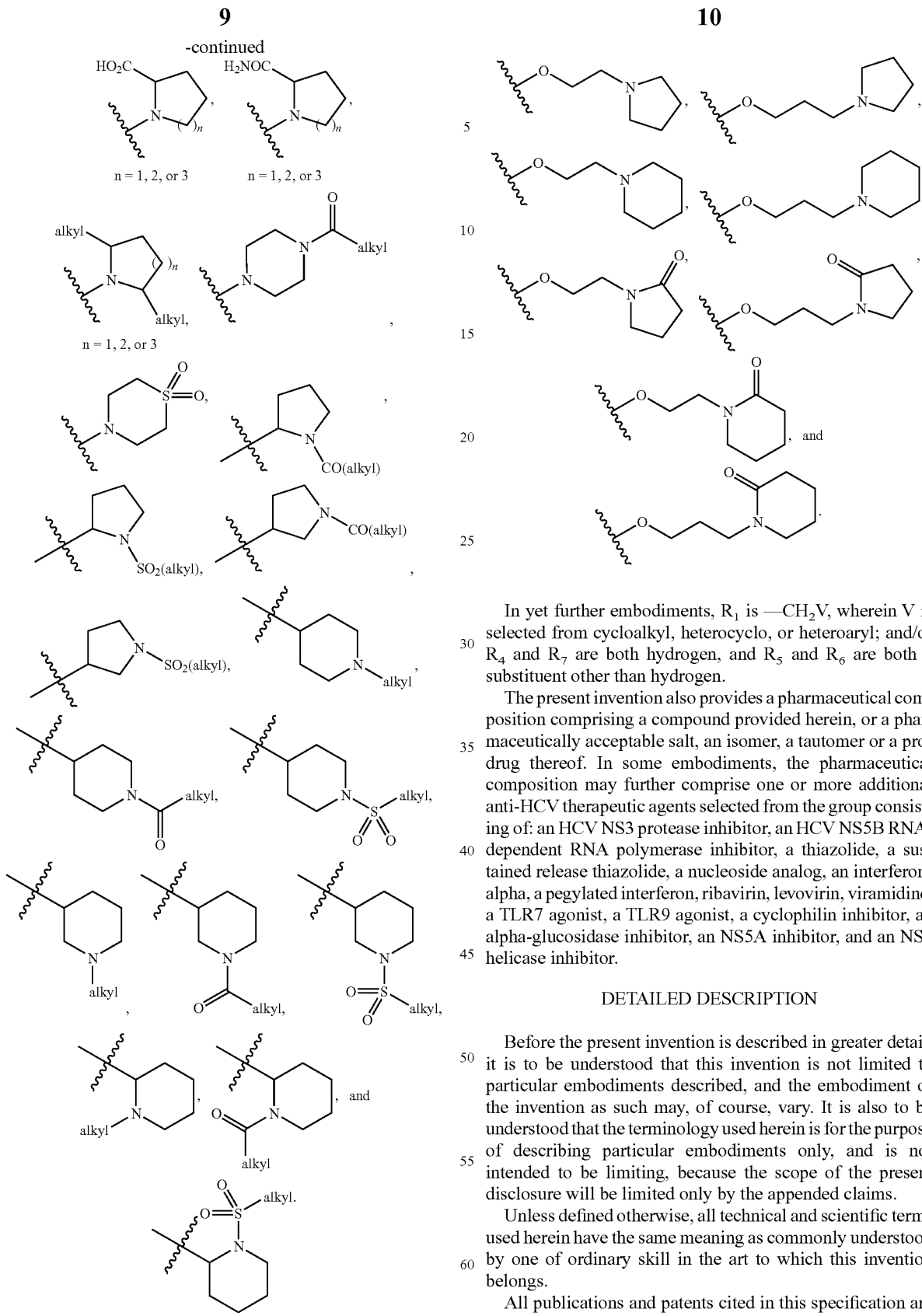

In further embodiments, $R_3$ of a compound of Formula II-a is selected from the group consisting of: $-O(CH_2)_2NMe_2$, $-O(CH_2)_2NEt_2$, $-O(CH_2)_3NEt_2$, In yet further embodiments, $R_1$ is $-CH_2V$, wherein V is selected from cycloalkyl, heterocyclo, or heteroaryl; and/or $R_4$ and $R_7$ are both hydrogen, and $R_5$ and $R_6$ are both a substituent other than hydrogen.

The present invention also provides a pharmaceutical composition comprising a compound provided herein, or a pharmaceutically acceptable salt, an isomer, a tautomer or a prodrug thereof. In some embodiments, the pharmaceutical composition may further comprise one or more additional anti-HCV therapeutic agents selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

DETAILED DESCRIPTION

Before the present invention is described in greater detail, it is to be understood that this invention is not limited to particular embodiments described, and the embodiment of the invention as such may, of course, vary. It is also to be understood that the terminology used herein is for the purpose of describing particular embodiments only, and is not intended to be limiting, because the scope of the present disclosure will be limited only by the appended claims.

Unless defined otherwise, all technical and scientific terms used herein have the same meaning as commonly understood by one of ordinary skill in the art to which this invention belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also contemplated that, where multi-step processes are described in the present disclosure that steps can be executed in different sequence where this is logically possible.

As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

A. DEFINITIONS

In describing and claiming the disclosed subject matter, the following terminology will be used in accordance with the definitions set forth below.

By "Flaviviridae virus" is meant any virus of the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, and the like).

As used herein, the terms "prophylactically treat" and "prophylactically treating" refer completely or partially preventing a disease or symptom thereof and/or may be therapeutic in terms of a partial or complete cure for a disease and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The terms "isolated compound" and "purified compound" mean a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound (e.g., an anti-viral compound, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient", "pharmaceutically acceptable diluent", "pharmaceutically acceptable carrier", and "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" and a "pharmaceutical formulation" are meant to encompass a composition suitable for administration to a subject, such as a mammal, especially a human. In general, a "pharmaceutical composition" or "pharmaceutical formulation" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of an agent (which may be referred to as a compound, an inhibitory agent, and/or a drug) being administered that is sufficient to effect the intended application including but not limited to disease treatment. For example, an effective amount of an inhibiting agent will relieve to some extent one or more of the symptoms of the disease, i.e., infection, being treated, and/or that amount that will prevent, to some extent, one or more of the symptoms of the disease, i.e., infection, that the host being treated has or is at risk of developing. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. inhibiting viral replication in a target cell, and inhibiting NS4B binding to viral RNA. The specific dose will vary depending on the particular compounds chosen, the dosing regimen to be followed, whether it is administered in combination with other compounds, timing of administration, the tissue to which it is administered, and the physical delivery system in which it is carried.

"Pharmaceutically acceptable salt" refers to those salts (organic or inorganic) that retain the biological effectiveness and optionally other properties of the free bases. Pharmaceutically acceptable salts can be obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed agents form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, malates (salts formed with malic acid), maleates (formed with maleic acid), ethanesulfonates (formed with ethanesulfonic acid), methanesulfonates (formed with methanesulfonic acid), 2-naphthalenesulfonates, nicotinates, nitrates, oxalates, pectinates, persulfates, 3-phenylpropionates, phosphates (formed with phosphoric acid), picrates, pivalates, propionates, salicylates, succinates, sulfates (such as those formed with sulfuric acid), sulfonates (such as those mentioned herein including those formed with p-toluenesulfonic acid), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Solvates of the agents of the disclosure are also contemplated herein.

To the extent that the disclosed active compounds, and salts thereof, may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed.

Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab, 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The term "aliphatic group" refers to a saturated or unsaturated linear or branched hydrocarbon group and encompasses alkyl, alkenyl, and alkynyl groups, for example.

The term "alk" or "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. An alkyl group is optionally substituted, unless stated otherwise, with one or more groups, selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted) amino, protected amino, amido, lactam, urea, urethane, sulfonyl, and the like.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. An alkenyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkoxy" refers to an alkyl group linked to oxygen thus: R—O—. In this function, R represents the alkyl group. An example is the methoxy group $CH_3O$—.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, and the like. Thus, "alkyl group" includes ethers, esters, haloalkyls, nitroalkyls, carboxyalkyls, hydroxyalkyls, sulfoalkyls, and the like. "Cyano" refers to a —CN substituent.

The terms "halo" and "halogen" refer to the fluoro, chloro, bromo or iodo groups. There can be one or more halogen groups, which can be the same or different. In an embodiment, each halogen can be substituted by one of the other halogens.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" refers to a mono-, bi-, or tricyclic saturated ring that is fully saturated or partially unsaturated. Examples of such a group includes cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like. A cycloalkyl group is optionally substituted, unless stated otherwise, with one or more groups, selected from aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like. The term "(cycloalkyl)alkyl" refers to the above-defined cycloalkyl group substituted by an above defined alkyl group. Examples of such a group include (cyclohexyl)methyl, 3-(cyclopropyl)-n-propyl, 5-(cyclopentyl)hexyl, 6-(adamantyl) hexyl, and the like. A (cycloalkyl)alkyl group is optionally substituted, unless stated otherwise, with one or more groups, selected from alkyl (including substituted alkyl), aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like. The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2,3 or 4-chlorophenyl, 2,6-dichlorophenyl, 2,5-dichlorophenyl, 3,4-dichlorophenyl, 2,3 or 4-bromophenyl, 3,4-dibromophenyl, 3-chloro-4-fluorophenyl, 2,3 or 4-fluorophenyl and the like; a mono or di(hydroxy)phenyl group such as 2,3, or 4-hydroxyphenyl, 2,4-dihydroxyphenyl, the protected-hydroxy derivatives thereof and the like; a nitrophenyl group such as 2,3, or 4-nitrophenyl; a cyanophenyl group, for example, 2,3 or 4-cyanophenyl; a mono- or di(alkyl)phenyl group such as 2,3, or 4-methylphenyl, 2,4-dimethylphenyl, 2,3 or 4-(iso-propyl)phenyl, 2,3, or 4-ethylphenyl, 2,3 or 4-(n-propyl)phenyl and the like; a mono or di(alkoxy)phenyl group, for example, 2,6-dimethoxyphenyl, 2,3 or 4-(isopropoxy)phenyl, 2,3 or 4-(t-butoxy)phenyl, 3-ethoxy-4-methoxyphenyl and the like; 2,3 or 4-trifluoromethylphenyl; a mono- or dicarboxyphenyl or (protected carboxy)phenyl group such as 2,3 or 4-carboxyphenyl or 2,4-di(protected carboxy)phenyl; a mono- or di(hydroxymethyl)phenyl or (protected hydroxymethyl)phenyl such as 2,3 or 4-(protected hydroxymethyl)phenyl or 3,4-di(hydroxymethyl)phenyl; a mono- or di(aminomethyl) phenyl or (protected aminomethyl)phenyl such as 2,3 or 4-(aminomethyl)phenyl or 2,4-(protected aminomethyl)phenyl; or a mono- or di(N-(methylsulfonylamino))phenyl such as 2,3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" refers to one of the above substituted phenyl groups attached to one of the above-described alkyl groups. The (substituted phenyl)alkyl is connected to another moiety, i.e a compound having a clemizole scaffold, through the alkyl portion of the (substituted phenyl) alkyl. Examples of (substituted phenyl)alkyl include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like. Optionally, adjacent substituents, together with the atoms to which they are bonded, form a 3- to 7-member ring.

The term "heteroaryl" refers to optionally substituted five-membered or six-membered rings that have 1 to 4 heteroatoms, such as oxygen, sulfur and/or nitrogen atoms, either alone or in conjunction with, additional nitrogen, sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a benzene, pyridine or a triazole system.

The following ring systems are nonlimiting examples of the heterocyclic (whether substituted or unsubstituted) radicals denoted by the term "heteroaryl": thienyl, furyl, pyrrolyl, imidazolyl, pyrazolyl, oxazolyl, isoxazolyl, thiazolyl, isothiazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b] pyridazinyl and purinyl, as well as benzo-fused derivatives, for example, benzoxazolyl, benzthiazolyl, benzimidazolyl and indolyl.

A heteroaryl group is optionally substituted, unless stated otherwise, with one or more groups, selected from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl (optionally, substituted), cycloalkyl (optionally substituted), (cycloalkyl)alkyl (optionally substituted), phenyl (optionally substituted), phenylalkyl (optionally substituted phenylalkyl). Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group. The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3- to 13-member monocyclic, 7- to 17-member bicyclic, or 10- to 20-member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. An N-attached heterocyclo is a heterocyclo moiety wherein the heterocyclo moiety is attached to a compound, e.g. a compound of Formula I through a nitrogen that forms part of the heterocyclo ring. Non-limiting examples of N-attached heterocyclo include but are not limited to

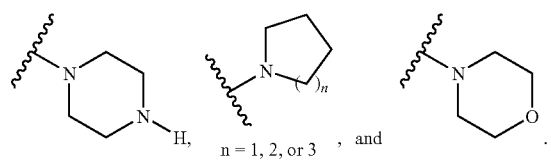

A C-attached heterocyclo is a heterocyclo moiety wherein the heterocyclo moiety is attached to a compound, e.g., a compound of formula II-a, b, or c through a carbon that forms part of the heterocyclo ring. Non-limiting examples include

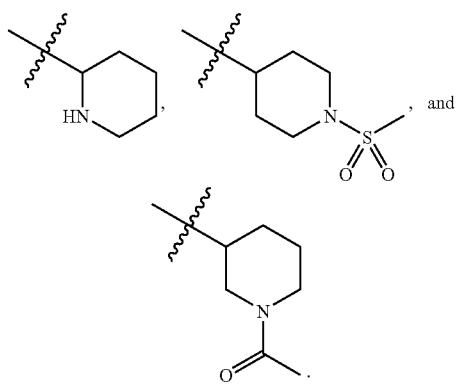

The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

A heterocyclo group is optionally substituted, unless stated otherwise, with one or more groups, selected from alkyl (including substituted alkyl), alkenyl, oxo, aryl (including substituted aryl), heterocyclo (including substituted heterocyclo), carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like where optionally one or more pair of substituents together with the atoms to which they are bonded form a 3- to 7-member ring.

The term "alkanoyl" refers to an alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

The term "(monosubstituted)amino" refers to an amino group with one substituent chosen from the group consisting of phenyl, substituted phenyl, alkyl (including substituted alkyl), $C_1$ to $C_4$ acyl, $C_2$ to $C_7$ alkenyl (including $C_2$ to $C_7$ substituted alkenyl), $C_2$ to $C_7$ alkynyl, $C_7$ to $C_{16}$ alkylaryl (including $C_7$ to $C_{16}$ substituted alkylaryl), and heteroaryl group. The (monosubstituted) amino can additionally have an amino-protecting group as encompassed by the term "protected (monosubstituted)amino." The term "(disubstituted) amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" refers to an alkyl group as defined above, substituted at any position by a heteroaryl group, as above defined.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

"Moiety" refers to a specific segment or functional group of a molecule. Chemical moieties are often recognized chemical entities embedded in or appended to a molecule.

"Nitro" refers to the —NO$_2$ radical.
"Oxa" refers to the —O— radical.
"Oxo" refers to the =O radical.
"Sulfonyl" refers to the groups: —S(O$_2$)—H, —S(O$_2$)-(alkyl), —S(O$_2$)-(cycloalkyl), —S(O$_2$)-(amino), —S(O$_2$)-(aryl), —S(O$_2$)-(heteroaryl), and —S(O$_2$)-(heterocycloalkyl). "Sulfonamidyl" or "sulfonamido" refers to a —S(O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(O)$_2$—NRR radical may be taken together with the nitrogen to which it is attached to form a 4-, 5-, 6-, or 7-membered ring (—S(O$_2$)-(heterocycloalkyl). In some embodiments, it is a C$_1$-C$_{10}$ sulfonamido, wherein each R in sulfonamido contains 1 carbon, 2 carbons, 3 carbons, or 4 carbons total. A sulfonamido group is optionally substituted by one or more of the substituents described herein for alkyl, cycloalkyl, aryl, heteroaryl respectively. A "sulfone" refers to a —S(O$_2$)-(alkyl), —S(O$_2$)-(aryl), —S(O$_2$)-(heteroaryl), or —S(O$_2$)-(heterocycloalkyl) (when the sulfone group is attached to a carbon atom in the heterocycloalkyl). A sulfonamido group is optionally substituted by one or more of the substituents described herein for alkyl, cycloalkyl, aryl, and heteroaryl.

The terms "solvent," "organic solvent," and "inert solvent" each mean a solvent inert under the conditions of the reaction being described. Nonlimiting examples include benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like.

The term "protecting group" refers to chemical moieties that block some or all reactive moieties of a compound and prevent such moieties from participating in certain chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

In an embodiment, the term "ring" can refer to a chemical moiety having a ring structure comprising 3 to 10 carbon atoms in which one or more carbon atoms may be optionally substituted with a heteroatom, such as N, O, or S. A ring may or may not be aromatic and thus may be completely unsaturated, completely saturated, or partially unsaturated; and a ring may refer to a ring within a fused system or an unfused ring. Unless otherwise stated, this definition of "ring" does not modify other definitions of rings provided herein.

B

The present invention provides methods and compositions for treatment (including prophylactic treatment) of infection by a virus that encodes NS4B. Such virus includes any virus of the Flaviviridae family encompassing e.g., flaviviruses, pestiviruses and hepatitis C viruses. Other NS4B encoding viruses include yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Kunjin virus; Central European encephalitis virus; Russian spring-summer encephalitis virus; Powassan virus; Kyasanur Forest disease virus; Omsk hemorrhagic fever virus; and their respective genotypes as well as subgenotypes. The subject methods and compositions are particularly useful for treating or prophylactically treating HCV, including genotype 1, 2, 3, 4, 5, 6, and the like, as well as subtypes of an HCV genotype (e.g., 1a, 1b, 2a, 2b, 3a, and the like).

In one embodiment, the method of treating such viral infection comprises administering to a subject infected with a virus from the Flaviviridae family, an effective amount of an isostere of a benzoimidazole core structure, or a pharmaceutically acceptable salt, an isomer, a tautomer or a prodrug thereof. In one embodiment, the isostere is an indazole.

In one aspect, the subject method is effective in reducing viral load in the infected subject by e.g., at least about 5%, 10%, 15%, 20%, 25%, 30%, 35%, 40%, 45%, 50%, 60%, 70%, 80%, 90%, 95% or even higher as compared to the level of viral load present in the subject prior to such treatment. Without being bound by any particular theory, the reduction in viral load can be effected, in whole or in part, by reducing binding of NS4B polypeptide to the viral genome. In the case of HCV, a decrease in viral load upon administering an isostere of a benzimidazole core structure can be attributable to, in part, a decrease in binding of NS4B polypeptide to HCV negative strand RNA, e.g., at a site on the 3'UTR.

A large number of isosteres of a benzoimidazole core structure, or a pharmaceutically acceptable salt, an isomer, a tautomer or a prodrug thereof can be used in the treatment methods of the present invention. The subject methods can also utilize one or more other isosteres, including but not limited to H1 receptor antagonists that share structural similarity with clemizole and exhibit anti-viral activity. Illustrative H1 receptor antagonists that share structural similarity with clemizole include, but are not limited to, the compounds in the classes known as alcoholamines (e.g., diphenhydramine, carbinoxamine, and clemastine), ethylenediamines (e.g., mepyramine and tripelennamine (clemizole is in this class)), alkylamines (e.g., triprolidine and chlorpheniramine), piperazines (e.g., meclizine and homchlorcyclizine), and phenothiazines (e.g., promethazine).

The subject treatment methods can also employ prodrugs of an isostere of a benzoimidazole core structure thereof. Exemplary prodrugs can be activated by liver enzymes (e.g., cyclic-1,3-propanoyl esters substituted with groups that promote an oxidative cleavage reaction by CYP3A, and the like.). These modifications can render clemizole inactive or less active until it reaches the liver (see, Current Opinion in Investigational Drugs 2006 Vol 7 No 2, 109-117; *J. Med. Chem.* 2008, 51, 2328-2345; and Nucleosides, Nucleotides, and Nucleic Acids, 24 (5-7):375-381, (2005) each of which is incorporated herein by reference for the corresponding discussion).

A typical chemizole scaffold (or a benzimidazole core structure) has the structure shown in Formula I below:

Formula I

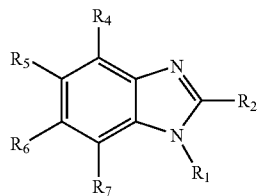

As noted above, the treatment methods of the present invention employ an isostere of a benzimidazole core structure (e.g., indazole compound). In one embodiment, an exemplary indazole compound has the structure of Formula II-a or Formula II-b:

Formula II-a

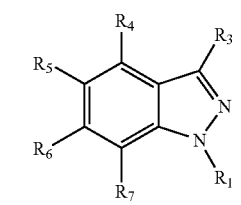

Indazole core

Formula II-b

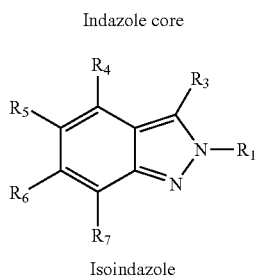

Isoindazole

In one embodiment, for the indazole compounds of Formula II-a or II-b, $R_1$ is —H or

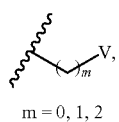

m = 0, 1, 2 wherein V is selected from alkyl, cycloalkyl, heterocyclo, aryl or heteroaryl.

In another embodiment, for the compounds of Formula II-a or II-b, $R_1$ is

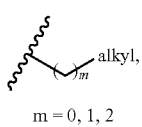

m = 0, 1, 2 wherein the alkyl moiety is unsubstituted or substituted. The alkyl moiety forming part (m=1 or 2) or all (m=0) of $R_1$, is branched or unbranched. The alkyl moiety of $R_1$ includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl.

In yet another embodiment, $R_1$ is

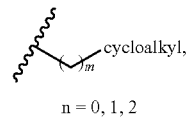

n = 0, 1, 2 wherein the cycloalkyl moiety is unsubstituted or substituted. The cycloalkyl moiety forming part (m=1 or 2) or all (m=0) of $R_1$, includes but is not limited to cyclopropyl, cyclobutyl, cyclopentyl and cyclohexyl. Nonlimiting exemplary $R_1$ include the following formulae:

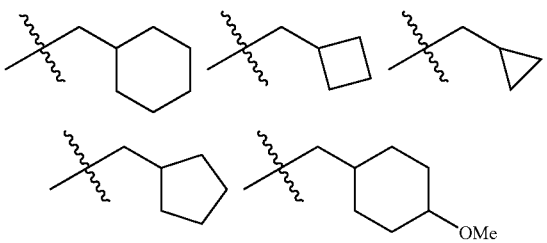

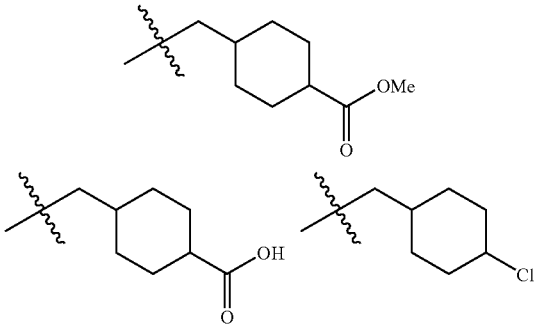

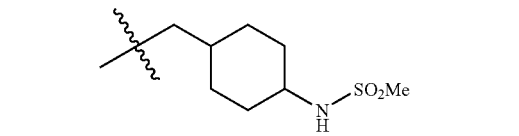

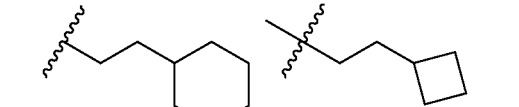

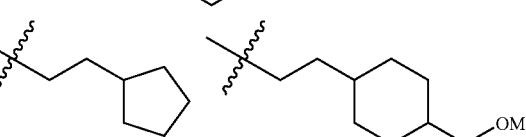

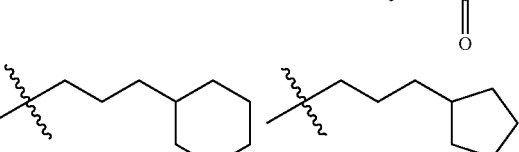

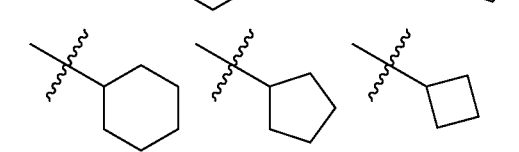

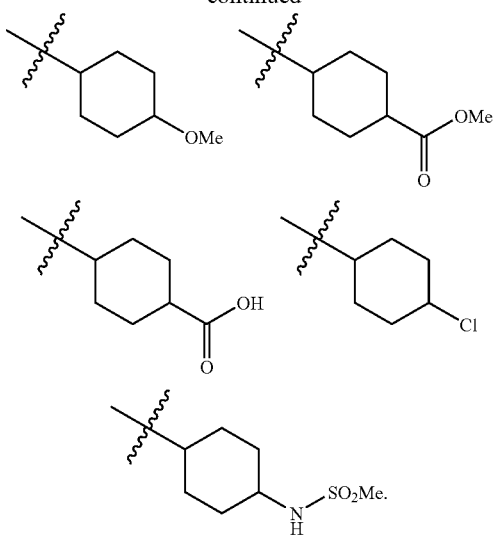

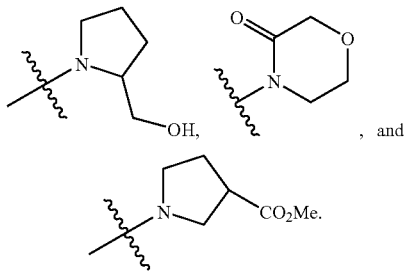

, and

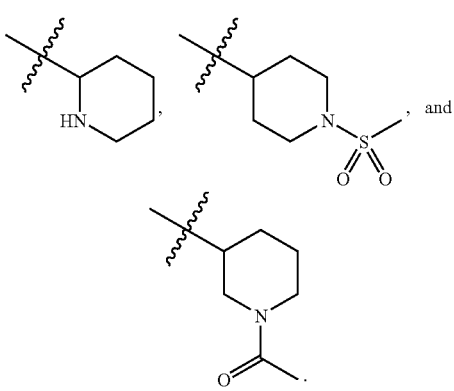

The invention further provides compound of Formula II-a or II-b, wherein $R_1$ is of the formula:

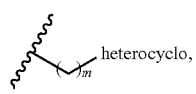

m = 0, 1, 2 and wherein the heterocyclo moiety is unsubstituted or substituted. The heterocyclo moiety forming part (m=1 or 2) or all (m=0) of $R_1$, includes but is not limited to azetidinyl, pyrrolidinyl, morpholinyl, piperidinyl, or piperazinyl. An N-attached heterocyclo is a heterocyclo moiety wherein the heterocyclo moiety is attached to the compound of formula II-a or b through a nitrogen that forms part of the heterocyclo ring. Non-limiting N-attached heterocyclo include but are not limited to

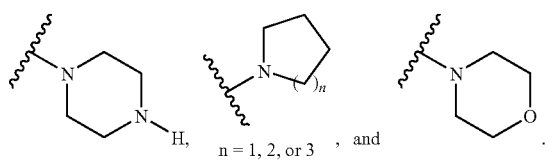

n = 1, 2, or 3, and

In some embodiments, an N-attached heterocyclo is a moiety having the following formula:

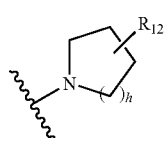

wherein h is 1, 2, or 3, and $R_{12}$ is hydrogen, hydroxy, alkoxy, alkyl, oxo, —$(CH_2)_n$—OH, —C(O)alkyl, —C(O)$_2$alkyl, —C(O)aryl, or —SO$_2$alkyl. Examples include, but are not limited to, In some embodiments, a C-attached heterocyclo is a heterocyclo moiety wherein the heterocyclo moiety is attached to the compound of formula II-a or b through a carbon that forms part of the heterocyclo ring. Non-limiting examples include In some embodiments, a C-attached heterocyclo is a moiety of the following formula:

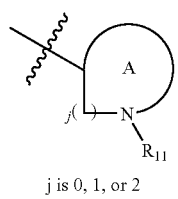

j is 0, 1, or 2 wherein $R_{11}$ is hydrogen, —C(O)alkyl, —C(O)aryl, —C(O)NH$_2$, —C(O)NHalkyl, —C(O)N(alkyl)$_2$, —SO$_2$alkyl, —SO$_2$aryl, —SO$_2$NH$_2$, —SO$_2$NHalkyl, or —SO$_2$N(alkyl)$_2$; ring A is a 5-, 6-, or 7-membered ring, and j is 0, 1, or 2. Examples include but are not limited to

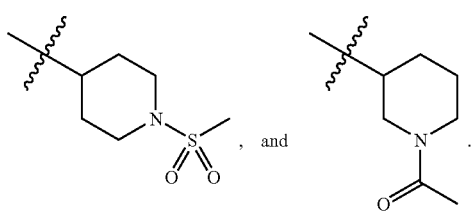

, and

Non-limiting exemplary $R_1$ include the following formulae:

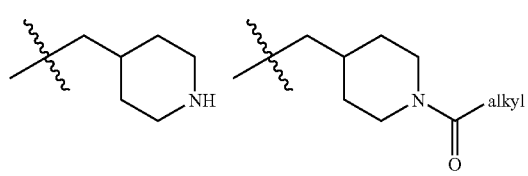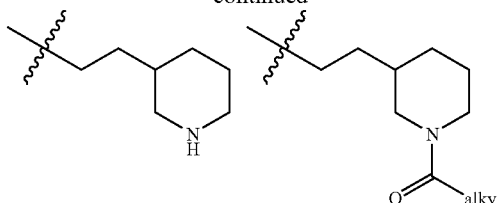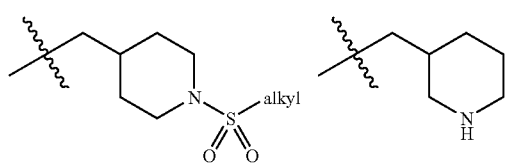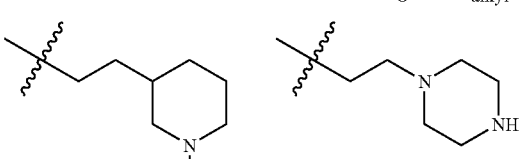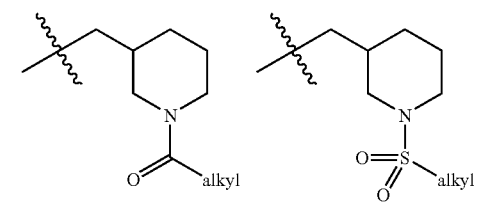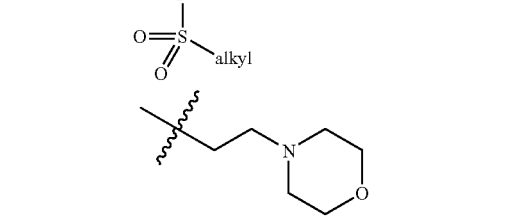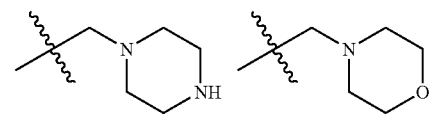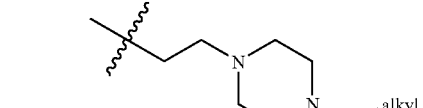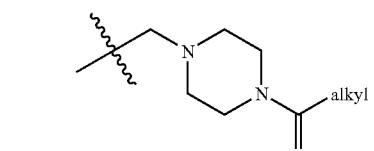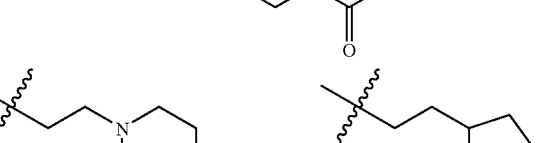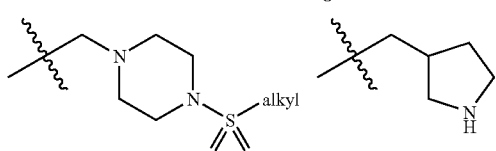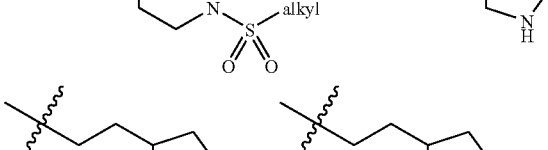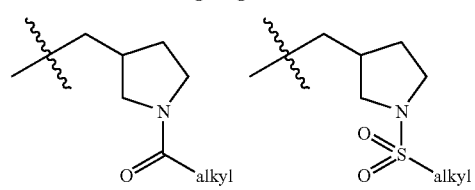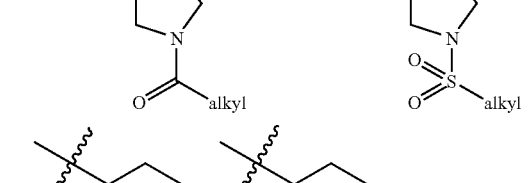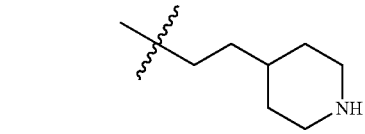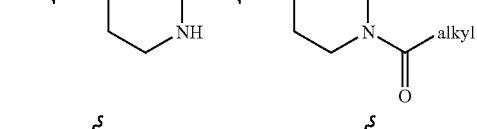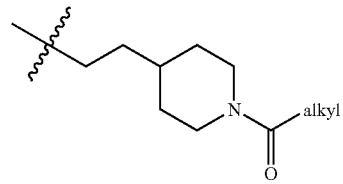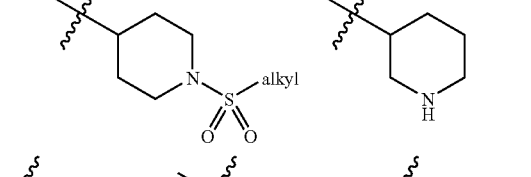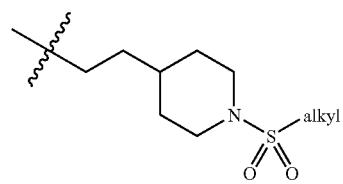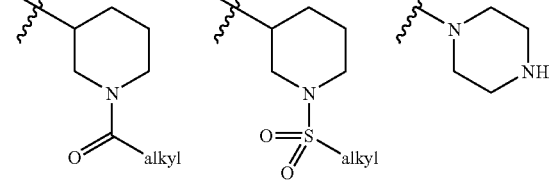

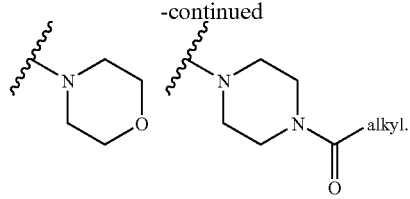

In the above formulae, alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl.

In yet other embodiments, $R_1$ of Formula II-a or II-b is

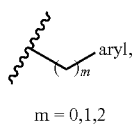

m = 0,1,2 wherein the aryl moiety is unsubstituted or substituted. The aryl moiety forming part (m=1 or 2) or all (m=0) of $R_1$, includes but is not limited to phenyl, naphthyl and fluorenyl.

In some embodiments, the aryl is one of the following moieties:

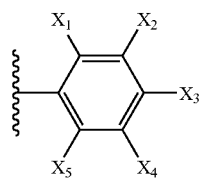

wherein $X_1$-$X_5$ are each independently selected from the group consisting of: —H, -alkyl, —Br, —Cl, —F, —O-alkyl,

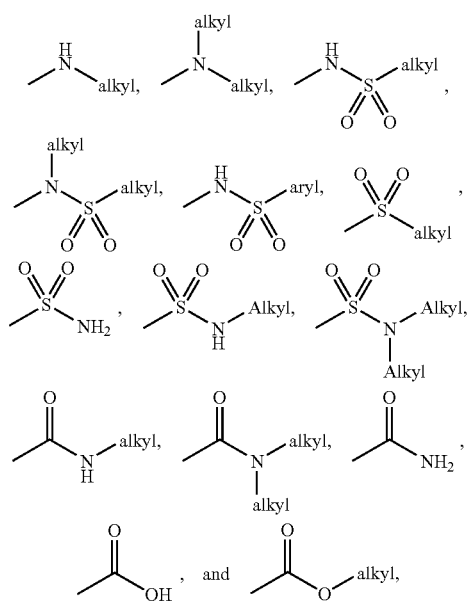

Non-limiting exemplary $R_1$ include the following formulae:

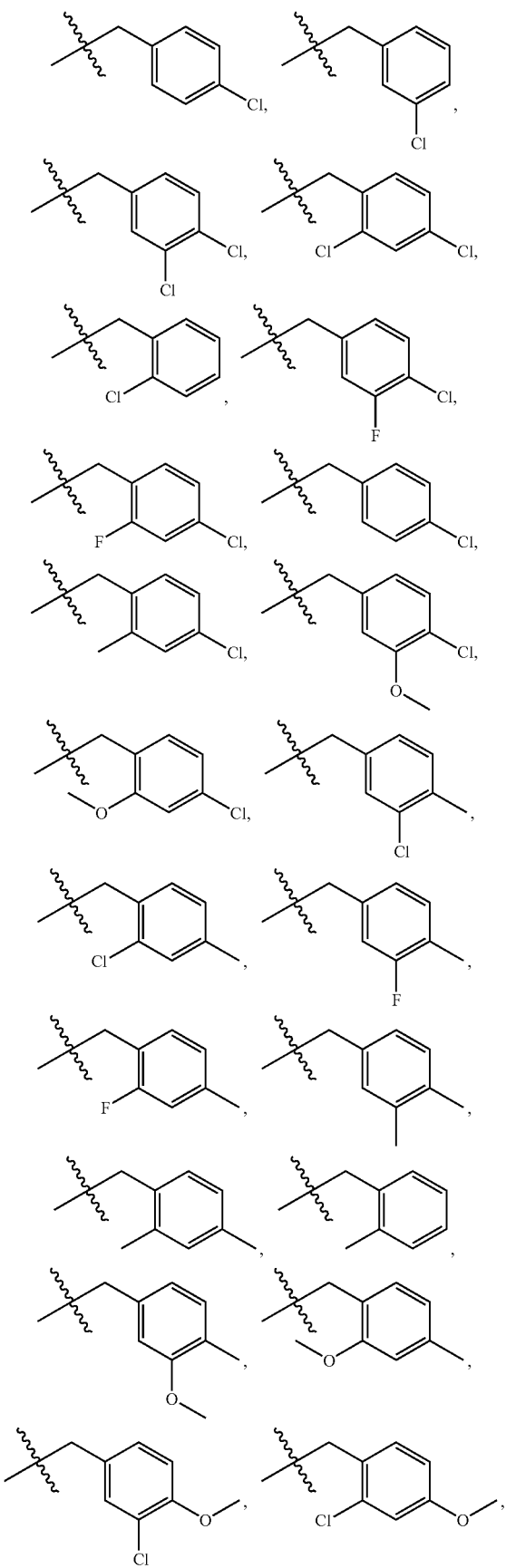

-continued

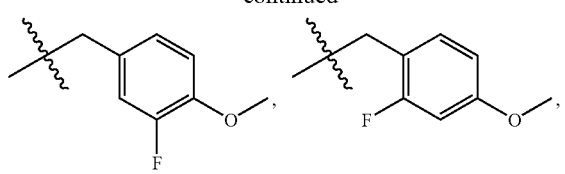

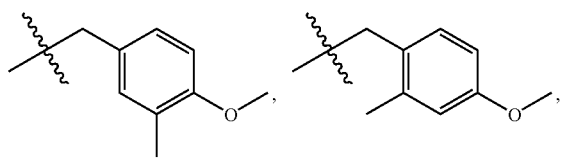

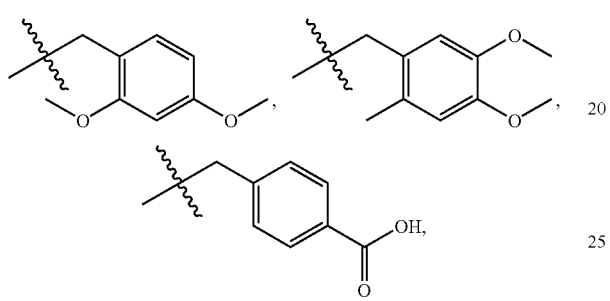

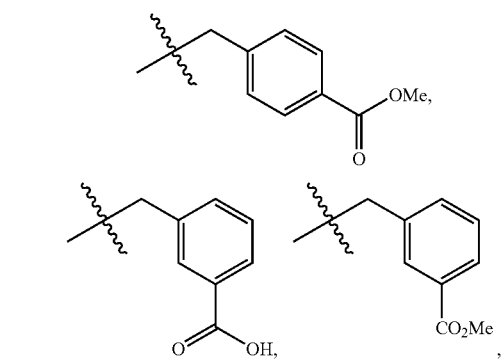

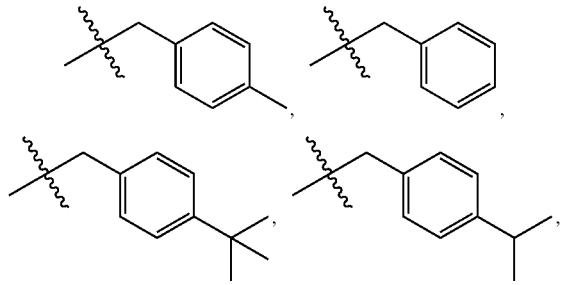

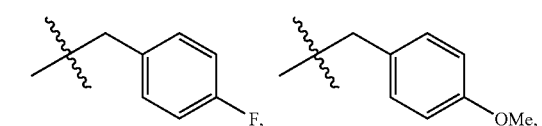

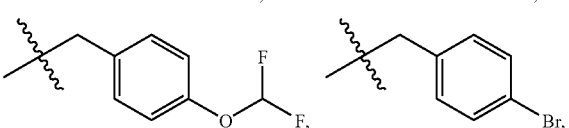

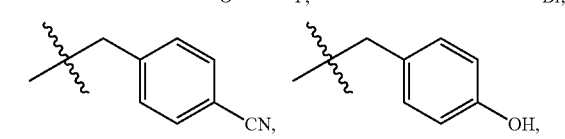

-continued

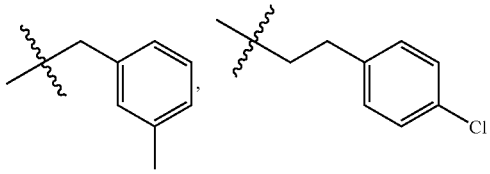

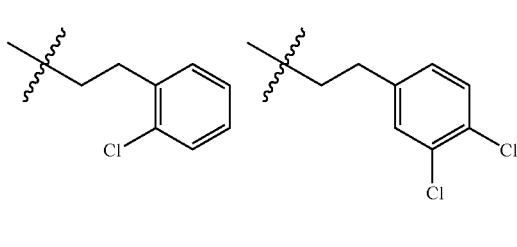

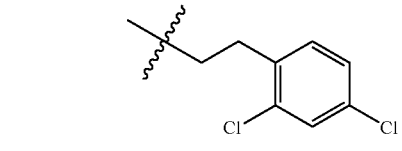

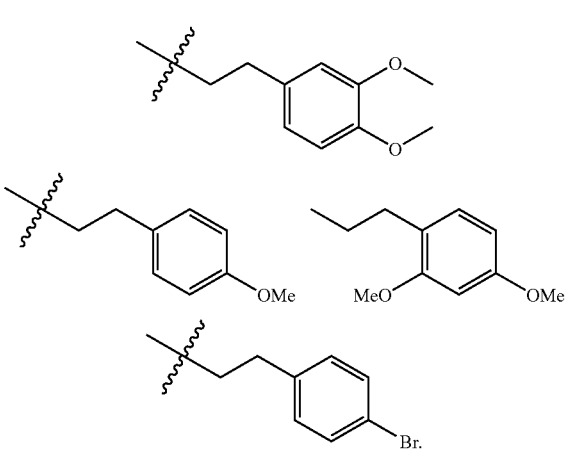

Additionally, R$_1$ of Formula II-a or II-b can be $$\text{heteroaryl,}$$
$$m = 0,1,2$$

wherein the heteroaryl moiety is unsubstituted or substituted. In some embodiments, the heteroaryl moiety is a monocyclic 5 membered heteroaryl. Monocyclic heteroaryl includes but is not limited to pyrrolyl, imidazolyl, thiazolyl, and pyrazolyl.

Alternatively, when R$_1$ is $$\text{heteroaryl,}$$
$$m = 0,1,2$$

heteroaryl may be a six membered heteroaryl moiety. The six membered heteroaryl moiety includes but is not limited to 2-pyridyl, 3-pyridyl, 4-pyridyl, pyrimidinyl, pyrazinyl, or triazinyl.

33

In some embodiments, the $R_1$ heteroaryl is

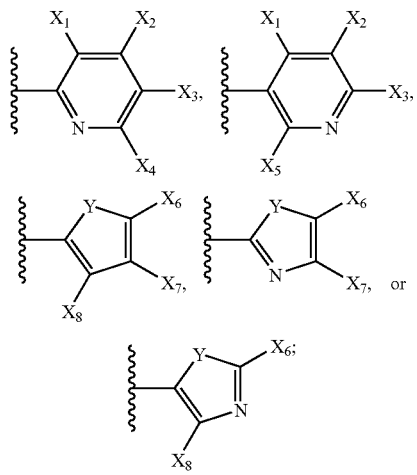

wherein $X_1$-$X_5$ are each independently selected from the group consisting of: —H, -alkyl, —I, —Br, —Cl, —F, —O-alkyl,

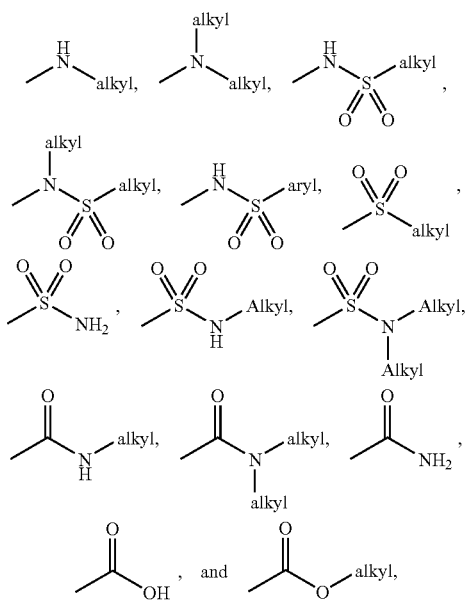

Y is selected from the group consisting of: —O, —S, —NH, —N-alkyl, and —N-acyl; $X_6$ is selected from the group consisting of: —H, —CH$_3$, —I, —Cl, —F, CF$_3$ and —OCH$_3$; and $X_7$ and $X_8$ are independently selected from the group consisting of: H and CH$_3$.

Non-limiting examples of $R_1$ include the following formulae:

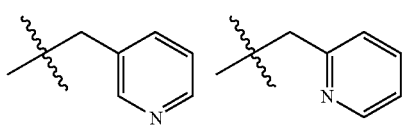

34

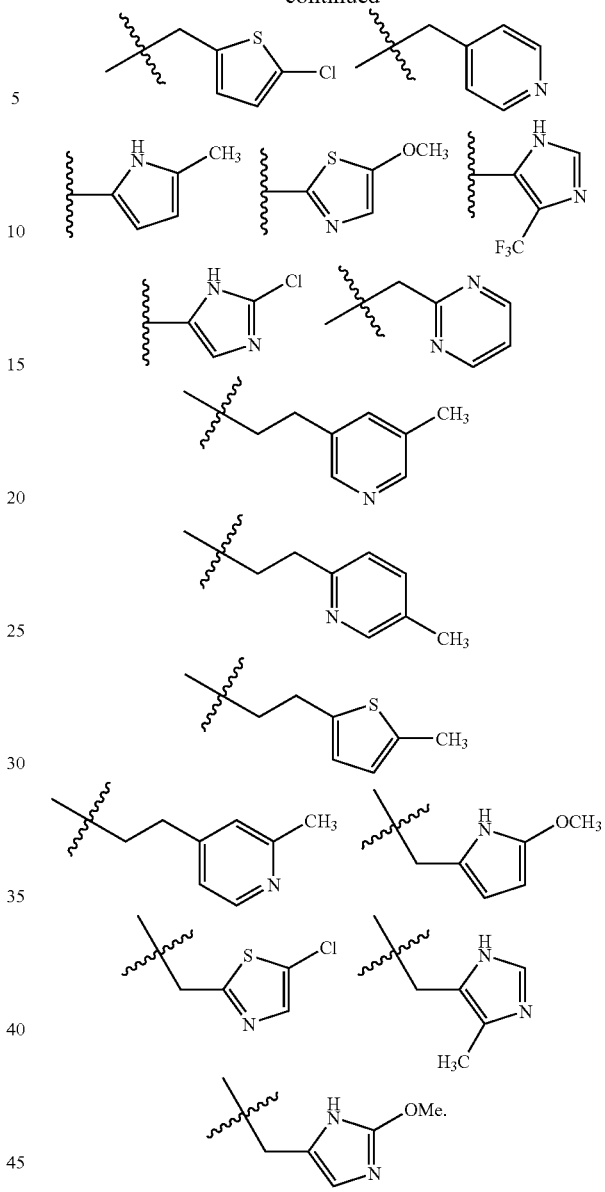

The alkyl, cycloalkyl, heterocyclo, aryl or heteroaryl moiety of $R_1$ may be substituted by one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

In various embodiments of the compounds of Formula II-a or II-b, $R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$ NH$_2$, —SO$_2$ NH(alkyl), NHSO$_2$(alkyl), heteroaryl, N-attached heterocyclo, or C-attached heterocyclo. In some embodiments, $R_3$ is —H or —OH. In other embodiments, $R_3$ is —O(CH$_2$)$_n$X, or —(CH$_2$)$_n$X, wherein X is —NH$_2$, Non limiting examples include: —OCH$_2$CH$_2$NH$_2$ and —CH$_2$CH$_2$NH$_2$. In yet other embodiments, $R_3$ is —O(CH$_2$)$_n$ X, or —(CH$_2$)$_n$X, wherein X is —NH(alkyl), wherein the alkyl is substituted or unsubstituted. Alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. Examples of $R_3$—O(CH$_2$)$_n$NH(alkyl), or —(CH$_{2n}$NH(alkyl), include but are not limited to —OCH$_2$CH$_2$NHMe, —OCH$_2$CH$_2$ CH$_2$NHEt, —CH$_2$CH$_2$NH(iso-propyl), and —CH$_2$CH$_2$ CH$_2$NHMe.

The invention also provides compounds of Formula II, II-a, and II-b, wherein $R_3$ is —O(CH$_{2n}$X, or —(CH$_2$)$_n$X, wherein X is —N(alkyl)$_2$,), wherein the alkyl is substituted or unsubstituted. Alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. Examples of $R_3$—O(CH$_2$)$_n$N(alkyl)$_2$, or —(CH$_2$)$_n$ N(alkyl)$_2$, include but are not limited to —OCH$_2$CH$_2$(Me)$_2$, —OCH$_2$CH$_2$ CH$_2$N(Et)$_2$, —CH$_2$CH$_2$N(iso-propyl)$_2$, and —CH$_2$CH$_2$CH$_2$N(Me)$_2$. Alternatively, $R_3$ is —O(CH$_2$)$_n$X, or —(CH$_2$)$_n$X, wherein X is —OH. Examples include but are not limited to —OCH$_2$CH$_2$OH, —OCH$_2$CH$_2$ CH$_2$OH, —CH$_2$CH$_2$OH, and —CH$_2$CH$_2$CH$_2$OH.

In yet other embodiments, $R_3$ is —O(CH$_2$)$_n$X, or —(CH$_2$)$_n$X, wherein X is O-alkyl, wherein the alkyl is unsubstituted or substituted. Alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. Examples of $R_3$ is —O(CH$_2$)$_n$O-alkyl, or —(CH$_2$)$_n$O-alkyl, include but are not limited to —OCH$_2$CH$_2$OMe, —OCH$_2$CH$_2$ CH$_2$OEt, —CH$_2$CH$_2$O(iso-propyl), and —CH$_2$CH$_2$ CH$_2$OEt.

In some other embodiments, $R_3$ is —O(CH$_2$)$_n$X, or —(CH$_2$)$_n$X, wherein X is —O-aryl, wherein the aryl is substituted or unsubstituted. Aryl includes but is not limited to phenyl, naphthyl and fluorenyl. Examples of $R_3$—O(CH$_2$)$_n$ O-aryl, or —(CH$_2$)$_n$O-aryl include but are not limited to —OCH$_2$CH$_2$O-phenyl, —OCH$_2$CH$_2$CH$_2$O-(3-methoxyphenyl), —CH$_2$CH$_2$O-(4-methyl phenyl), and —CH$_2$CH$_2$CH$_2$O-phenyl. In other embodiments, $R_3$ is —O(CH$_2$)$_n$X, or —(CH$_2$)$_n$X, wherein X is —SO$_2$(alkyl) and alkyl is unsubstituted or substituted. Alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. Examples include but are not limited to —OCH$_2$CH$_2$SO$_2$Me, —OCH$_2$CH$_2$ CH$_2$SO$_2$Et, —CH$_2$CH$_2$SO$_2$(butyl) and —CH$_2$CH$_2$ CH$_2$SO$_2$Me. Additionally, $R_3$ is —O(CH$_2$)$_n$X, or —(CH$_2$)$_n$X, wherein X is —SO$_2$NH$_2$ or —SO$_2$NH(alkyl), and alkyl is unsubstituted or substituted. Alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. Examples include but are not limited to —OCH$_2$CH$_2$SO$_2$NH$_2$, —OCH$_2$CH$_2$CH$_2$SO$_2$NHMe, —CH$_2$CH$_2$SO$_2$NH$_2$ and —CH$_2$CH$_2$CH$_2$SO$_2$ NHMe.

In other embodiments, $R_3$ is —O(CH$_2$)$_n$X, or —(CH$_2$)$_n$X, wherein X is NHSO$_2$(alkyl), and alkyl is unsubstituted or substituted. Alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. Examples include but are not limited to —OCH$_2$CH$_2$NHSO$_2$Me, —OCH$_2$CH$_2$CH$_2$NHSO$_2$Et, —CH$_2$CH$_2$NHSO$_2$Me and —CH$_2$CH$_2$CH$_2$SO$_2$ NHSO$_2$Et.

The invention also provides compounds of Formula II-a and II-b, wherein $R_3$ is —O(CH$_2$)$_n$X, or —(CH$_2$)$_n$X, wherein X is heteroaryl, and the heteroaryl is unsubstituted or substituted. In some embodiments, the heteroaryl moiety is a monocyclic 5 membered heteroaryl. Monocyclic heteroaryl includes but is not limited to pyrrolyl, imidazolyl, thiazolyl, and pyrazolyl. Additional nonlimiting monocyclic 5 membered heteroaryl moieties include the following formulae:

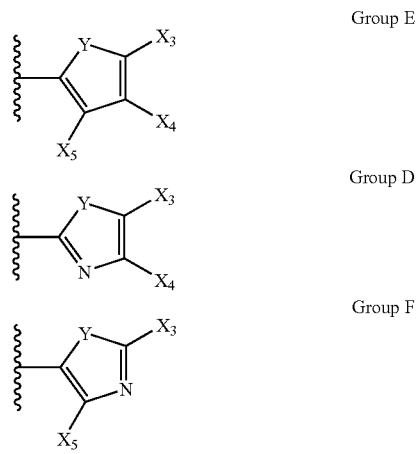

Group E

Group D

Group F

For compounds of Group D, E, and F, Y is selected from the group consisting of: —O, —S, —NH, —N-alkyl, and —N-acyl; $X_3$ is selected from the group consisting of: —H, —CH$_3$, —Cl, —I, —F, CF$_3$ and —OCH$_3$; and $X_4$ and $X_5$ are, when present, independently selected from the group consisting of: H and CH$_3$.

Alternatively, heteroaryl may be a six membered heteroaryl moiety. The six membered heteroaryl moiety includes but is not limited to 2-pyridyl, 3-pyridyl, 4-pyridyl, pyrimidinyl, pyrazinyl, or triazinyl. Non limiting $R_3$—O(CH$_2$)$_n$-heteroaryl or —(CH$_2$)$_n$heteroaryl include —OCH$_2$CH$_2$-pyridinyl, —OCH$_2$CH$_2$ CH$_2$-(4-methyl-pyridin-2-yl), —CH$_2$CH$_2$-(thiazolyl), and —CH$_2$CH$_2$ CH$_2$-pyrazinyl.

In yet other embodiments, $R_3$ is —O(CH$_2$)$_n$X, or —(CH$_2$)$_n$X, wherein X is N-attached heterocyclo, or C-attached heterocyclo, and the heterocyclo is unsubstituted or substituted. The heterocyclo includes but is not limited to azetidinyl, pyrrolidinyl, morpholinyl, piperidinyl, or piperazinyl. Non limiting $R_3$—O(CH$_2$)$_n$-heterocyclo (which includes both N-attached or C-attached heterocyclo) or —(CH$_2$)$_n$heterocyclo (which includes both N-attached or C-attached heterocyclo) include —OCH$_2$CH$_2$-morpholinyl, —OCH$_2$CH$_2$ CH$_2$-(4N-methyl-piperazinyl), —CH$_2$CH$_2$-(pyrrolidin-2-yl), and —CH$_2$CH$_2$ CH$_2$-(4N-methyl-piperazinyl).

The alkyl, aryl, heteroaryl and heterocyclo moiety forming all or part of X may be substituted by one or more substituents which is selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl. Additionally, the alkyl and heterocyclo moiety forming all or part of X may be substituted by oxo.

Other $R_3$ moieties useful in the compounds of the invention are listed in Table 2b, 2e, and 2h.

In various embodiments of compounds of Formula II, II-b, or another isostere scaffold as described above, each of $R_4$-$R_7$, is independently selected from the group consisting of: —H, —I, —Cl, —F, —CH$_3$, —OCH$_3$, —OH, —NH$_2$, —NO$_2$,

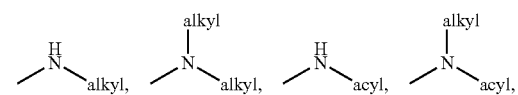
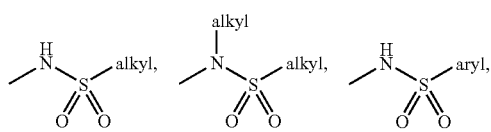
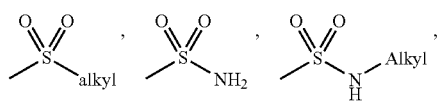
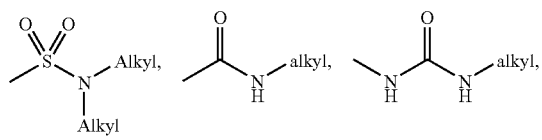
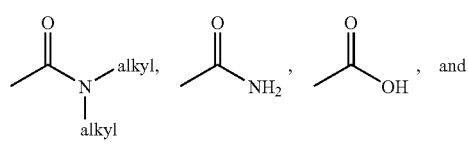
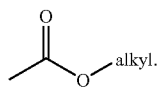

In the moieties forming part of $R_3$-$R_7$, the alkyl and aryl moieties are unsubstituted or substituted. The alkyl moieties that form part of $R_3$-$R_7$ include but are not limited to methyl, ethyl, n-propyl, iso-propyl, n-butyl, iso-butyl, tert-butyl, n-pentyl, iso-pentyl, n-hexyl, septyl, heptyl, nonyl, and decyl. The aryl moieties that form part of $R_3$-$R_7$ include but are not limited to phenyl, naphthyl and fluorenyl. The alkyl and aryl moieties that form part of $R_3$-$R_7$ may be substituted by one or more substituents which is selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

In one embodiment, at least one of $R_4$-$R_7$ is a hydrogen. In other embodiments, where $R_3$ is present, $R_3$ is hydrogen. In further embodiments, at least two of $R_4$-$R_7$ is a hydrogen. Alternatively, at least two of $R_4$-$R_7$ are hydrogen, and the remaining $R_4$-$R_7$ groups (and $R_3$, if present) are independently selected from the group consisting of: —Cl, —F, —CH$_3$, and —OCH$_3$. In yet other embodiments, $R_5$ and $R_6$ are substituted, and the substituted moiety is, for each substituted position, independently selected from the group consisting of: —Cl, —F, —CH$_3$, and —OCH$_3$, while $R_4$ and $R_7$ (and $R_3$ if present) are hydrogen.

In some other embodiments, $R_4$ and $R_5$, $R_5$ and $R_6$, or $R_6$ and $R_7$ are joined together with a bond to form a ring; or, optionally, $R_4$ and $R_5$, $R_5$ and $R_6$, or $R_6$ and $R_7$ are joined together to form a 1,2-(methylenedioxy)benzene ring system, such as

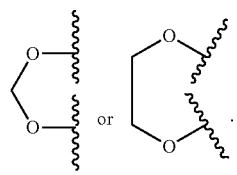

In one embodiment, the ring is composed of a structure selected from the group consisting of:

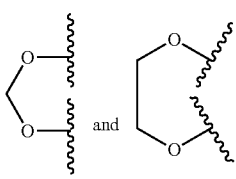

In a further embodiment, $R_5$ and $R_6$ are connected by one of the rings having a structure selected from the group consisting of:

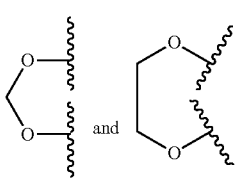

In some embodiments of the invention, the compound of Formula II-a is not

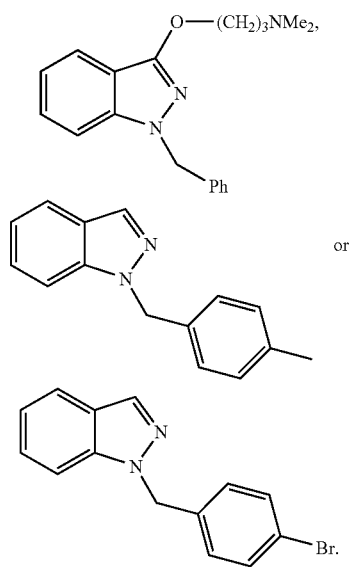

In yet another embodiment, the present invention provides a compound of Formula II-a shown below.

Formula II-a

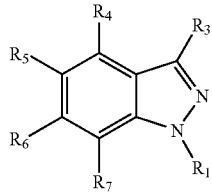

In some embodiments, the compound of Formula II-a is the compound wherein $R_1$ is selected from the group consisting of: —H or

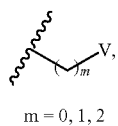

m = 0, 1, 2 and V is selected from alkyl, aryl,

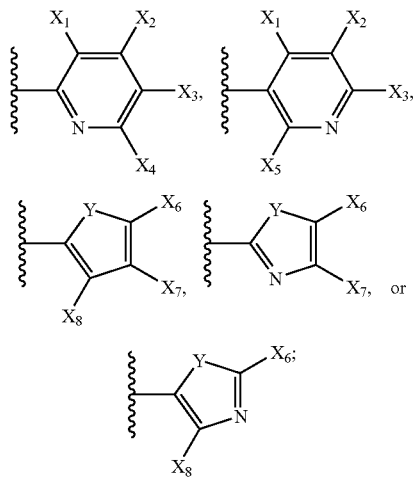

$X_1$-$X_5$ are each independently selected from the group consisting of: —H, -alkyl, —I, —Br, —Cl, —F, —O-alkyl,

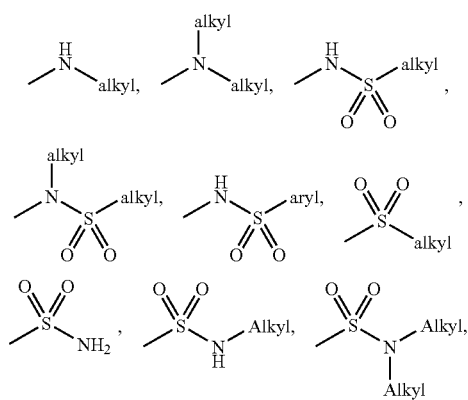

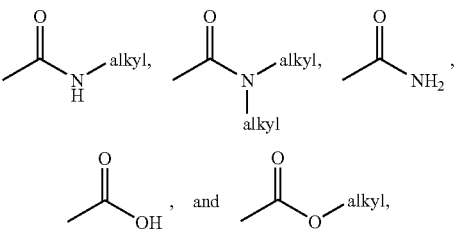

Y is selected from the group consisting of: —O, —S, —NH, —N-alkyl, and —N-acyl; $X_6$ is selected from the group consisting of: —H, —CH$_3$, —I, —Cl, —F, CF$_3$ and —OCH$_3$; and $X_7$ and $X_8$ are independently selected from the group consisting of: —H and CH$_3$; each of $R_4$-$R_7$ is independently selected from the group consisting of: —H, —I, —Br, —Cl, —F, —CH$_3$, —CN, —OH, —OCH$_3$, —NO$_2$, —NH$_2$, —OCH$_2$CH$_2$O-alkyl, —NHCO(alkyl), —NHCO(aryl),

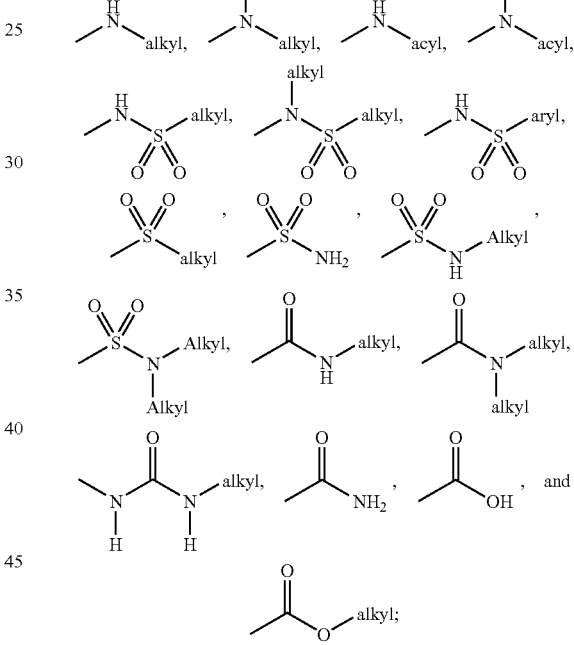

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system.

In other embodiments, the compound of Formula II-a is the compound wherein $R_3$ is —O(CH$_2$)$_n$X, or —(CH$_2$)$_n$X, wherein X is selected from the group consisting of: —OCH$_3$, —OCH$_2$CH$_3$, —OCH$_2$CH$_2$OH, —OCH$_2$CH$_2$OCH$_3$,

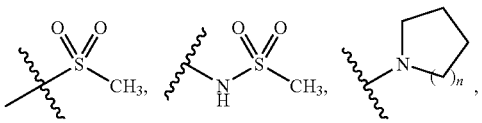

n = 1, 2, or 3

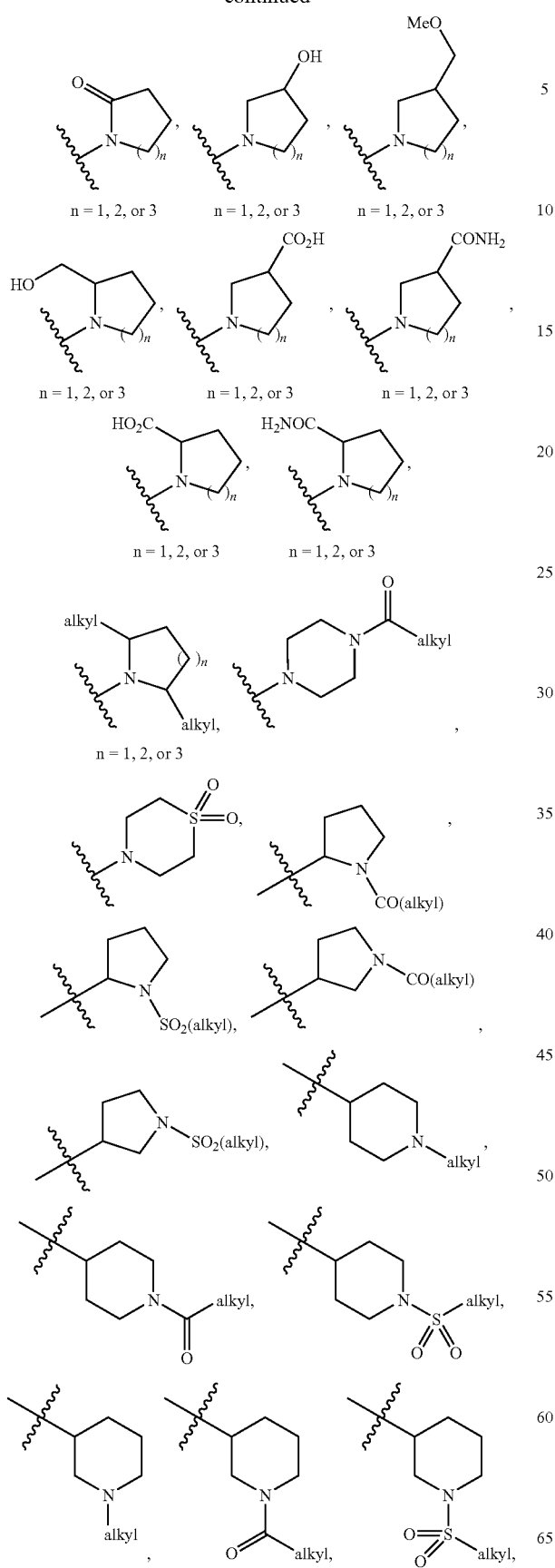
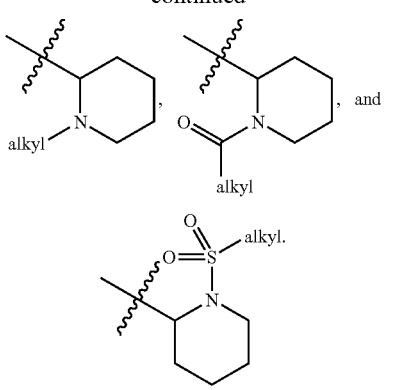
In other embodiments, the compound of Formula II-a is the compound wherein $R_1$ is selected from the group consisting of:
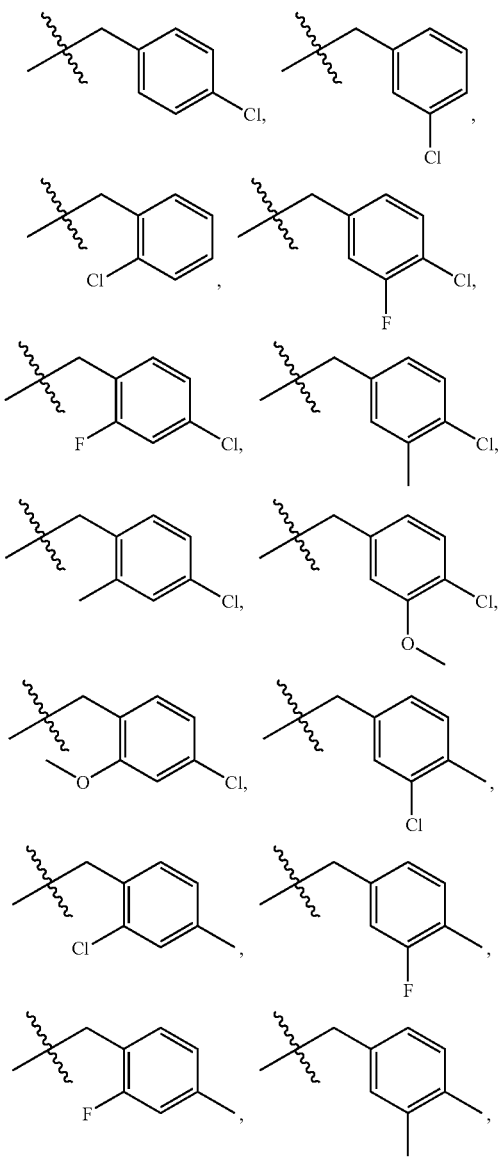

-continued
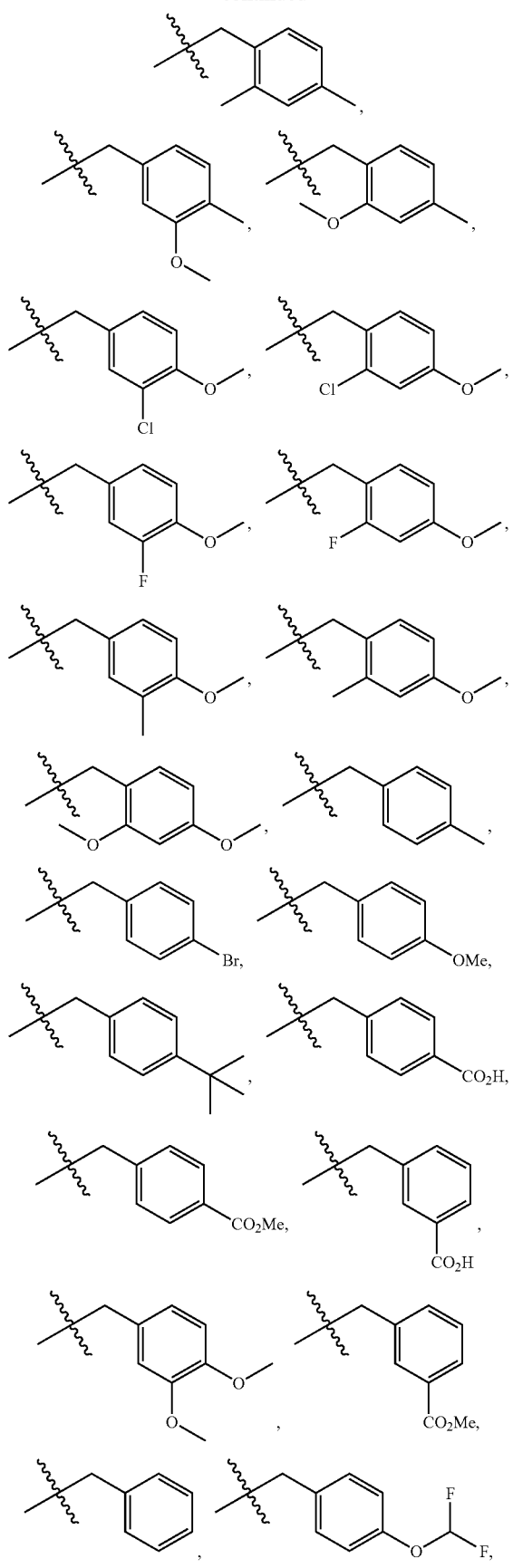
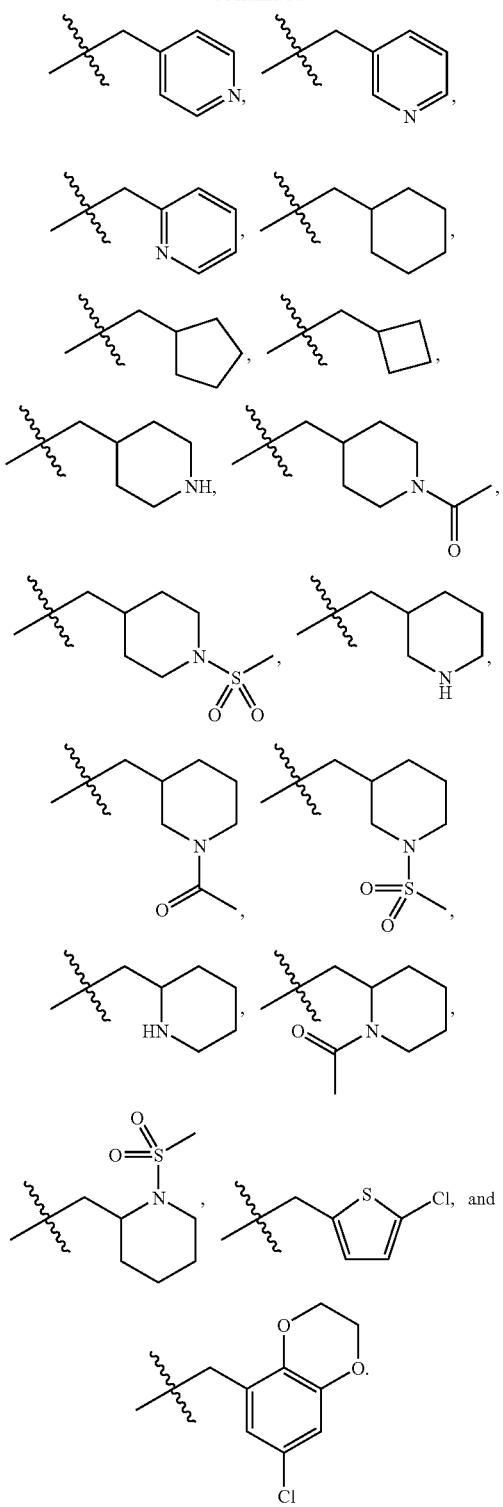
In yet other embodiments, the compound of Formula II-a is the compound, wherein $R_1$ is —$CH_2V$, wherein V is selected from the group consisting of: cycloalkyl, heterocyclo, aryl and heteroaryl;
$R_3$ is —$O(CH_2)_nX$, or —$(CH_2)_nX$, wherein X is selected from the group consisting of: —$OCH_3$, —$OCH_2CH_3$, —$OCH_2CH_2OH$, —$OCH_2CH_2OCH_3$,

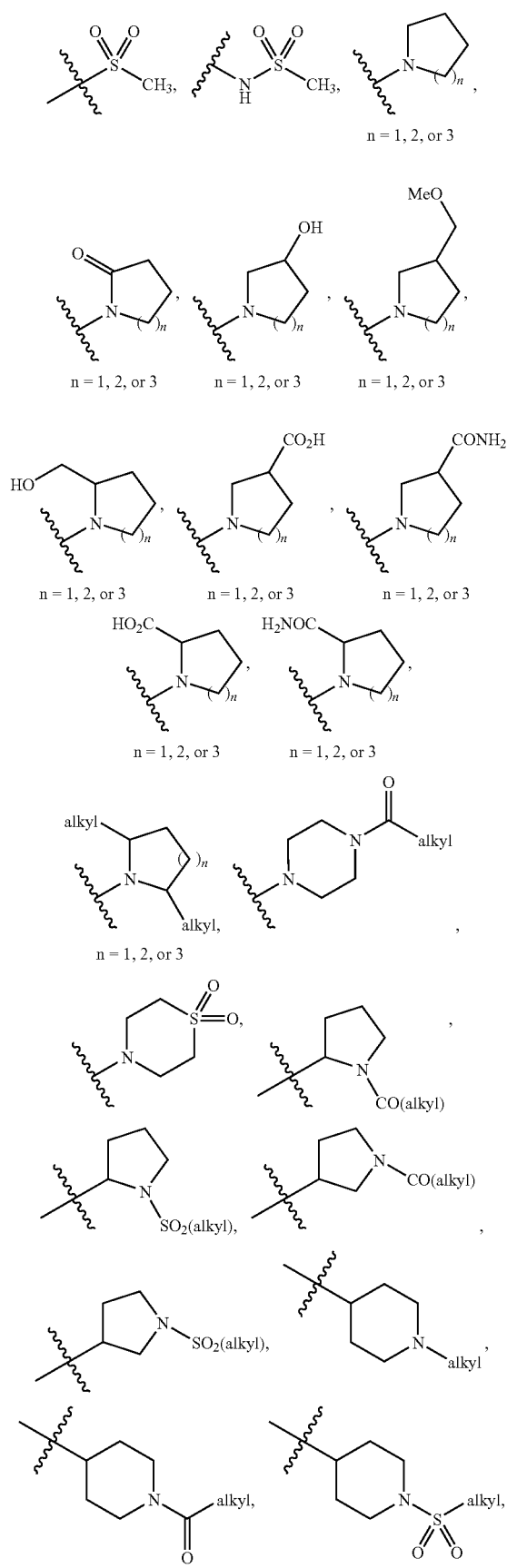
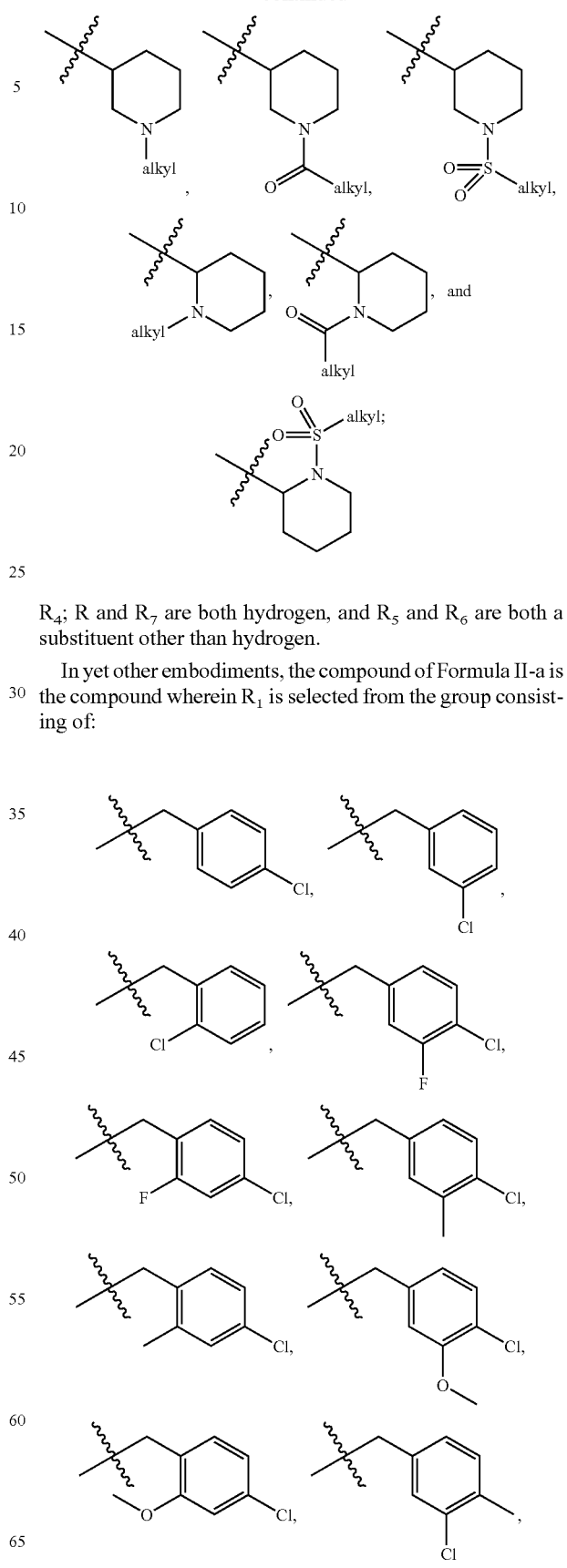
$R_4$; R and $R_7$ are both hydrogen, and $R_5$ and $R_6$ are both a substituent other than hydrogen.
In yet other embodiments, the compound of Formula II-a is the compound wherein $R_1$ is selected from the group consisting of:

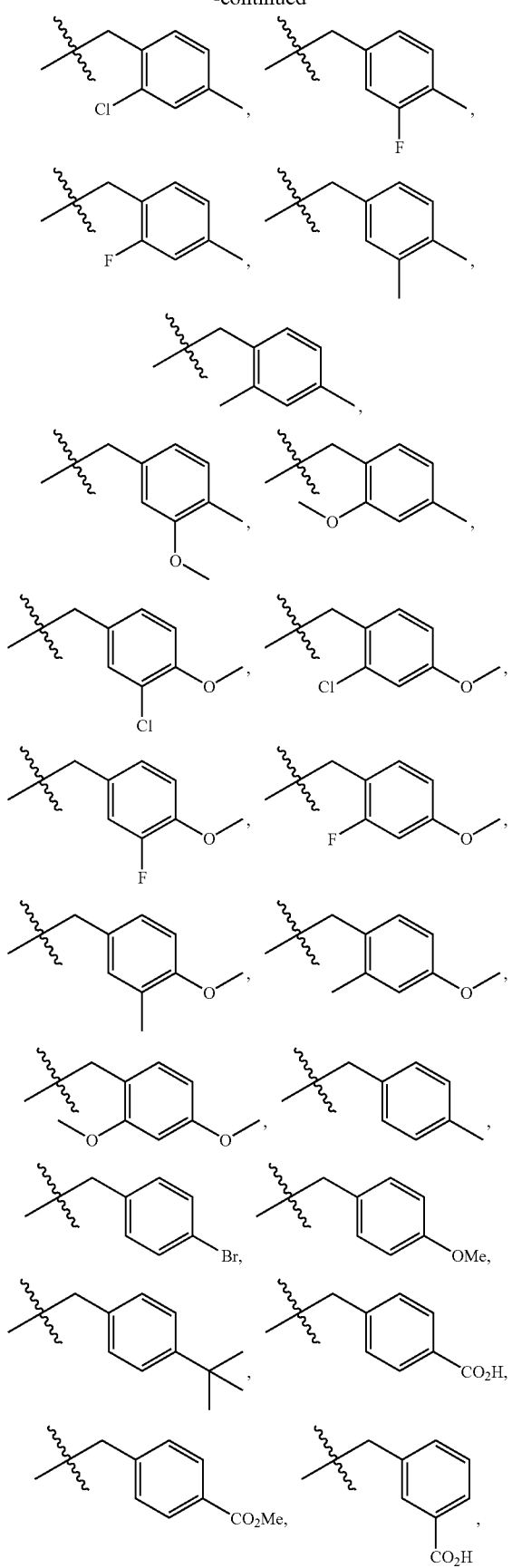
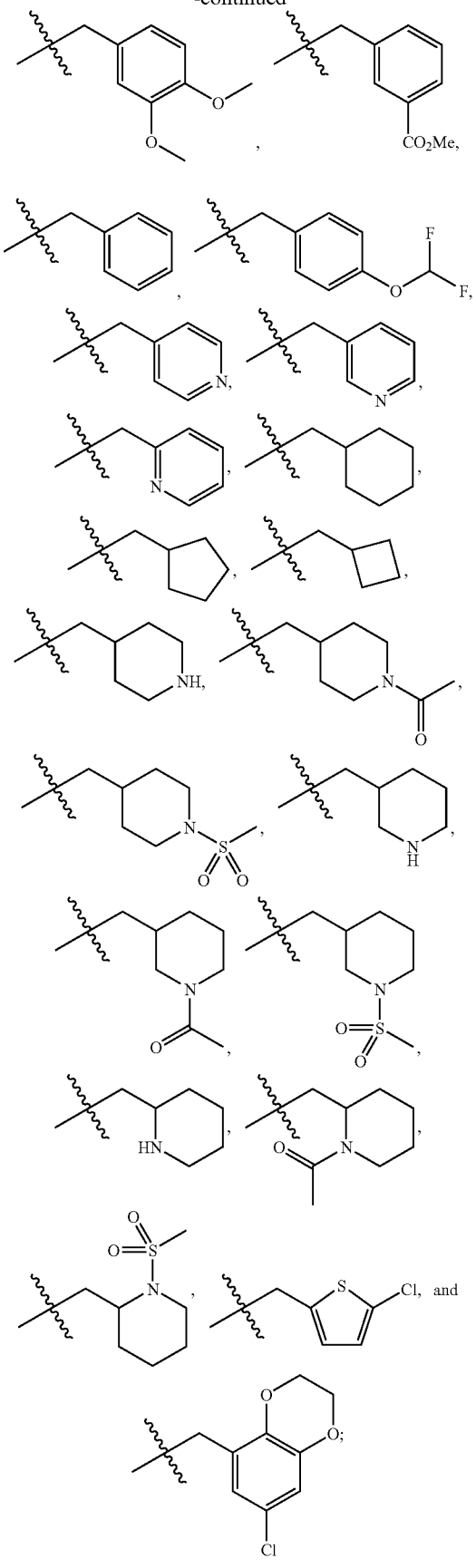

R₃ is selected from: —O(CH₂)₂NMe₂, —O(CH₂)₂NEt₂, —O(CH₂)₃NEt₂,

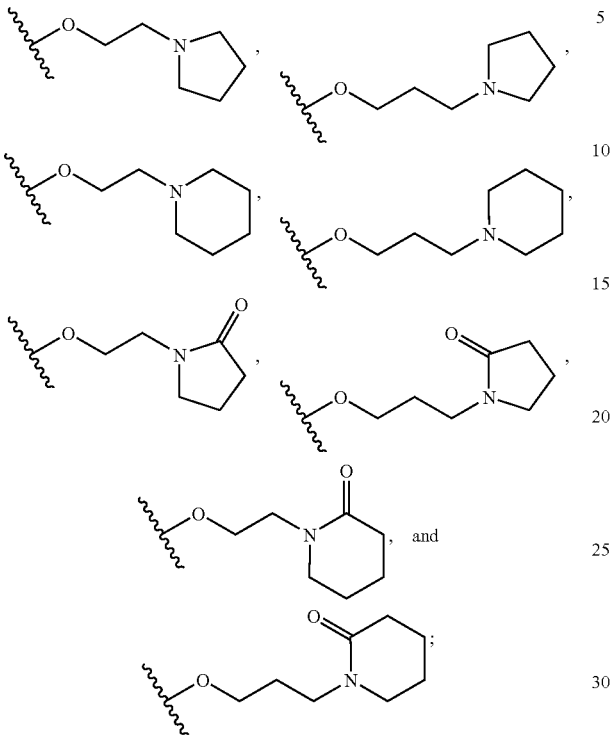

R₄ and R₇ are both hydrogen; and R₅ and R₆ are both not hydrogen.

The invention also provides compounds of Formula II-a wherein R₁ is —CH₂V, wherein V is selected from cycloalkyl, heterocyclo, aryl or heteroaryl; R₃ is —O(CH₂)ₙX, or —(CH₂)ₙX, wherein X is selected from the group consisting of: —OCH₃, —OCH₂CH₃, —OCH₂CH₂OH, —OCH₂CH₂OCH₃,

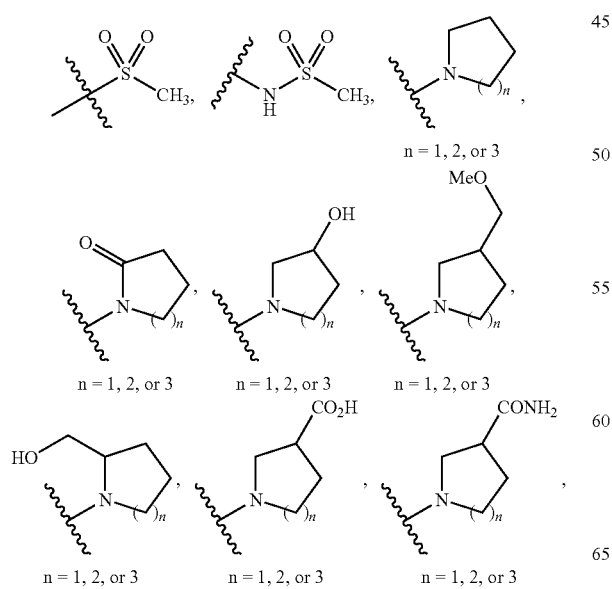

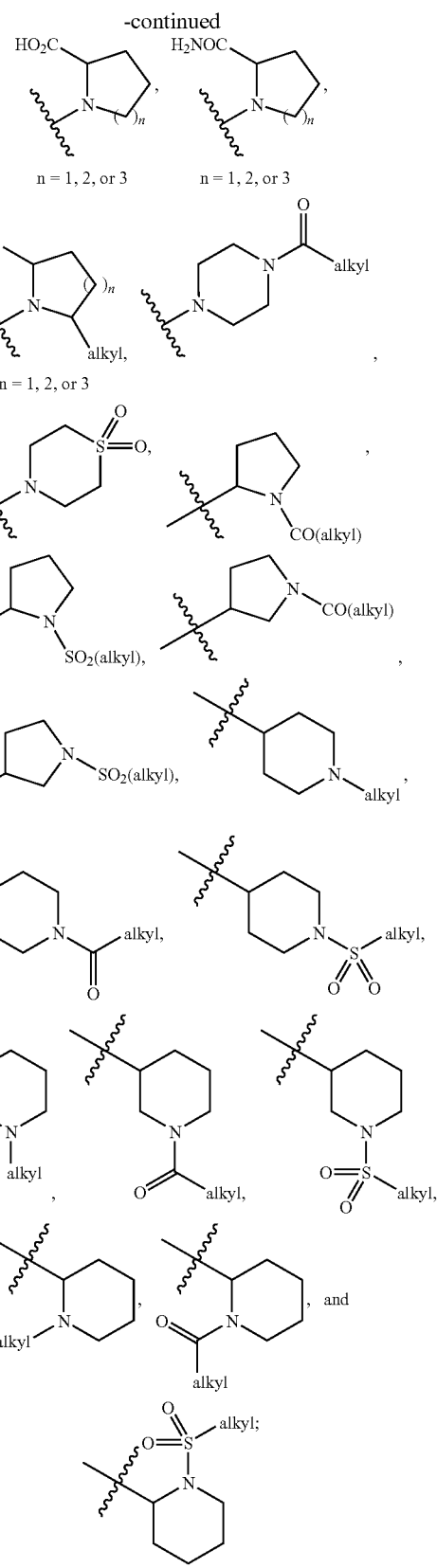

R₄ is —NHC(O)aryl, —NHC(O)alkyl, —NHSO₂aryl or —NHSO₂alkyl; R₇ is hydrogen and R₅ and R₆ are both a substituent other than hydrogen.

The compounds of Formula II-a are also a compound wherein $R_1$ is selected from the group consisting of:
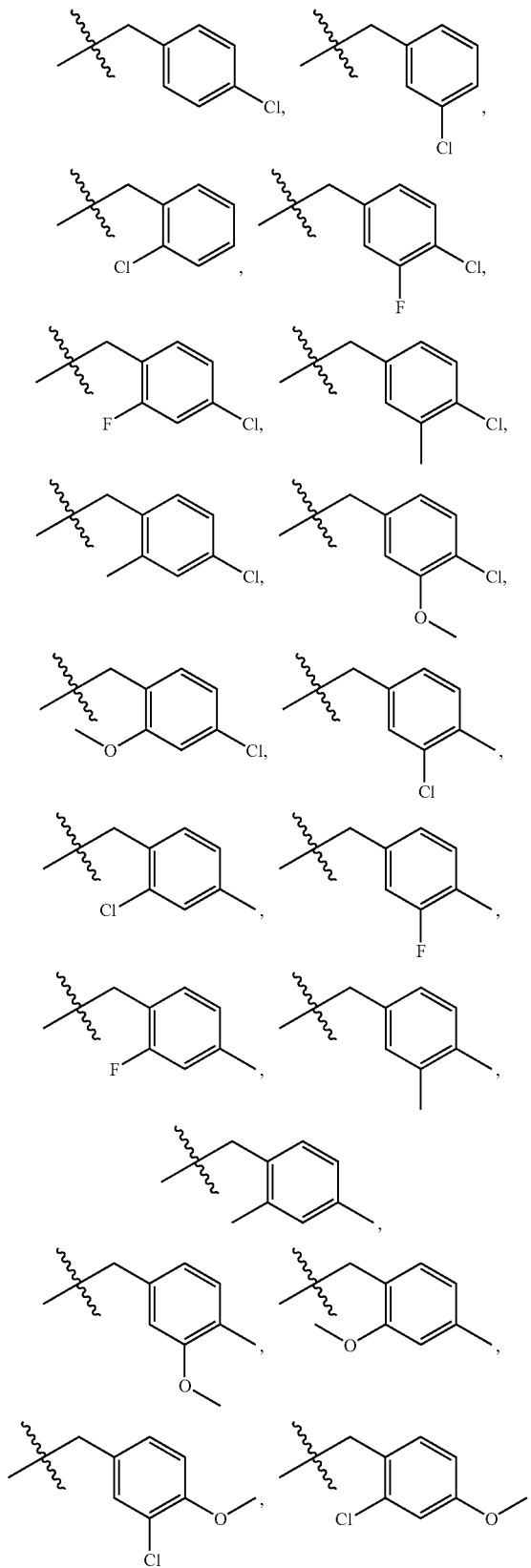
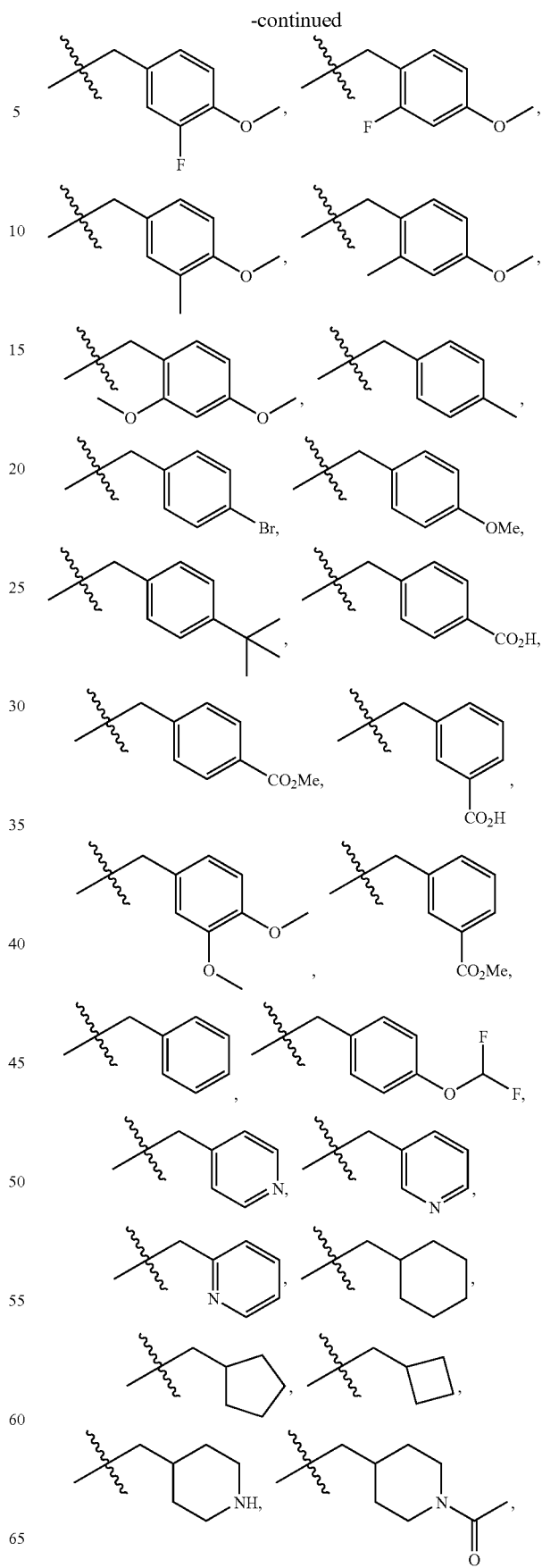

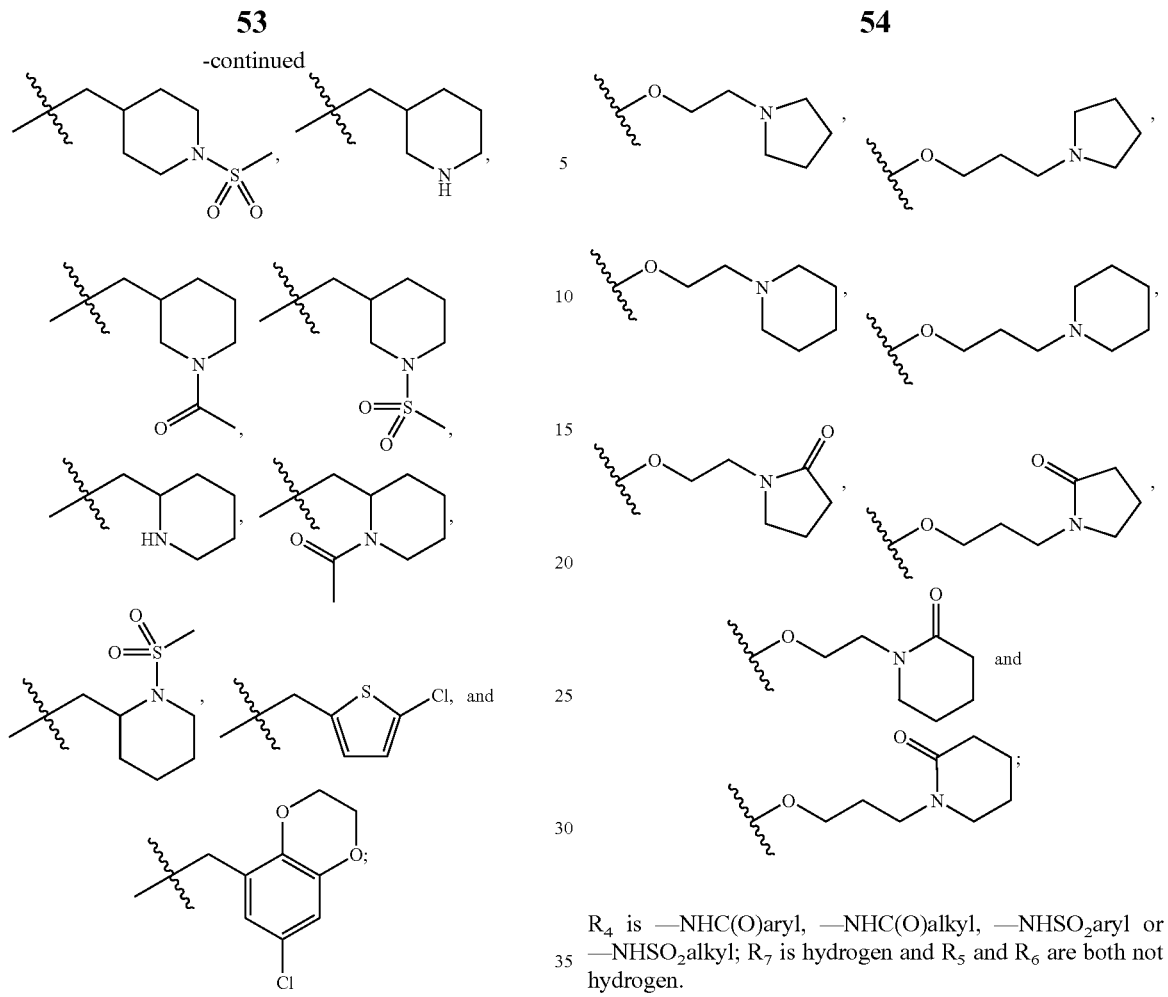

$R_3$ is selected from: —O(CH$_2$)$_2$NMe$_2$, —O(CH$_2$)$_2$NEt$_2$, —O(CH$_2$)$_3$NMe$_2$, —O(CH$_2$)$_3$NEt$_2$, $R_4$ is —NHC(O)aryl, —NHC(O)alkyl, —NHSO$_2$aryl or —NHSO$_2$alkyl; $R_7$ is hydrogen and $R_5$ and $R_6$ are both not hydrogen.

Table 1 shows structures of additional inhibiting agents of the invention and illustrative starting materials to prepare them.

TABLE 1

| | Structure | Illustrative Starting Material |
|---|---|---|
| 1 | 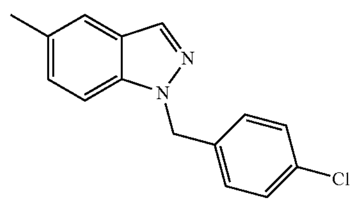 [SMILES: Cc1ccc2c(cnn2Cc2ccc(Cl)cc2)c1] | |
| 2 | 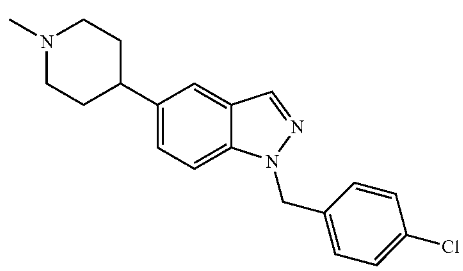 [SMILES: CN1CCC(c2ccc3c(cnn3Cc3ccc(Cl)cc3)c2)CC1] | |

TABLE 1-continued

| | Structure | Illustrative Starting Material |
|---|---|---|
| 3 | 5-(trifluoromethyl)-1-(4-chlorobenzyl)-1H-indazole | 5-(trifluoromethyl)-1H-indazole |
| 4 | 5-cyano-6-fluoro-1-(4-chlorobenzyl)-1H-indazole | 5-cyano-6-fluoro-1H-indazole |
| 5 | 5-chloro-1-(4-chlorobenzyl)-1H-indazole | 5-chloro-1H-indazole |
| 6 | 5,6-dichloro-1-(4-chlorobenzyl)-1H-indazole | 5,6-dichloro-1H-indazole |
| 7 | 5,6-dimethyl-1-(4-chlorobenzyl)-1H-indazole | 5,6-dimethyl-1H-indazole |
| 8 | 6-methyl-1-(4-chlorobenzyl)-1H-indazole | 6-methyl-1H-indazole |
| 9 | 5-chloro-6-methyl-1-(4-chlorobenzyl)-1H-indazole | 5-chloro-6-methyl-1H-indazole |

TABLE 1-continued

| Structure | Illustrative Starting Material |
|---|---|
| 10 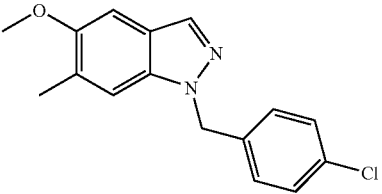 [SMILES: COc1cc2cnn(Cc3ccc(Cl)cc3)c2cc1C] | 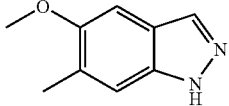 |

Table 2a shows structures of additional inhibiting agents of the invention based on the structure below.

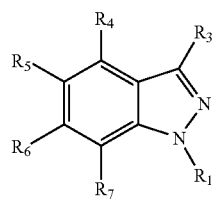

Formula II-a

Some nonlimiting illustrative compounds of the present invention having a structure of Formula II-a include those in which $R_1$ is any $R_1$ moiety described in Table 2a, in combination with any $R_3$ moiety described in Table 2b, and any $R_4$, $R_5$, $R_6$, and $R_7$ as described in Table 2c. A compound of Formula II-a includes any combination of $R_1$, $R_3$, $R_4$, $R_5$, $R_6$, and $R_7$. Additional exemplary compounds of Formula II-a a are illustrated in Tables 3, 4 and 5.

TABLE 2a $R_1$ moieties of Formula II-a include, but are not limited to, the following:
Illustrative $R_1$ moieties

| hydrogen R1-1 | methyl R1-2 | ethyl R1-3 |
|---|---|---|
| 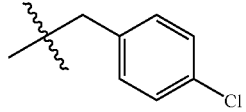 R1-4 | 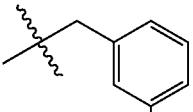 R1-5 | 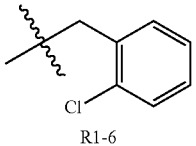 [SMILES: *Cc1ccccc1Cl] R1-6 |
| 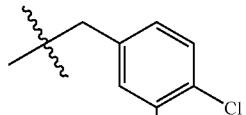 R1-7 | 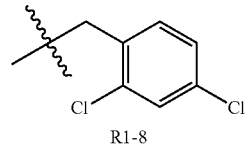 [SMILES: *Cc1ccc(Cl)cc1Cl] R1-8 | 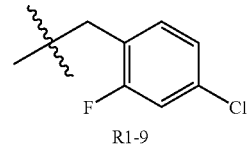 [SMILES: *Cc1ccc(Cl)cc1F] R1-9 |
| 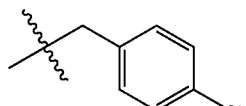 R1-10 | 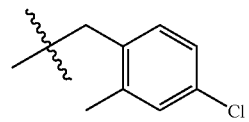 R1-11 | 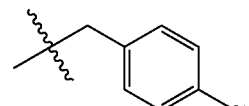 R1-12 |
| 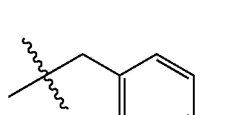 R1-13 | 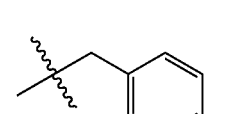 R1-14 | 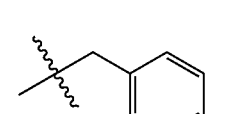 R1-15 |

TABLE 2a-continued
R₁ moieties of Formula II-a include, but are not limited to, the following:
Illustrative R₁ moieties
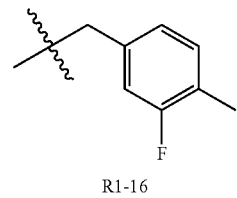 [SMILES: *Cc1ccc(C)c(F)c1]
R1-16
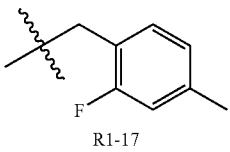
R1-17
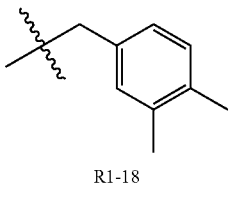 [SMILES: *Cc1ccc(C)c(C)c1]
R1-18
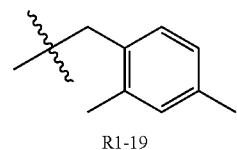 [SMILES: *Cc1ccc(C)cc1C]
R1-19
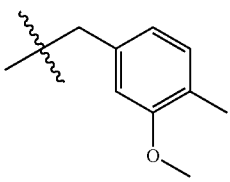
R1-20
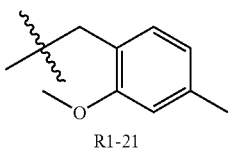
R1-21
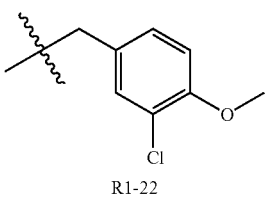 [SMILES: *Cc1ccc(OC)c(Cl)c1]
R1-22
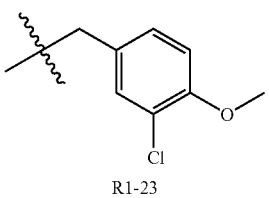 [SMILES: *Cc1ccc(OC)c(Cl)c1]
R1-23
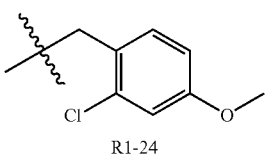 [SMILES: *Cc1ccc(OC)cc1Cl]
R1-24
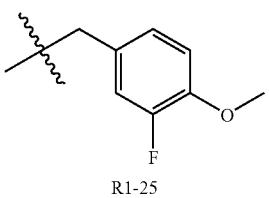 [SMILES: *Cc1ccc(OC)c(F)c1]
R1-25
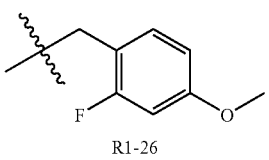
R1-26
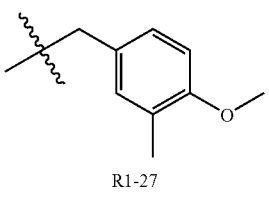 [SMILES: *Cc1ccc(OC)c(C)c1]
R1-27
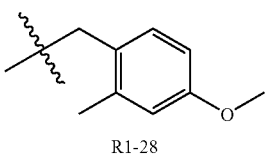
R1-28
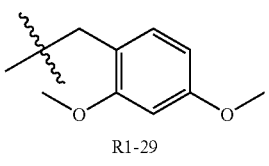 [SMILES: *Cc1ccc(OC)cc1OC]
R1-29
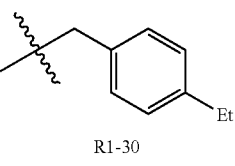 [SMILES: *Cc1ccc(CC)cc1]
R1-30
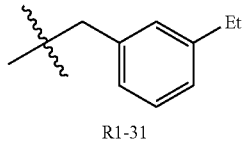 [SMILES: *Cc1cccc(CC)c1]
R1-31
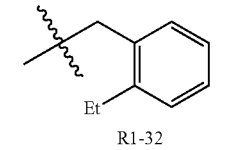 [SMILES: *Cc1ccccc1CC]
R1-32
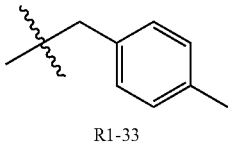 [SMILES: *Cc1ccc(C)cc1]
R1-33
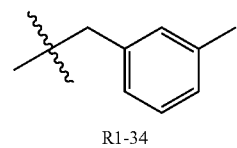 [SMILES: *Cc1cccc(C)c1]
R1-34
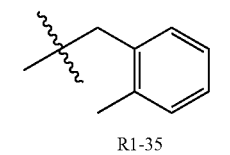 [SMILES: *Cc1ccccc1C]
R1-35
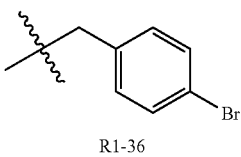 [SMILES: *Cc1ccc(Br)cc1]
R1-36
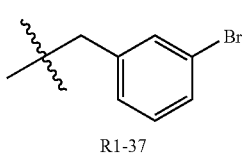 [SMILES: *Cc1cccc(Br)c1]
R1-37
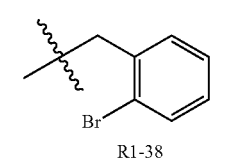 [SMILES: *Cc1ccccc1Br]
R1-38
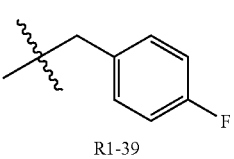 [SMILES: *Cc1ccc(F)cc1]
R1-39

TABLE 2a-continued
R1 moieties of Formula II-a include, but are not limited to, the following:
Illustrative R1 moieties
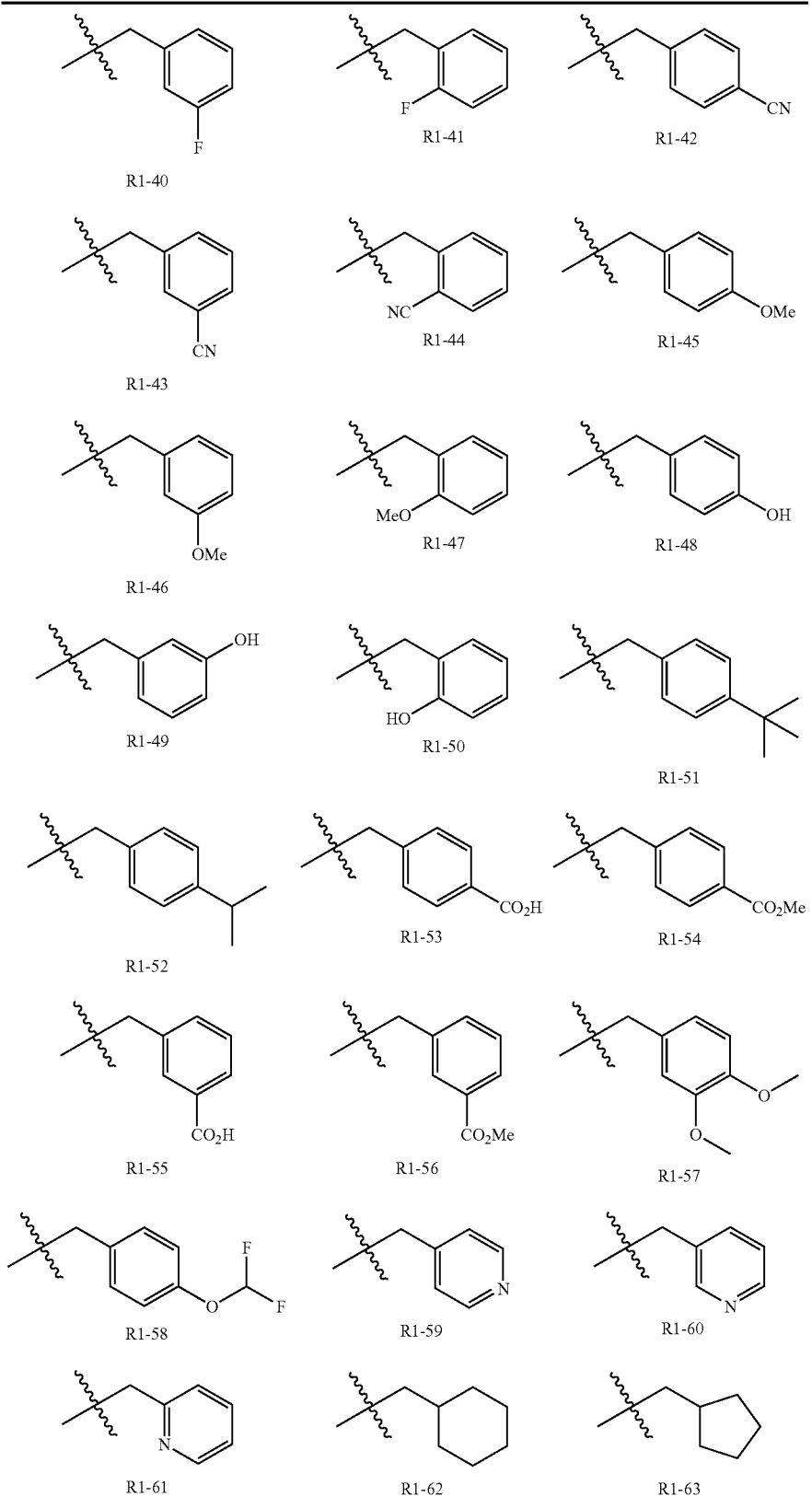

TABLE 2a-continued

R₁ moieties of Formula II-a include, but are not limited to, the following:
Illustrative R₁ moieties R1-64, R1-65, R1-66, R1-67, R1-68, R1-69, R1-70, R1-71, R1-72, R1-86, R1-74, R1-75, R1-76, R1-77, R1-78, R1-79, R1-80, R1-81

TABLE 2a-continued
R$_1$ moieties of Formula II-a include, but are not limited to, the following:
Illustrative R$_1$ moieties
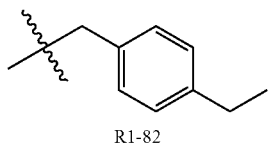 [SMILES: *Cc1ccc(CC)cc1]
R1-82
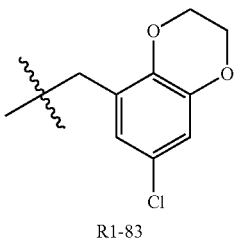 [SMILES: *Cc1cc(Cl)cc2c1OCCO2]
R1-83
TABLE 2b
R$_3$ moieties of the compounds of Formula II-a include, but are not limited to, the following:
Exemplary·R$_3$¤
—H
R3-1
—OH
R3-2
—OCH$_2$CH$_2$NMe$_2$
R3-3
—OCH$_2$CH$_2$NEt$_2$
R3-4
—OCH$_2$CH$_2$CH$_2$NMe$_2$
R3-5
—O(CH$_2$)$_3$NEt$_2$
R3-6
R3-7
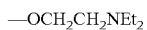
R3-8
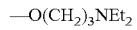
R3-9
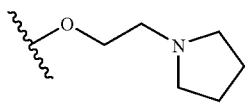
R3-10
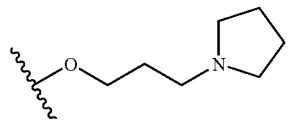
R3-11
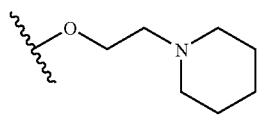
R3-12
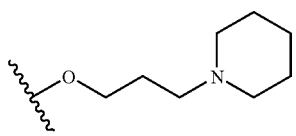
R3-13
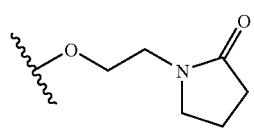
R3-14
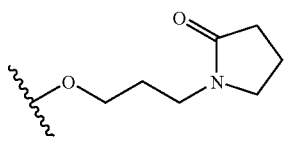
R3-15¤
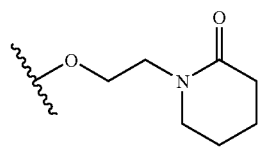
R3-16
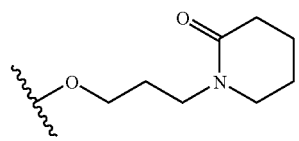
R3-17
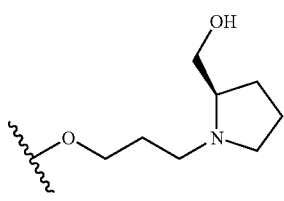
R3-18
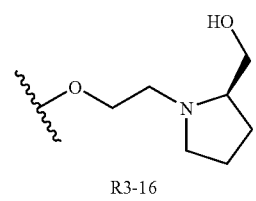 [SMILES: *OCCN1CCC[C@@H]1CO]
R3-19
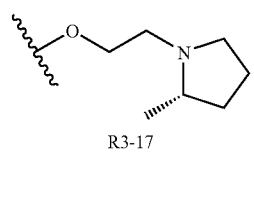 [SMILES: *OCCN1CCC[C@@H]1C]
R3-20

TABLE 2b-continued
R₃ moieties of the compounds of Formula II-a include, but are not limited to, the following:
Exemplary·R₃
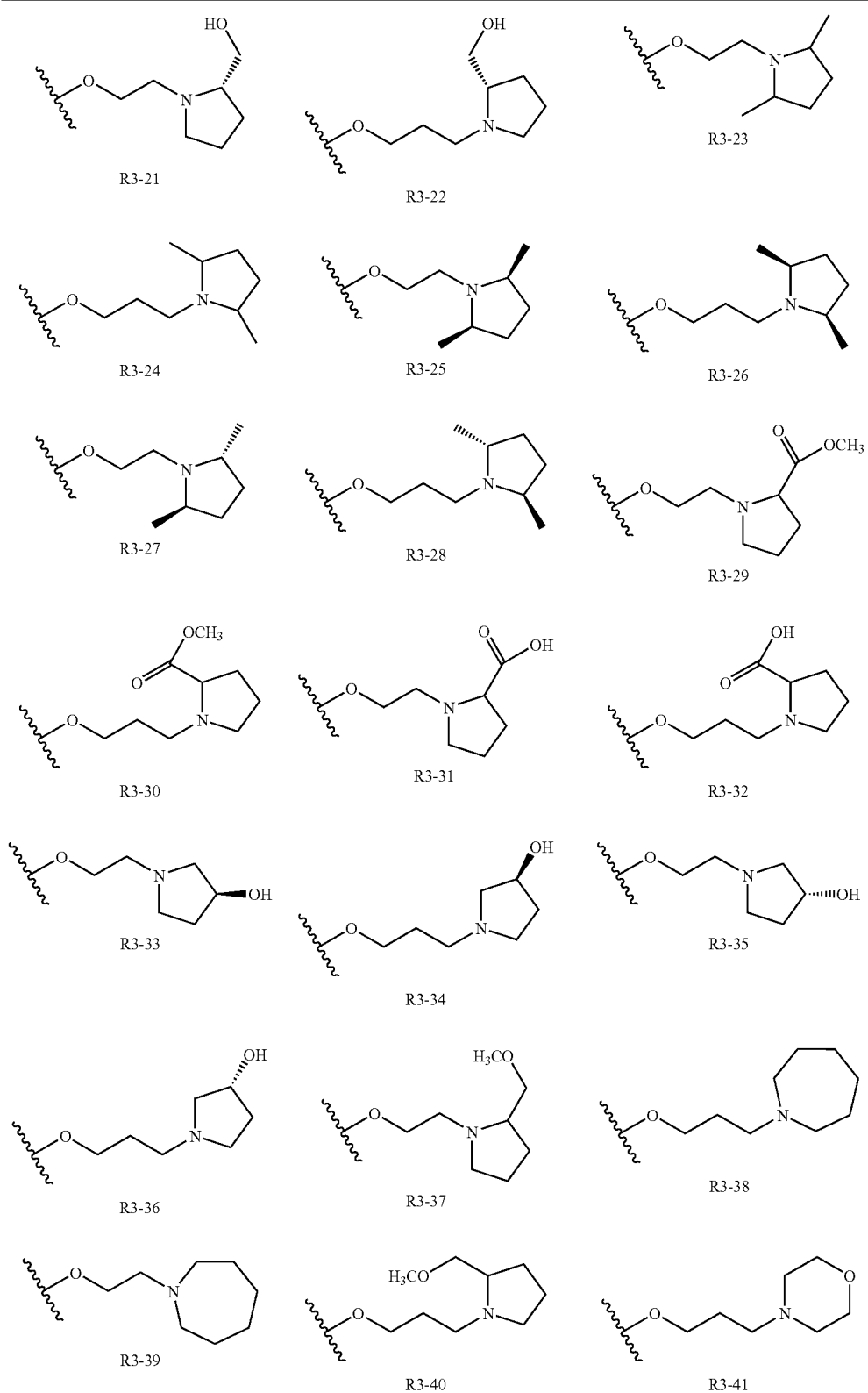

TABLE 2b-continued

R₃ moieties of the compounds of Formula II-a include, but are not limited to, the following:

Exemplary·R₃¤

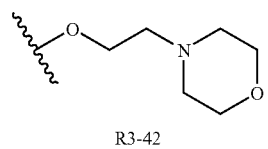 [SMILES: *OCCN1CCOCC1]

R3-42

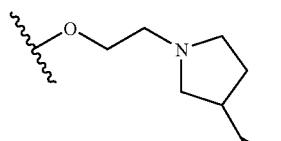

R3-43

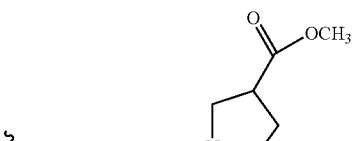

R3-44

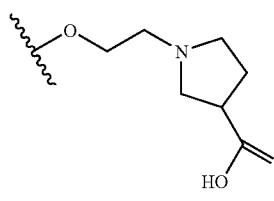

R3-45

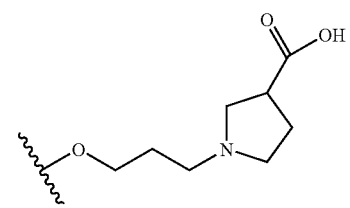

R3-46

TABLE 2c

Each of the R₄, R₅, R₆, and R₇ moieties of the compounds of
Formula II-a include, but are not limited to, the following:
Illustrative R₄, R₅, R₆, and R₇ Moieties

| | | |
|---|---|---|
| hydrogen | methyl | ethyl |
| R4-1 | R4-2 | R4-3 |
| chloro | fluoro | bromo |
| R4-4 | R4-5 | R4-6 |
| hydroxy | —OMe | —NO₂ |
| R4-7 | R4-8 | R4-9 |
| —NH₂ | —NHCOCH₃ | —NHCOCH(CH₃)₂ |
| R4-10 | R4-11 | R4-12 |
| —NHCOCF₃ | —NHCOPh | —NHCONHC₄H₉ |
| R4-13 | R4-14 | R4-15 |
| —N(Et)₂ | —NHSO₂Me | —NHSO₂CF₃ |
| R4-16 | R4-17 | R4-18 |

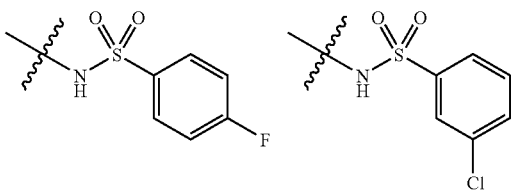

| | | —SO₂Me |
| | | R4-21 |
|---|---|---|
| —CN | R₄ and R₅ are | R₅ and R₆ are |
| R4-21 | R4-22 | R4-23 |
| R₆ and R₇ are | R₆ and R₇ are | R₄ and R₅ are |
| —CH₂O— | —OCH₂CH₂O— | —OCH₂CH₂O— |
| R4-25 | R4-26 | R4-27 |
| R₆ and R₇ are | —CO₂H | —CF₃ |
| —OCH₂CH₂O— | R4-29 | R4-30 |
| R4-28 | | |
| —OEt | —SO₂NH₂ | —SO₂NHMe |
| R4-31 | R4-32 | R4-33 |
| SO₂NMe₂ | SO₂NMe₂ | NHC(O)Me |
| R4-34 | R4-35 | R4-36 |
| —NHC(O)Ph | —NMeC(O)Et | —NMeC(O)Ph |
| R4-36 | R4-37 | R4-38 |
| —C(O)NHMe | —C(O)NEt₂ | —C(O)NH₂ |
| R4-39 | R4-40 | R4-41 |
| —NHC(O)NHMe | —CO₂Me | |
| R4-42 | R4-43 | |

Formula II-b

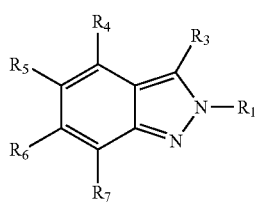

Some non-limiting illustrative compounds of the present invention having a structure of Formula II-b include those in which $R_1$ is any $R_1$ moiety described in Table 2d, in combination with any $R_3$ moiety described in Table 2e, and any $R_4$, $R_5$, $R_6$, and $R_7$ as described in Table 2f. A compound of Formula II-b includes any combination of $R_1$, $R_3$, $R_4$, $R_5$, $R_6$, and $R_7$. Additional exemplary compounds of Formula II-b are illustrated in Tables 3, 4, and 5.

TABLE 2d $R_1$ moieties of Formula II-b include, but are not limited to, the following:
Illustrative $R_1$ moieties

| hydrogen | methyl | ethyl |
| R1-1 | R1-2 | R1-3 |

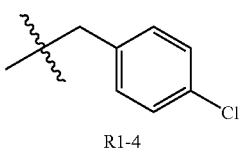 [SMILES: *Cc1ccc(Cl)cc1]
R1-4

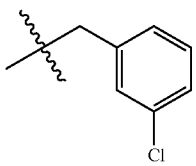
R1-5

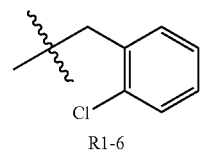 [SMILES: *Cc1ccccc1Cl]
R1-6

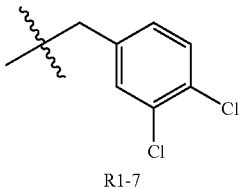 [SMILES: *Cc1ccc(Cl)c(Cl)c1]
R1-7

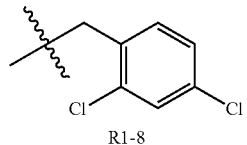 [SMILES: *Cc1ccc(Cl)cc1Cl]
R1-8

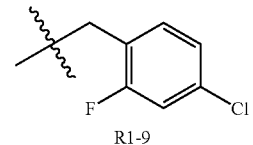 [SMILES: *Cc1ccc(Cl)cc1F]
R1-9

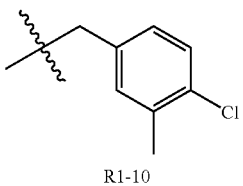 [SMILES: *Cc1ccc(Cl)c(C)c1]
R1-10

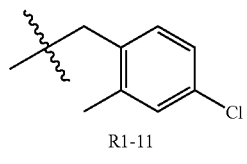 [SMILES: *Cc1ccc(Cl)cc1C]
R1-11

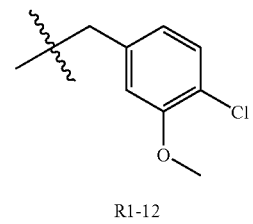 [SMILES: *Cc1ccc(Cl)c(OC)c1]
R1-12

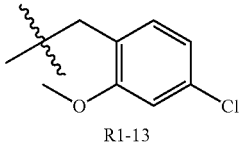 [SMILES: *Cc1ccc(Cl)cc1OC]
R1-13

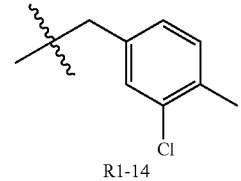 [SMILES: *Cc1ccc(C)c(Cl)c1]
R1-14

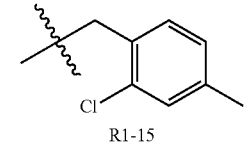 [SMILES: *Cc1ccc(C)cc1Cl]
R1-15

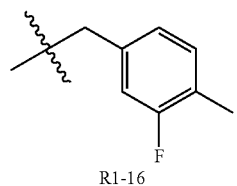 [SMILES: *Cc1ccc(C)c(F)c1]
R1-16

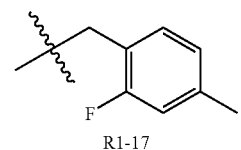 [SMILES: *Cc1ccc(C)cc1F]
R1-17

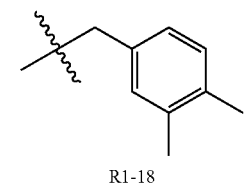 [SMILES: *Cc1ccc(C)c(C)c1]
R1-18

TABLE 2d-continued
R₁ moieties of Formula II-b include, but are not limited to, the following:
Illustrative R₁ moieties
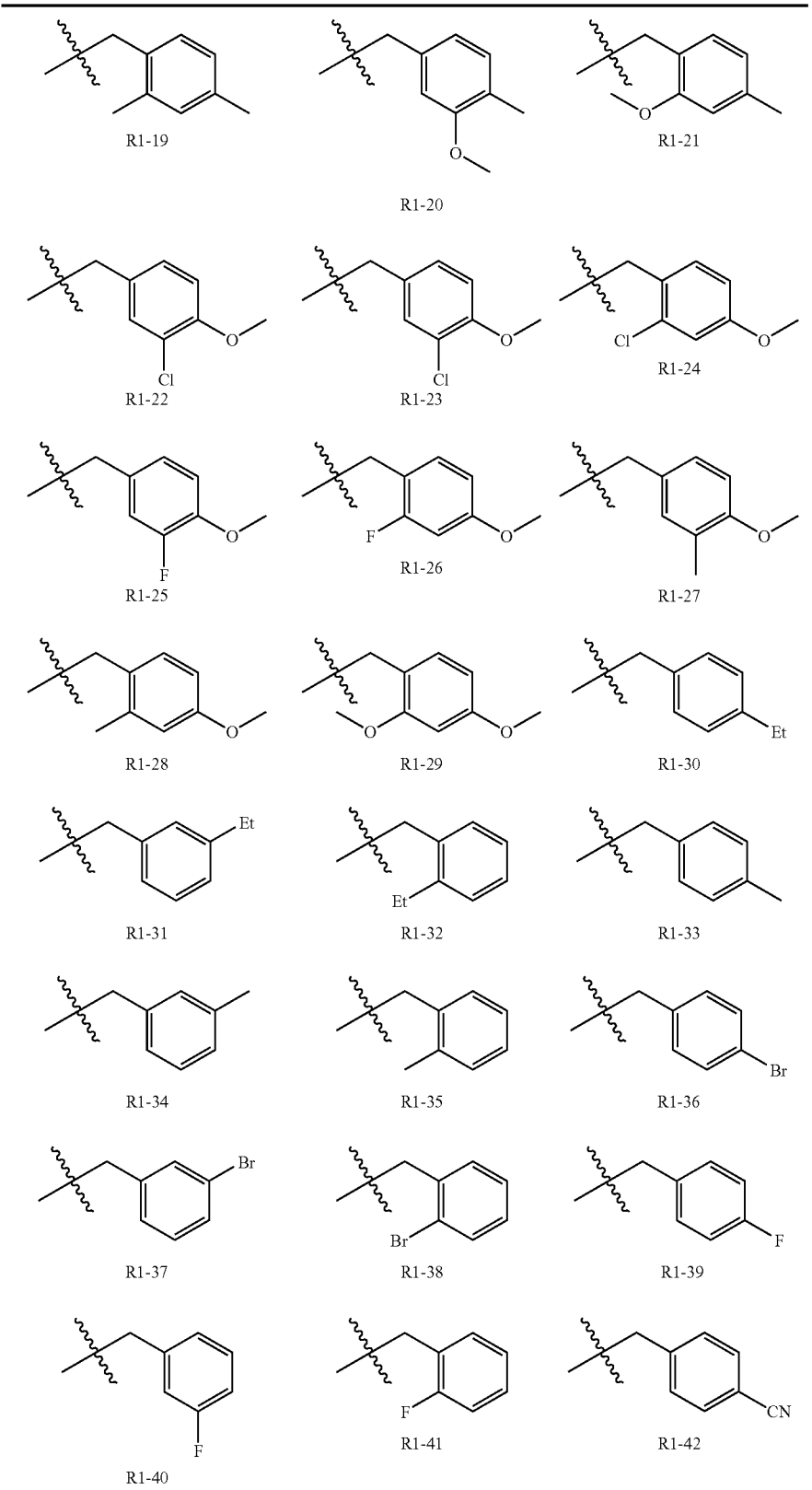

TABLE 2d-continued
R₁ moieties of Formula II-b include, but are not limited to, the following:
Illustrative R₁ moieties
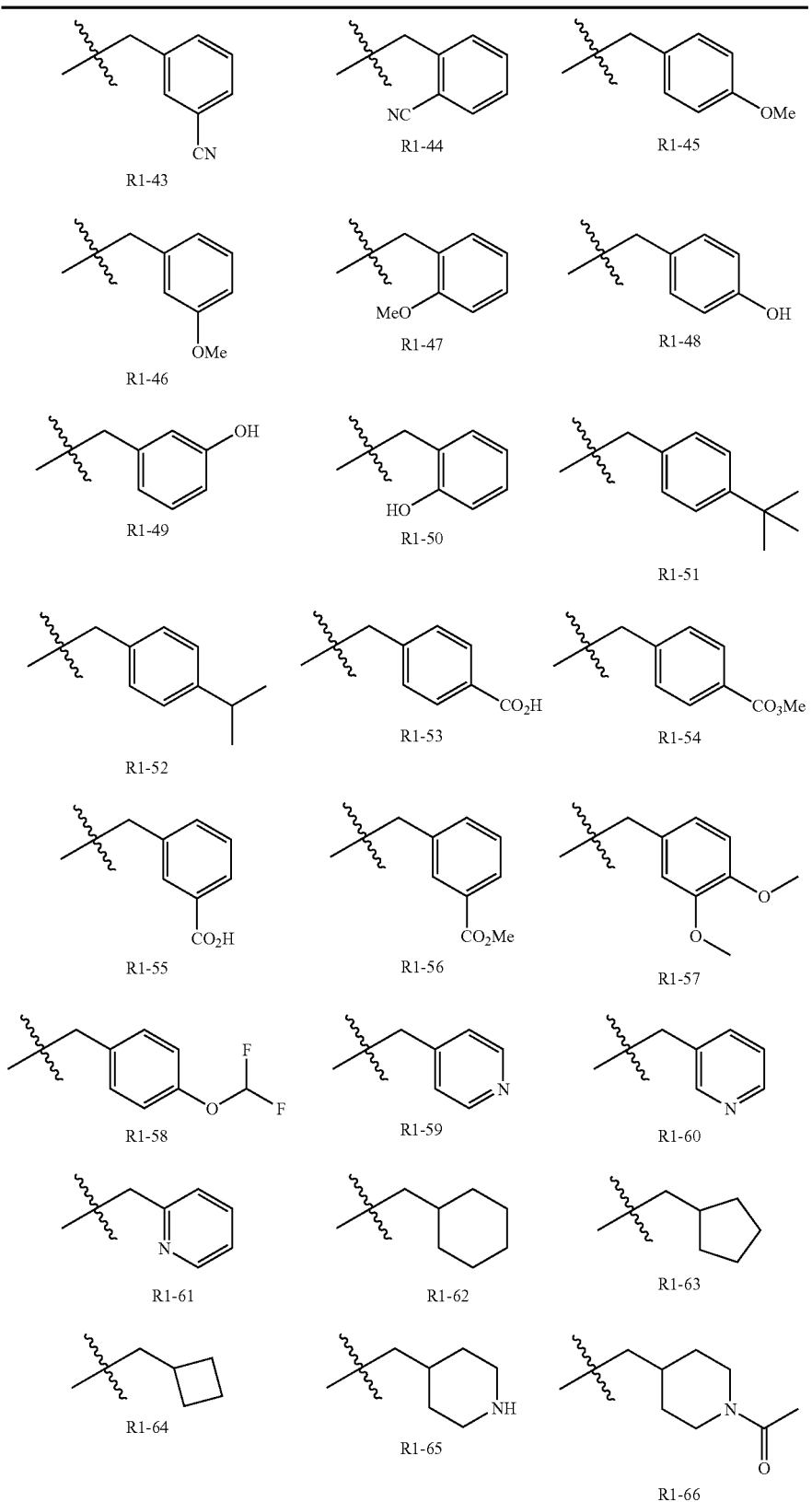

TABLE 2d-continued
R₁ moieties of Formula II-b include, but are not limited to, the following:
Illustrative R₁ moieties
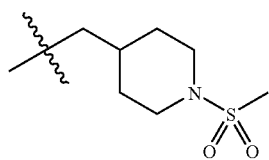
R1-67
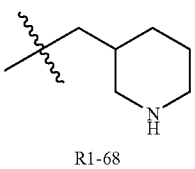 [SMILES: *CC1CCCNC1]
R1-68
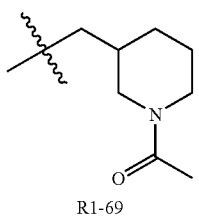 [SMILES: *CC1CCCN(C(C)=O)C1]
R1-69
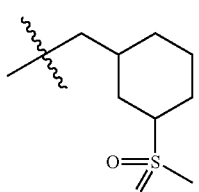
R1-70
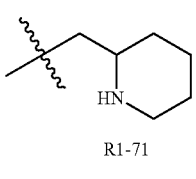 [SMILES: *CC1CCCCN1]
R1-71
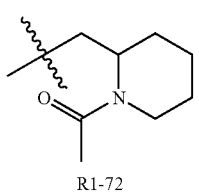 [SMILES: *CC1CCCCN1C(C)=O]
R1-72
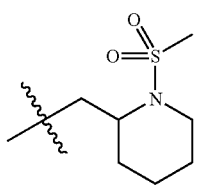
R1-73
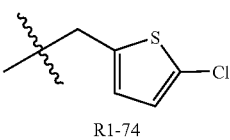 [SMILES: *Cc1ccc(Cl)s1]
R1-74
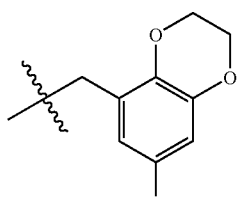
R1-75
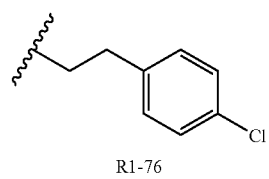 [SMILES: *CCc1ccc(Cl)cc1]
R1-76
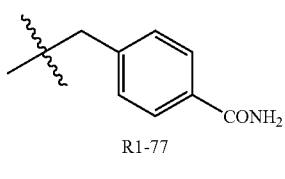 [SMILES: *Cc1ccc(C(N)=O)cc1]
R1-77
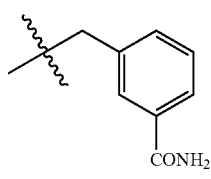
R1-78
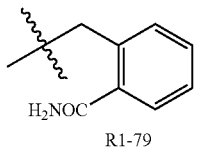 [SMILES: *Cc1ccccc1C(N)=O]
R1-79
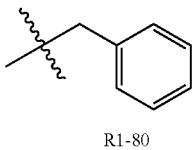 [SMILES: *Cc1ccccc1]
R1-80
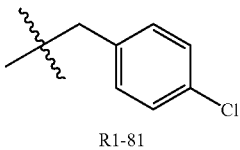 [SMILES: *Cc1ccc(Cl)cc1]
R1-81
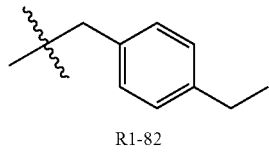 [SMILES: *Cc1ccc(CC)cc1]
R1-82
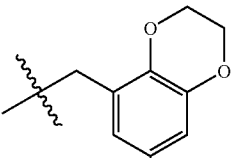
R1-83

TABLE 2e

R₃ moieties of the compounds of Formula II-b include, but are not limited to, the following:
Exemplary R₃

| —H | —OH | —OCH₂CH₂NMe₂ |
|---|---|---|
| R3-1 | R3-2 | R3-3 |
| —OCH₂CH₂NEt₂ | —OCH₂CH₂CH₂NMe₂ | —O(CH₂)₃NEt₂ |
| R3-4 | R3-5 | R3-6 |

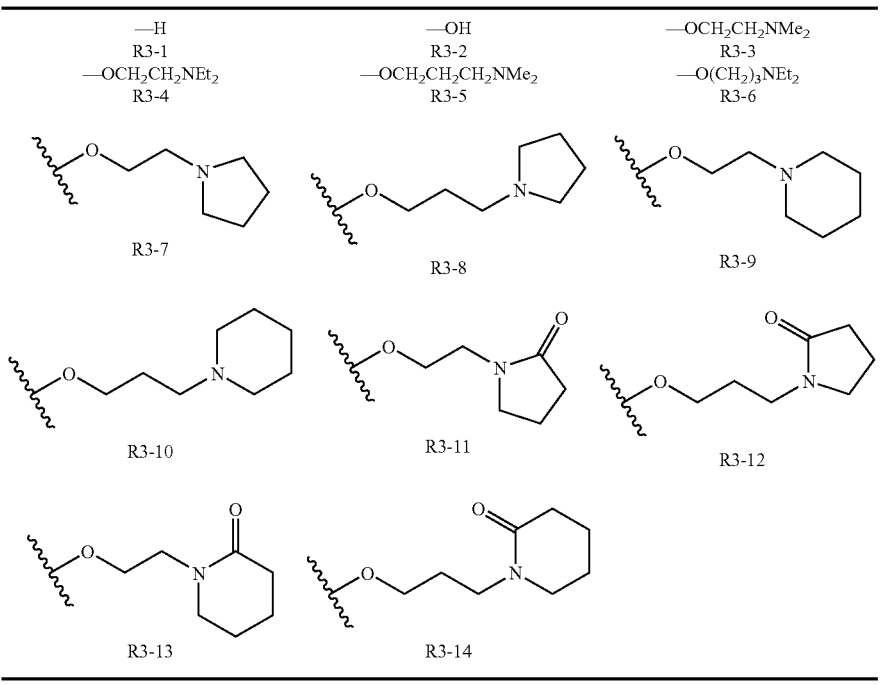

R3-7, R3-8, R3-9, R3-10, R3-11, R3-12, R3-13, R3-14

TABLE 2f

Each of the R₄, R₅, R₆, and R₇ moieties of the compounds of Formula II-b include, but are not limited to, the following:
Illustrative R₄, R₅, R₆, and R₇ Moieties

| hydrogen | methyl | ethyl |
|---|---|---|
| R4-1 | R4-2 | R4-3 |
| chloro | fluoro | bromo |
| R4-4 | R4-5 | R4-6 |
| hydroxy | —OMe | —NO₂ |
| R4-7 | R4-8 | R4-9 |
| —NH₂ | —NHCOCH₃ | —NHCOCOCH(CH₃)₂ |
| R4-10 | R4-11 | R4-12 |
| —NHClCF₃ | —NHCOPh | —NHCONHC₄H₉ |
| R4-13 | R4-14 | R4-15 |
| —N(Et)₂ | —NHSO₂Me | —NHSO₂CF₃ |
| R4-16 | R4-17 | R4-18 |

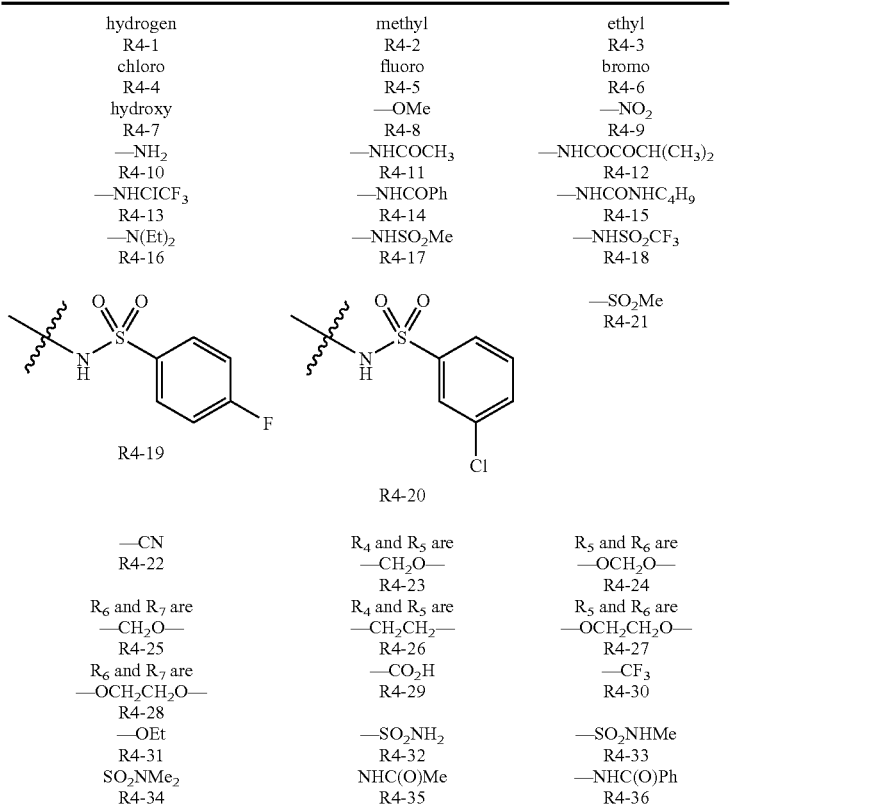

| | | —SO₂Me |
|---|---|---|
| | | R4-21 |
| R4-19 | R4-20 | |
| —CN | R₄ and R₅ are | R₅ and R₆ are |
| R4-22 | —CH₂O— | —OCH₂O— |
| | R4-23 | R4-24 |
| R₆ and R₇ are | R₄ and R₅ are | R₅ and R₆ are |
| —CH₂O— | —CH₂CH₂— | —OCH₂CH₂O— |
| R4-25 | R4-26 | R4-27 |
| R₆ and R₇ are | —CO₂H | —CF₃ |
| —OCH₂CH₂O— | R4-29 | R4-30 |
| R4-28 | | |
| —OEt | —SO₂NH₂ | —SO₂NHMe |
| R4-31 | R4-32 | R4-33 |
| SO₂NMe₂ | NHC(O)Me | —NHC(O)Ph |
| R4-34 | R4-35 | R4-36 |

TABLE 2f-continued

Each of the $R_4$, $R_5$, $R_6$, and $R_7$ moieties of the compounds of Formula II-b include, but are not limited to, the following:
Illustrative $R_4$, $R_5$, $R_6$, and $R_7$ Moieties

| | | |
|---|---|---|
| —NMeC(O)Et | —NMeC(O)Ph | —C(O)NHMe |
| R4-37 | R4-38 | R4-39 |
| —C(O)NEt$_2$ | —C(O)NH$_2$ | —NHC(O)NHMe |
| R4-40 | R4-41 | R4-42 |
| —CO$_2$Me | | |
| R4-43 | | |

Embodiments of the present invention include prodrugs of the compounds of Formula II-a or II-b.

The compounds provided herein as viral inhibiting agents are generally capable of inhibiting viral replication in vitro and/or in vivo. For example a compound of the present invention when contacted with an HCV-infected cell (e.g., an HCV-infected liver cell), reduces the amount of infectious HCV viral particles produced by the HCV-infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or even higher, compared to the number of infectious HCV viral particles produced by the cell not contacted with the inhibiting agent.

A wide variety of methods are available to assess whether a compound can reduce viral load in vitro and/or in vivo. In vitro assay typically determines the number of viral particles present in the culture medium, wherein an in vivo assay typically measures the viral titer present in a bodily fluid of an infected subject. Bodily fluids suitable for viral titer measurement include but are not limited to blood, serum, plasma, saliva, semen, spinal fluid, urine, sweat, and cerebral spinal fluid. Commonly employed methods for detecting viral load in vitro or in vivo include quantitative polymerase chain reaction (PCR) and branched DNA (bDNA) test. Numerous quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

The compounds provided herein can also be characterized by their ability to inhibit binding of NS4B polypeptide to the 3'UTR of HCV negative strand RNA by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or higher, compared to the binding of NS4B polypeptide to the 3'UTR of HCV negative strand RNA in the absence of the compound.

In some embodiments, the inhibiting agents of the present invention inhibit binding of NS4B polypeptide to the 3'UTR of HCV negative strand RNA (SEQ ID NO: 1) with a 50% inhibitory concentration (IC$_{50}$) of about 100 µM to 50 µM, about 50 µM to 25 µM, about 25 µM to 10 µM, about 10 µM to 5 µM, about 5 µM to 1 µM, about 1 µM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, less than about 5 nM, less than about 1 nM, less than about 0.1 nM, or less than about 0.01 nM.

In other embodiments, the inhibiting agents of the present invention lack substantial cross-reactivity with HERG K$^+$ channel. Drug-induced cardiac arrhythmia, such as QT prolongation, is a serious safety concern in the discovery, development and use of new medications. Drug-induced QT interval prolongation is an active field of research and has been reviewed (Pearlstein et al. *J. Med. Chem.* (2003), 46(11): 2017-2022; Fermini et al., *Annual Reports in Medicinal Chemistry* (2004), 39:323; http://www.qtdrugs.org). A common cause of QT prolongation is the inhibition of the cardiac HERG K$^+$ channel by a drug. Drugs from widely different chemical classes and therapeutic utility have been shown to block HERG activity. Many medications known to be HERG channel inhibitors interact with the channel at concentrations similar to the desired therapeutic concentration. One strategy to prevent the occurrence of drug-induced QT interval prolongation is to select drug candidates that show a reduced affinity for the HERG K$^+$ channel. This property can be characterized by an in vitro assay utilizing HEK293 or CHO cells stably transfected with the hERG gene and utilizing a patch-clamp technique to determine Ikr current. Accordingly, some preferred inhibiting agents of the present invention exhibit reduced affinity for or lack substantial cross-reactivity with the HERG K$^+$ channel. In one aspect, an exemplary inhibiting agent of the present invention has a HERG IC$_{50}$ of greater than about 100 nM. In another aspect, the inhibiting agent described herein has a HERG IC$_{50}$ of greater than about 500 nM, 1,000 nM, 5,000 nM, 1 µM, 5 µM, 10 µM, 50 µM, 100 µM or even higher.

Methods of Synthesis

In general, the inhibiting agents provided herein including clemizole, clemizole analogs, isosteres thereof can be made according to organic synthesis techniques known to those skilled in this art and/or according to the synthesis schemes provided herein. Where desired, synthesis of the subject compound begins with commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.). In addition, Methods known to one of ordinary skill in the art may be identified through various reference books and databases. Suitable reference books and treatises that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes. Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Aldrich Chemical Company (Milwaukee, Wis.) or can be readily prepared by those skilled in the art using commonly employed synthetic methodology.

The compounds of the invention can be synthesized by an appropriate combination of known synthetic methods in the art and the instant disclosure. The discussion below is offered to illustrate certain of the diverse methods available for use in making the compounds of the invention and is not intended to limit the scope of reactions or reaction sequences that can be used in preparing the compounds of the present invention.

Compounds of the invention can be prepared by the O-alkylation of 1-substituted-benzyl-1H-indazol-3(2H)-one 1.1 with $R_{11}X$ (X=Cl, Br, I, OMs, OTs, and the like), as described in Scheme 1.

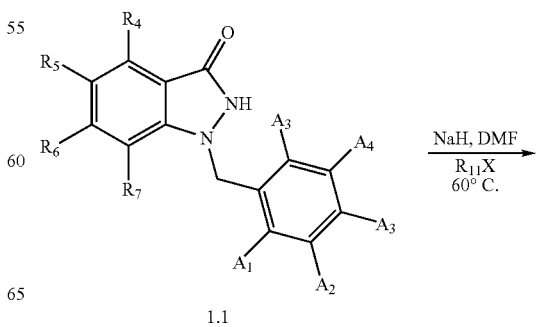

Scheme 1

-continued

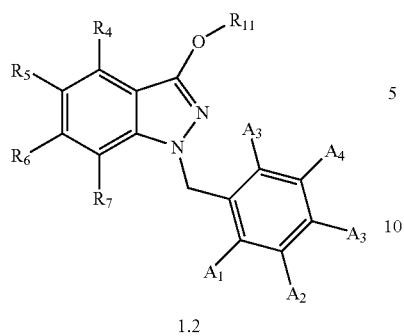

1.2

Scheme 2 illustrates a general method for the synthesis of 1-substituted-benzyl-1H-indazol-3(2H)-ones 2.3 by the N-alkylation of 1H-indazol-3(2H)-one 2.1 with substituted benzyl electrophiles 2.2 (X=Cl, Br, I, OMs, OTs, and the like).

Scheme 2

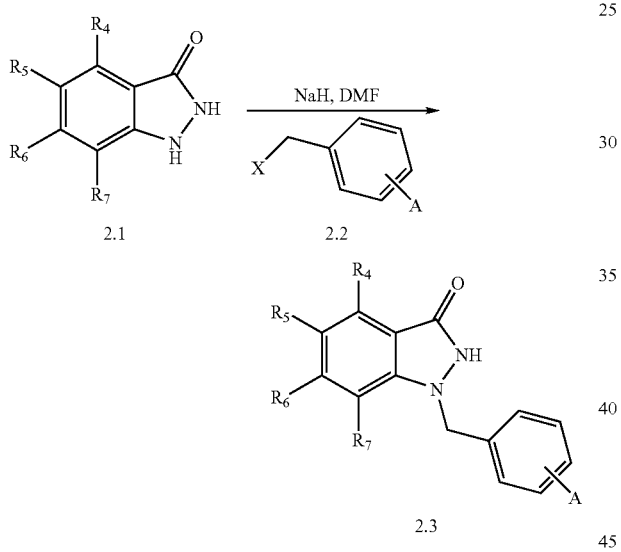

Scheme 3 illustrates the synthesis of compounds of the invention. 3-indazolinone 3.1 can be alkylated in high yields by treatment with NaOH in EtOH, followed by treatment with a substituted benzyl halide to provide 3.2 (Japanese Patent JP49007278). Deprotonation followed by alkylation with a protected bromo-alcohol provides 3.3. Deprotection of the alcohol followed by activation and displacement with primary and secondary amines and/or alkoxides provides 3.4.

Scheme 3

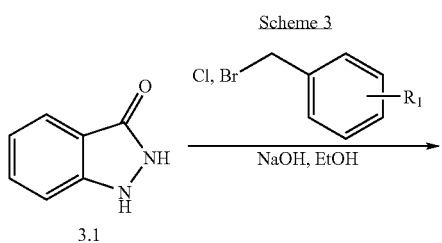

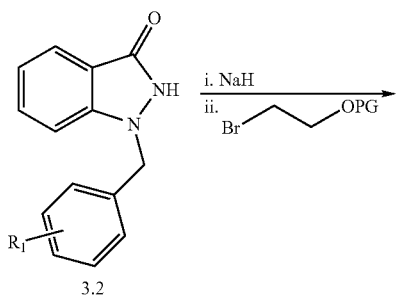

3.2

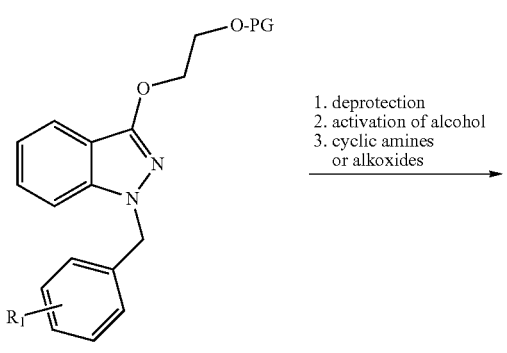

3.3

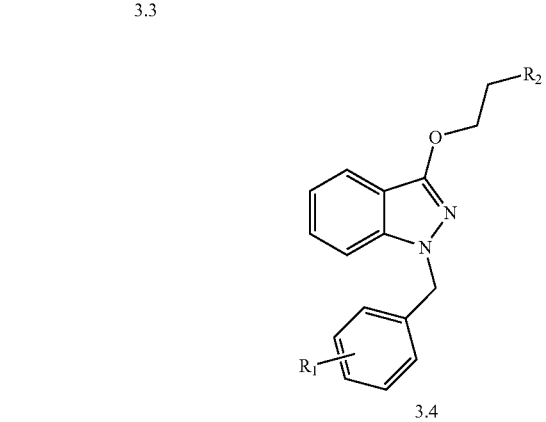

3.4

Scheme 4 illustrates a method for the synthesis of compounds of the invention. Treatment of 3-indazilinone 4.1 with PBu$_3$ and diazodipiperidinylamide provides ether 4.2. Deprotonation with NaH followed by alkylation provides compounds of general structure 4.3.

Scheme 4

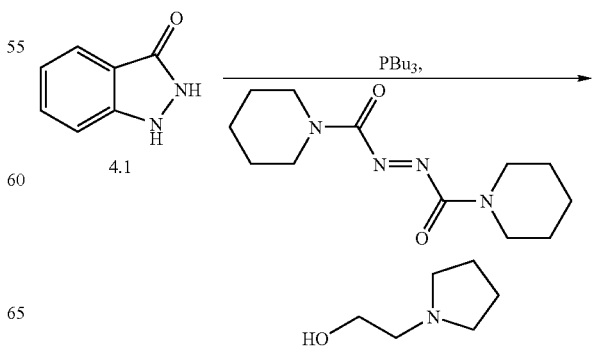

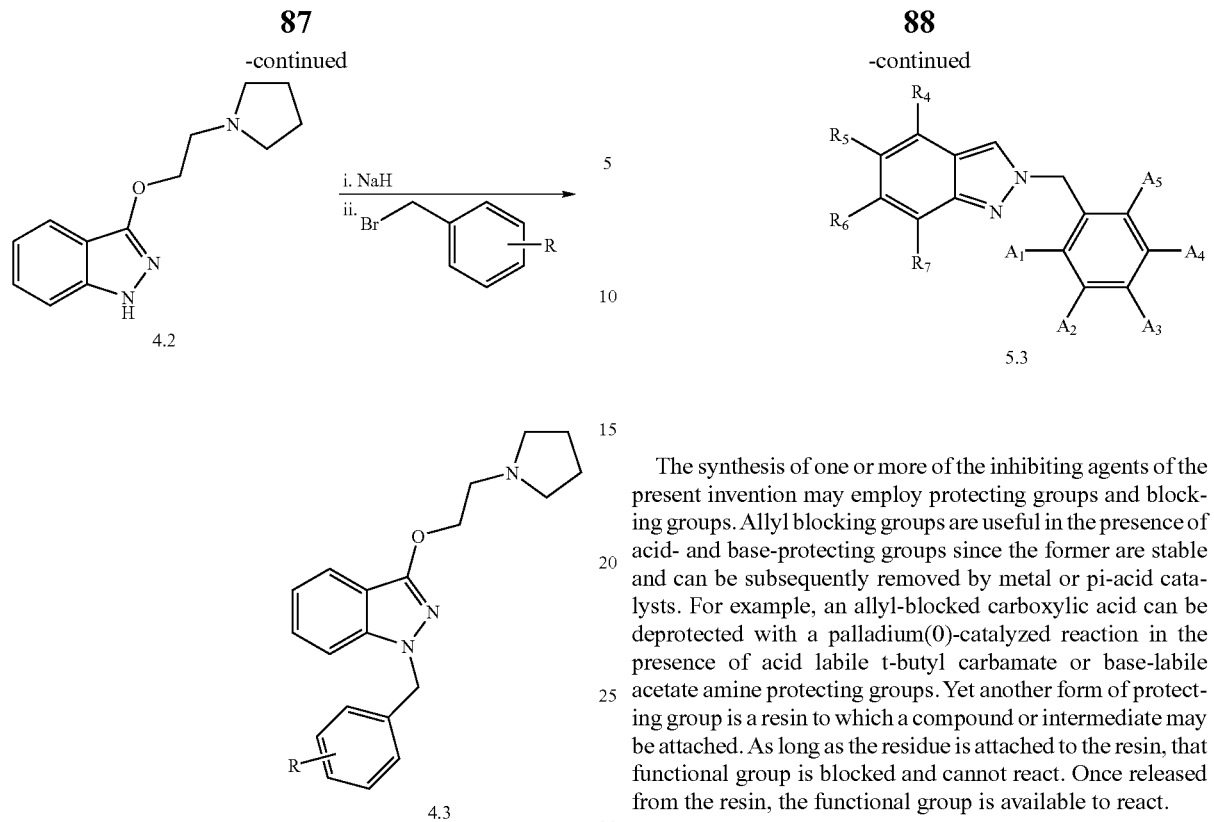

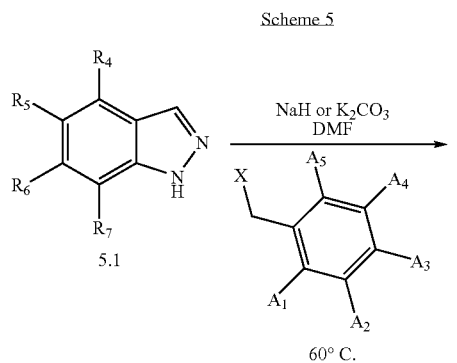

Scheme 5 illustrates the synthesis of 1- or 2-(substituted-benzyl)-indazole 5.2 and 5.3 by the alkylation of indazole 5.1 with benzyl halide (X=Cl, Br, I, OMs, OTs, and the like).

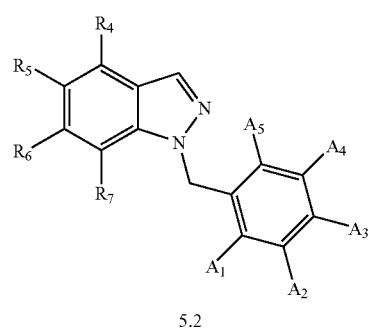

The synthesis of one or more of the inhibiting agents of the present invention may employ protecting groups and blocking groups. Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to, the following moieties.

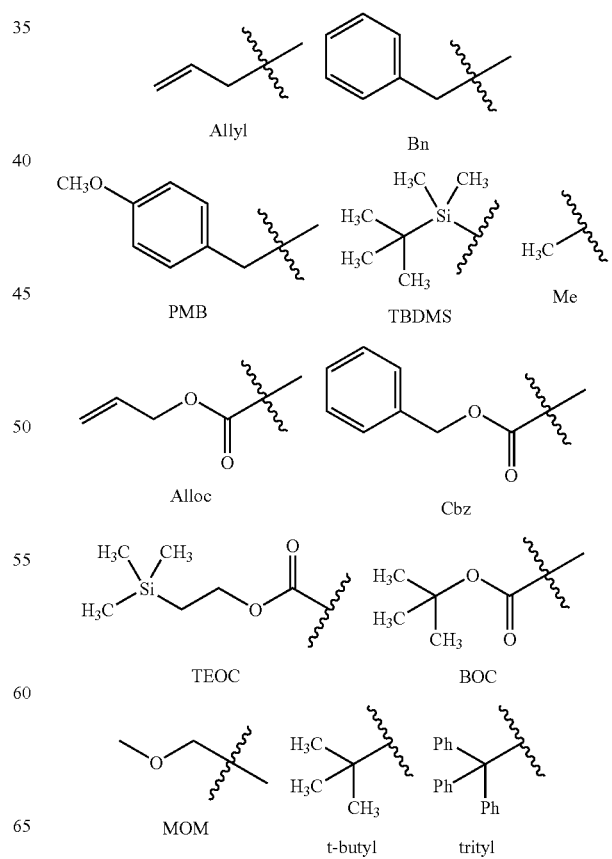

-continued

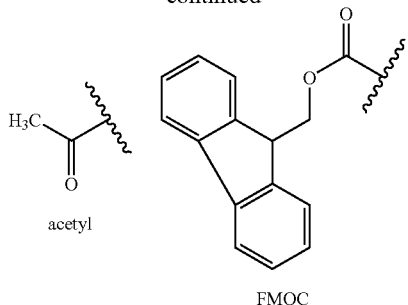

acetyl    FMOC

Pharmaceutical Formulations and Routes of Administration

The present invention provides pharmaceutical compositions comprising one or more inhibiting agents disclosed herein with or without pharmaceutically acceptable excipients, diluents, carriers and/or adjuvants. In some embodiment, the pharmaceutical compositions are formulated to be substantially free of excipients. In other embodiments, inhibiting agents can be formulated with one or more pharmaceutically acceptable auxiliary substances.

In an embodiment, the inhibiting agent can be combined with another anti-viral agent to prepare a composition of the invention, and the composition can include one or more pharmaceutically acceptable excipients, diluents, carriers and/or adjuvants.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the inhibiting agent is administered to the host using any means capable of resulting in the desired effect (e.g., reduction in viral load, reduction in liver fibrosis, increase in liver function, and the like). Thus, the inhibiting agent can be incorporated into a variety of formulations for therapeutic administration. For example, the inhibiting agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the inhibiting agent may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the inhibiting agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the inhibiting agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the inhibiting agent can be utilized in aerosol formulation to be administered via inhalation. Embodiments of the inhibiting agent can be formulated into pressurized acceptable propellants such as dichlorodifluoromethane, propane, nitrogen, and the like.

Furthermore, embodiments of the inhibiting agent can be made into suppositories by mixing with a variety of bases such as emulsifying bases or water-soluble bases. Embodiments of the inhibiting agent can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the inhibiting agent in a composition as a solution in sterile water, normal saline or another pharmaceutically acceptable carrier.

Embodiments of the inhibiting agent can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (inhibiting agent) encapsulated in liposome vehicles in accordance with the invention.

In an embodiment, the inhibiting agent is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725, 852; 5,820,589; 5,643,207; 6,198,966; and the like. In general, delivery of the inhibiting agent can be accomplished using any of a variety of refillable, pump systems. Pumps provide consistent, controlled release over time. In some embodiments, the inhibiting agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, and the like.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the inhibiting agent adequate to achieve the desired state in the subject being treated.

Compositions of the present invention include those that comprise a sustained-release or controlled release matrix. In addition, embodiments of the present invention can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. Similarly, the sustained release formulations of embodiments of the invention can help maintain viral-inhibiting concentrations over a longer time interval.

In another embodiment, the pharmaceutical composition of the present disclosure (as well as combination compositions) are delivered in a controlled release system. For example, the inhibiting agent may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present invention (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The inhibiting agents disclosed herein can be formulated in a pharmaceutical composition comprising an effective amount of the inhibiting agent for its intended use. For example, an isostere of a benzimidazole core structure of the present invention can be formulated in a unit dose form between about 10 mg to about 500 mg for treating viral infections, especially infections by a virus of the Flaviviridae family. In some embodiments, an isostere of a benzimidazole core structure of the present invention is formulated in a unit dose form between about 25 mg to about 250 mg, between about 25 mg to about 100 mg, or between about 50 mg to about 100 mg. In particular, an isostere of a benzimidazole core structure can be formulated in 25 mg, 50 mg, 75 mg, 100 mg, 125 mg, 150 mg or 200 mg unit dose form. In one embodiment, the unit dose form is a tablet; in another, the unit dose form is a capsule. The tablet can be formulated as immediate release dose form or as sustained release form. In yet another embodiment, the unit dose form is a liquid.

Uses of the Compounds and Pharmaceutical Compositions of the Present Invention

The subject compounds and pharmaceutical compositions thereof are particularly useful for treating infection by a virus of the Flaviviridae family. The treatment methods typically comprise administering to a subject infected with such virus a therapeutically effective amount of an inhibiting agent in one or more doses. For subjects already infected with a virus of the Flaviviridae family such as Hepatitis Virus C, the method of the present invention is generally effective in reducing the viral load over a period of a few days, a few weeks or a few months.

The present invention also provides methods of prophylactically treating an infection by a virus of the Flaviviridae family of viruses comprising administering an effective amount of an inhibiting agent described herein to a subject in need thereof. Prophylactic treatment of infection by a virus of the Flaviviridae family (including but not limited to HCV) is particularly important for patients who will be undergoing liver transplantation for HCV-associated end stage liver disease (ESLD). It has been reported that the new graft is nearly certain to be infected with HCV if viremia is present at the time of transplantation. Prophylactic treatment with clemizole or clemizole analogs or the isosterers thereof can be performed to reduce or eliminate HCV viral load prior to liver transplantation, and can help prevent the recurrence of HCV after transplantation. The administration of clemizole, clemizole analogs, or isosterers of the present invention may also be advantageous for patients who cannot tolerate full doses of standard of care therapy (pegylated interferon and ribavirin). Where desired, for pre-transplant patients with ESLD, or post-transplant patients with HCV recurrence, either an isostere monotherapy, or an isostere of the present invention in combination with reduced doses of pegylated interferon and ribavirin, can be used to treat these patients. Similarly, an isostere of a benzimidazole core structure in combination with nitazoxanide (or another thiazolide, or sustained formulations of either of these) can be used to treat these patients, as can indazole plus nitazoxanide (or another thiazolide, or sustained formulations of either of these) plus standard of care medications, at reduced or regular doses, as tolerated.

The inhibiting agent of the present invention and pharmaceutical composition comprising the same can be administered to a subject in one or more doses. In an embodiment, the inhibiting agent can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose.

In an embodiment, the amount of the inhibiting agent per dose is determined on a per body weight basis. For example, in an embodiment, the inhibiting agent can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg per dose, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of the specific inhibiting agent administered, the severity of the symptoms and the susceptibility of the subject to side effects. Preferred dosages for a given compound are readily determinable by those of skill in the art by a variety of means.

In an embodiment, multiple doses of the inhibiting agent are administered. The frequency of administration of the inhibiting agent can vary depending on any of a variety of factors, e.g., severity of the symptoms, and the like. For example, in an embodiment, the inhibiting agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the inhibiting agent is administered continuously.

By way of illustration, efficacious dosing of a compound of the invention can include dosing at about 200 mg po BID, 150 mg po BID, 75 mg po BID, or 50 mg po BID. The total daily dose can also be split among multiple doses, which allows for a lower dose at each administration with less potential for sedation while maintaining sufficient efficacy. Alternatively, a more frequent dosing schedule can be applied for sever cases, for example, TID administration or administration every 4, 6, 8, or 12 hours of a 25 mg, 50 mg, 75 mg, 150 mg or higher dose.

The duration of administration of the inhibiting agent, e.g., the period of time over which the inhibiting agent is administered, can vary, depending on any of a variety of factors, e.g., patient response, and the like. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The practice of a method of the present invention typically involves administering an effective amount of an inhibiting agent or a pharmaceutical composition comprising such inhibiting agent. The specific dose will vary depending on the particular compounds chosen, the dosing regimen to be followed, whether it is administered in combination with other compounds, timing of administration, the tissue to which it is administered, and the physical delivery system in which it is carried. In an embodiment, an effective amount of the inhibiting agent is an amount that, when administered in one or more doses to a host (e.g., human) in need thereof, reduces HCV viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% or more, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

In some embodiments, an effective amount of the inhibiting agent is an amount that, when administered in one or more doses to a host (e.g., human) in need thereof, increases liver function in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the liver function in the individual not treated with the inhibiting agent.

In some embodiments, an effective amount of the inhibiting agent is an amount that, when administered in one or more doses to a host (e.g., a human) in need thereof, reduces liver fibrosis in the host by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the degree of liver fibrosis in the individual not treated with the inhibiting agent.

Liver fibrosis reduction can be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a therapy provided by the invention can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

The subject inhibiting agents and pharmaceutical compositions containing the agents can be used in combination of one or more other therapeutic agents for treating viral infection and other diseases. For example, the inhibiting agents and pharmaceutical formulations provided herein can be employed in combination with other anti-viral agents to treat viral infection. In an embodiment, in accordance with the methods of the present invention, an inhibiting agent that is used to treat a host infected by a Flaviviridae family viral infection is used in combination with one or more other anti-HCV agents to treat HCV infection. In another embodiment, in accordance with the methods of the present invention, an inhibiting agent that prevents the binding of NS4B to the 3'-UTR of HCV RNA (also referred to herein as an "HCV NS4B antagonist") can be used in combination with one or more other anti-HCV agents to treat HCV infection.

In addition, the inhibiting agents and pharmaceutical compositions containing the agents can be used in combination with another agent (e.g. an anti-viral agent) to prophylactically treat an infection with a virus from the Flaviviridae family of viruses including but not limited to HCV. Embodiments of the method involve administering to an individual in need thereof one or more inhibiting agents that inhibit binding of an NS4B polypeptide to the 3'UTR of HCV negative strand RNA.

Current medical practice to treat HCV infection typically employs either interferon-alpha monotherapy or combination therapy with ribavirin (such as Rebetol or Copegus) and either an interferon-alpha (such as interferon alpha 2b) or pegylated interferon (such as Pegasys, marketed by Roche, or PEG-Intron, marketed by Schering Plough). In accordance with the methods of the present disclosure, an inhibiting compound can be used in combination with these standard therapies to treat HCV infection.

A number of HCV protease inhibitors are in development for the treatment of HCV infection, and in accordance with the methods of the present disclosure, co-administration of an inhibiting agent that prevents the binding of NS4B to the 3'-UTR of HCV RNA and an HCV protease inhibitor can be efficacious in the treatment of HCV. In one embodiment, an interferon alpha and/or a nucleoside analog such as ribavirin is/are also employed in this combination therapy. Suitable HCV protease inhibitors include, but are not limited to, telaprevir (VX-950, Vertex), BILN 2061 and BI12202 (Boehringer Ingelheim), boceprevir (SCH 503034, Schering Plough), ITMN191 (Roche/InterMune/Array BioPharma), MK-7009 (Merck), TMC435350 (Tibotec/Medivir), ACH-1095 and ACH-806 (Achillion/Gilead), and other inhibitors of NS3/NS4A protease, including, but not limited to, compounds in development by Presidio.

A number of HCV RNA polymerase (NS5B) inhibitors are in development for the treatment of HCV infection, and in accordance with the methods of the present disclosure, co-administration of an inhibiting agent that prevents the binding of NS4B to the 3'-UTR of HCV RNA and an HCV RNA polymerase inhibitor can be efficacious in the treatment of HCV. In one embodiment, an interferon alpha and/or a nucleoside analog such as ribavirin and/or an HCV protease inhibitor is/are also employed in this combination therapy. Suitable HCV RNA polymerase inhibitors include, but are not limited to, valopicitabine (NM283, Idenix/Novartis), HCV-796 (Wyeth/ViroPharma), R1626 (Roche), R7128 (Roche/Pharmasset), GS-9190 (Gilead), MK-0608 (Merck), PSI-6130 (Pharmasset), and PFE-868,554 (PFE).

A number of toll-like receptor (TLR) agonists are in development for the treatment of HCV infection, and in accordance with the methods of the present disclosure, co-administration of an NS4B antagonist that prevents the binding of NS4B to the 3'-UTR of HCV RNA and a TLR agonist can be efficacious in the treatment of HCV. In one embodiment, an interferon alpha and/or a nucleoside analog such as ribavirin and/ or an HCV protease inhibitor and/or an HCV RNA polymerase inhibitor is/are also employed in this combination therapy. Suitable TLR agonists include, but are not limited to, TLR7 agonists (i.e., ANA245 and ANA975 (Anadys/ Novartis)) and TLR9 agonists (i.e., Actilon (Coley) and IMO-2125 (Idera)).

A number of thiazolide derivatives are in development for the treatment of HCV infection, and in accordance with the methods of the present disclosure, co-administration of an NS4B antagonist that prevents the binding of NS4B to the 3'-UTR of HCV RNA and a thiazolide, including, but not limited to, Nitazoxanide (Alinia, or other sustained release formulations of nitazoxanide or other thiazolides, Romark Laboratories) can be efficacious in the treatment of HCV. In an embodiment, an interferon alpha and/or a nucleoside analog such as ribavirin and/or an HCV protease inhibitor and/or an HCV RNA polymerase inhibitor and/or a TLR agonist is/are also employed in this combination therapy.

In another embodiment of the methods of the present disclosure, co-administration of an inhibiting agent that prevents the binding of NS4B to the 3'-UTR of HCV RNA and a cyclophilin inhibitor (i.e., NIM-811 (Novartis) and DEBIO-025 (Debiopharm)) and/or an alpha-glucosidase inhibitor (i.e., Celgosivir (Migenix)) and/or one or more agents from one or more of the other classes of HCV therapeutic agents discussed herein is used to treat HCV infection. Moreover, there are several targets within NS4B, and compounds that interact with these other targets can, in accordance with the methods of the present disclosure, be used in combination with an NS4B antagonist that prevents the binding of NS4B to the 3'-UTR of HCV RNA and, optionally, one or more of the other classes of inhibiting agents mentioned herein, to treat HCV infection. Such additional NS4B targets include: the N-terminal amphipathic helix (see PCT publication WO 2002/089731, incorporated herein by reference), the NS4B GTPase (see PCT publication WO 2005/032329, incorporated herein by reference), the second amphipathic helix, the PIP2 binding activity of the first amphipathic helix in NS4B (see U.S. provisional patent application Ser. No. 60/057,188, incorporated herein by reference).

Other agents that can be used in combination with inhibiting agents of the present disclosure that prevent the binding of NS4B to the 3'-UTR of HCV RNA include (i) agents targeting NS5A, including, but not limited to, A-831 (Arrow Therapeutics), AZD2836 (Astra Zeneca), and agents in development by XTL/Presidio or BMS (see PCT publications WO 2006/133326 and WO 2008/021928, incorporated herein by reference); (ii) agents targeting TBC1D20 and/or NS5A's interaction with TBC1D20 (see PCT publication WO 2007/018692 and U.S. patent application Ser. No. 11/844,993, incorporated herein by reference), (iii) agents targeting NS4B's GTPase activity (see PCT publication WO 2005/032329 and US patent application publication 2006/0199174, incorporated herein by reference); (iv) agents inhibiting membrane association mediated by the HCV amphipathic helices, such as those found in NS5A, NS4B, and NS5B (see PCT publication WO 2002/089731, supra), (v) agents targeting PIP2 or BAAPP domains in HCV proteins, such as those found in NS4B and NS5A (see U.S. provisional patent application 60/057,188, supra); (vi) agents targeting HCV entry, assembly, or release, including antibodies to co-receptors; (vii) agents targeting HCV NS3 helicase; (viii) siRNAs, shRNAs, antisense RNAs, or other RNA-based molecules targeting sequences in HCV; (ix) agents targeting microRNA122 or other microRNAs modulating HCV replication; (x) agents targeting PD-1, PD-L1, or PD-L2 interactions or pathway (see U.S. patent application publications 20080118511, 20070065427, 20070122378, incorporated herein by reference); and (xi) agents targeting HCV amphipathic helix function, such as AH2 inhibitors.

In another embodiment of the present disclosure, an inhibiting agent that prevents the binding of NS4B to the 3'-UTR of HCV RNA is used in combination with one or more drugs capable of treating an HIV infection to treat a patient that is co-infected with HIV and HCV. In another embodiment of the present disclosure, an inhibiting agent that prevents the binding of NS4B to the 3'-UTR of HCV RNA is used in combination with one or more drugs capable of treating an HBV infection to treat a patient that is co-infected with HBV and HCV. In an embodiment, an inhibiting agent that prevents the binding of NS4B to the 3'-UTR of HCV RNA is used in combination with a PD-L1 inhibitor to treat a viral infection.

As mentioned above, embodiments of the present include the administration of an inhibiting agent identified herein (or by using an embodiment of the screen of the invention) in conjunction with at least one additional therapeutic agent to treat a viral infection. Suitable additional therapeutic agents include, but are not limited to, ribavirin; a nucleoside analog (e.g., levovirin, viramidine, and the like.); an NS3 inhibitor; an NS5 inhibitor; an interferon; and a side effect management agent.

In an embodiment, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The disclosure also contemplates use of derivatives of ribavirin (see, e.g., U.S. Pat. No. 6,277,830).

In an embodiment, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

In an embodiment, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Nucleoside analogs that are suitable for use in a combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2':4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, $O^2,O^2$-anhydro-β-L-arabinofuranosyluracil, 2'-deoxy-β-L-uridine, 3'5'-Di-O-benzoyl-2'deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90112 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

In an embodiment, the at least one additional suitable therapeutic agent can include HCV NS3 inhibitors. Suitable HCV non-structural protein-3 (NS3) inhibitors include, but are not limited to, a tri-peptide as disclosed in U.S. Pat. Nos. 6,642,204, 6,534,523, 6,420,380, 6,410,531, 6,329,417, 6,329,379, and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309, 6,608,067, and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003) *J. Biol. Chem.* 278:20374-20380; NS3 inhibitor BILN 2061 (Boehringer-Ingelheim; Lamarre et al. (2002) *Hepatology* 36:301A; and Lamarre et al. (Oct. 26, 2003) *Nature doi:* 10.1038/nature02099); NS3 inhibitor VX-950 (Vertex Pharmaceuticals; Kwong et al. (Oct. 24-28, 2003) 54th Ann. Meeting AASLD); NS3 inhibitor SCH6 (Abib et al. (Oct. 24-28, 2003) Abstract 137. Program and Abstracts of the 54th Annual Meeting of the American Association for the Study of Liver Diseases (AASLD). Oct. 24-28, 2003. Boston, Mass.); any of the NS3 protease inhibitors disclosed in WO 99/07733, WO 99/07734, WO 00/09558, WO 00/09543, WO 00/59929 or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926); an NS3 protease inhibitor as disclosed in any one of U.S. Patent Publication Nos. 2003019067, 20030187018, and 20030186895; and the like.

In an embodiment, the NS3 inhibitor used in a combination therapy of the invention is a member of the class of specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B.

In an embodiment, the at least one additional suitable therapeutic agent includes NS5B inhibitors. Suitable HCV non-structural protein-5 (NS5; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) *Antimicrob. Agents Chemother.* 47:2674-2681; a benzothiadiazine compound as disclosed in Dhanak et al. (2002) *J. Biol Chem.* 277(41): 38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

In an embodiment, the NS5 inhibitor used in the combination therapies of the invention is a member of the class of specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

In an embodiment, the at least one additional therapeutic agent is an interferon, e.g., interferon-alpha (IFN-α). Any known IFN-α can be used in the treatment methods of the invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-αc2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon tradename.

The term "IFN-α" also encompasses consensus IFN-α. Consensus IFN-α (also referred to as "CIFN" and "IFN-con" and "consensus interferon") encompasses, but is not limited to, the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, the at least one additional therapeutic agent is CIFN.

In an embodiment, fusion polypeptides comprising an IFN-α and a heterologous polypeptide can also be used in the combination therapies of the invention. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303:540-548). Also suitable for use in the present disclosure are gene-shuffled forms of IFN-α. See, e.g., Masci et al. (2003) *Curr. Oncol. Rep.* 5:108-113. Other suitable interferons include, Multiferon (Viragen), Medusa Interferon (Flamel Technology), Locteron (Octopus), and Omega Interferon (Intarcia/Boehringer Ingelheim).

The term "IFN-α" also encompasses derivatives of IFN-α that are derivatized (e.g., are chemically modified relative to the naturally occurring peptide) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

In an embodiment, the IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In an embodiment, the PEGylated IFN-α contains a PEG moiety on only one amino acid. In another embodiment, the PEGylated IFN-α contains a PEG moiety on two or more amino acids, e.g., the IFN-α contains a PEG moiety attached to two, three, four, five, six, seven, eight, nine, or ten different amino acid residues. IFN-α may be coupled directly to PEG (i.e., without a linking group) through an amino group, a sulfhydryl group, a hydroxyl group, or a carboxyl group.

To determine the optimum combination of an inhibiting agent, such as indazole, with other anti-HCV agents, HCV replication assays and/or animal studies can be performed in the presence of various combinations of the various anti-HCV agents. Increased inhibition of replication in the presence of an additional agent (above that observed with monotherapy) is evidence for the potential benefit of the combination therapy.

In an embodiment, side effect management agents can be used in the treatment methods of the invention, and these include agents that are effective in pain management; agents that ameliorate gastrointestinal discomfort; analgesics, anti-inflammatories, antipsychotics, antineurotics, anxiolytics, and hematopoietic agents. In addition, embodiments of the invention contemplate the use of any compound for palliative care of patients suffering from pain or any other side effect in the course of treatment with a subject therapy. Exemplary palliative agents include acetaminophen, ibuprofen, other NSAIDs, H2 blockers, and antacids.

The inhibiting agents and pharmaceutical compositions provided herein can be used to treat a variety of patients or hosts infected with a virus of the Flavivirus family. The subject treatment methods may particularly benefit "treatment failure patients". Such patients include but are not limited to those who have failed to respond to previous therapy for HCV (referred to as "non-responders") or who initially responded to previous therapy, but in whom the therapeutic response was not maintained (referred to as "relapsers"). The previous therapy generally can include treatment with any anti-viral agent other than an inhibiting agent of the present disclosure.

Other patients that may benefit from the subject treatments are individuals who have been clinically diagnosed as infected with HCV. Such individuals include naïve individuals (e.g., individuals not previously treated for HCV). Individuals who are infected with HCV can be identified by detecting HCV RNA in their blood, and/or having an anti-HCV antibody in their serum.

In some embodiments, hosts suitable for treatments of the present invention have an HCV titer of at least about $10^5$, at least about $5\times10^5$, or at least about $10^6$, genome copies of HCV per milliliter of serum. The patient may be infected with any HCV genotype (genotype 1, including 1a and 1b, 2, 3, 4, 6, and the like and subtypes (e.g., 2a, 2b, 3a, and the like.)), particularly a difficult to treat genotype such as HCV genotype 1 and particular HCV subtypes and quasispecies.

Also suitable for treatment are HCV-positive hosts (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment, or who have a contraindication to therapy with a known anti-viral agent.

In an embodiment, HCV-positive hosts with stage 3 or 4 liver fibrosis according to the METAVIR scoring system are suitable for treatment with the methods of the present disclosure. In another embodiment, hosts suitable for treatment with embodiments of the present disclosure are patients with decompensated cirrhosis with clinical manifestations, including patients with far-advanced liver cirrhosis, including those awaiting liver transplantation. In still another embodiment, hosts suitable for treatment with embodiments of the present disclosure include patients with milder degrees of fibrosis including those with early fibrosis (stages 1 and 2 in the METAVIR, Ludwig, and Scheuer scoring systems; or stages 1, 2, or 3 in the Ishak scoring system).

In an embodiment of the present disclosure, to help optimally select patients most likely to benefit from therapy, as well as to monitor efficacy of therapy—especially in the face of potential drug resistant mutant viruses—the use of appropriate diagnostic tests provided by the present invention can be of great benefit. For example, assessing the sensitivity of the specific virus found in a given patient to the contemplated therapy can help identify the best match between candidate patient and the corresponding appropriate therapy. In the case of isosteres of a benzimidazole core structure identified herein, this can be done by isolating the NS4B sequence from a given patient's HCV isolate and determining the efficacy of the drug's inhibition of RNA binding by the patient's NS4B isoform. This is especially important, because there currently is no efficient way of studying the drug sensitivity of a given patient's virus, because patient-derived inoculums cannot be readily cultured. The value of using such diagnostic assays to guide therapy has been extensively validated in HIV.

Combination therapy with an isostere of a benzimidazole core structure in accordance with embodiments of the present invention includes, for example and without limitation, (1) treatment with indazole plus nitazoxanide, (2) treatment with indazole followed by nitazoxanide, (3) treatment with indazole plus nitazoxanide and a NS3 protease inhibitor, (4) treatment with indazole plus nitazoxanide plus a NS3 protease inhibitor plus a NS5B polymerase inhibitor, (5) treatment with indazole plus a NS3 protease inhibitor plus a NS5B polymerase inhibitor, (6) treatment with indazole plus nitazoxanide plus a NS3 protease inhibitor plus a NS4B second amphipathic helix inhibitor, (7) treatment with indazole plus nitazoxanide plus a NS4B second amphipathic helix inhibitor, (8) treatment with indazole plus a NS3 protease inhibitor plus a NS4B second amphipathic helix inhibitor, (9) treatment with indazole plus ribavirin, (10) treatment with indazole followed by nitazoxanide plus ribavirin; (11) indazole plus clemizole hydrochloride; and (12) any other combinations of one or more agents listed above (1)-(11). In some embodiments, the one or more additional therapeutic agents are administered prior to, concurrent with, or subsequent to the treatment with indazole, indazole analogs or isosterers of the present invention.

Nitazoxanide administration in accordance with the combination therapies of the invention can be, for illustration and without limitation, 500 mg po BID. Other doses, other thiazolides, or other formulations of nitazoxanide or another thiazolide, such as sustained release formulations, can also be used in the combination therapies of the invention.

The inhibiting agents and pharmaceutical compositions thereof can be administered to a subject using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

Embodiments of the inhibiting agent can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The inhibiting agent can also be delivered to the subject by enteral administration. Enteral routes of administration include, but are not limited to, oral and rectal (e.g., using a suppository) delivery.

Methods of administration of the inhibiting agent through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more. In some embodiments, indazole is administered by oral, intravenous, transdermal, sublingual, intramuscular, or rectal route.

In a separate but related embodiment, the present invention further provides an in vitro cell-free method of identifying agents (inhibiting agents) that modulate RNA binding to an RNA-binding protein. A test agent that inhibits binding of NS4B polypeptide to the 3'UTR of HCV negative strand RNA can be further tested for its ability to inhibit HCV replication in a cell-based assay. For example, a test agent of interest can be contacted with a mammalian cell that harbors all or part of an HCV genome; and the effect of the test agent on HCV replication is determined. Suitable cells include mammalian liver cells that are permissive for HCV replication, e.g., an immortalized human hepatocyte cell line that is permissive for HCV. For example, a suitable mammalian cell is Huh7 hepatocyte or a subclone of Huh7 hepatocyte, e.g., Huh-7.5. Suitable cell lines are described in, e.g., Blight et al. (2002) *J. Virol.* 76:13001; and Zhang et al. (2004) *J. Virol.* 78:1448. In an embodiment, the HCV genome in the cell comprises a reporter, e.g., a nucleotide sequence encoding luciferase, a fluorescent protein, or other protein that provides a detectable signal; and determining the effect, if any, of the test agent on HCV replication is achieved by detection of a signal from the reporter.

In an embodiment, the test agents are organic moieties. In this embodiment, as is generally described in WO 94/24314, which is incorporated herein by reference, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepines, beta-lactams, tetracyclines, cephalosporins, and carbohydrates), steroids (including estrogens, androgens, cortisone, ecodysone, and the like), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present methods.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g., amounts, temperature, and the like.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

The 9.6-kb positive single-stranded RNA HCV genome encodes a 3,000-amino-acid polyprotein which is proteolytically processed into structural proteins, which are components of the mature virus, and nonstructural proteins (NS), which are involved in replicating the viral genome. Like other positive strand RNA viruses, HCV appears to replicate in association with intracellular membrane structures. In the case of HCV, the structures are termed the membranous web and are believed to be induced by the NS4B protein. NS4B is also used to assemble the other viral NS proteins within the apparent sites of RNA replication.

NS4B and HCV RNA have been shown to colocalize to the membranous web suggesting that NS4B is in intimate contact with viral RNA in the context of authentic viral RNA replication. The hepatitis A and polio picornaviruses have proteins termed 2C which are used for replication, bind RNA, and have an N-terminal amphipathic helix and a nucleotide binding motif. NS4B contains the same structural features, and both of them are used for HCV replication. Like the majority of drug targets, NS4B is a membrane protein (SEQ ID NO: 2).

The use of the microfluidic platform for RNA binding was validated by studying two human proteins from the embryonic lethal abnormal visual system (ELAV) family, the RNA binding activity of which has been previously well-characterized. This methodology is then applied to screen a compound library for pharmacologic inhibitors of NS4B RNA binding and HCV replication. These pharmacologic inhibitors have great therapeutic potential for HCV treatment and prevention.

High-Throughput Screening for Inhibitory Compounds.

In accordance with the methods described in priority applications US/2008/076804 and US/2008/076806 (both of which are incorporated herein by reference), a compound library is screened to identify small molecules that can inhibit the RNA-NS4B interaction. Approximately 1000-5000 compounds from a small molecule library of indazole-based isosteres of clemizole are spotted on epoxy-coated slides as a microarray. The array is allowed to dry, and then aligned and bonded to a microfluidic device. The rest of the assay is performed by loading the device with NS4B-GFP and followed by a Cy5-labeled 3' terminus negative RNA probe. In the primary screen, the compounds are spotted at a concentration of ~1 mM. The entire library is screened in duplicate or triplicate.

The compounds identified in the primary screen can be subjected to a secondary screen. This can be done in a similar manner except that a smaller device is used, the spotted compound concentration is 10 fold lower than in the primary screen and 3-10 replicates are spotted for each compound.

Inhibitors of HCV RNA Replication.

The in vivo antiviral effect on HCV RNA replication of the inhibitory compounds identified in the above screen is measured. Following electroporation with a full-length HCV RNA genome harboring a Luciferase reporter gene, Huh7.5 cells are grown in the presence of increasing concentrations of these compounds. Luciferase assays are performed at about 48 hr to about 72 hr or 96 hr. In parallel, the viability of cells in the presence of the compounds is assessed by an Alamar Blue-based assay. An indazole based isostere of clemizole hydrochloride (1-p-Chlorobenzyl-2-(1-pyrrolidinyl)methylbenzimidazole hydrochloride), provided herein, may, like clemizole, significantly inhibit HCV replication. Similar results are expected to be obtained by real-time PCR assays performed in Huh7.5 cells infected with the infectious HCV clone (J6/JFH) and treated with one or more indazole compounds of the present invention.

Methods and Materials

Plasmids:

Standard recombinant DNA technology is used to construct and purify all plasmids. All regions that are amplified by PCR are analyzed by automated DNA sequencing. Plasmid DNAs are prepared from large-scale bacterial cultures and purified by a Maxiprep kit (Marligen Biosciences). Restriction enzymes are purchased from New England Biolabs.

The open reading frames (ORF) of HuR and HuD are obtained from the ORFeome library of cDNA clones (Open biosystems). These ORFs are inserted into the expression vector pcDNA-Dest 40 vector (Invitrogen) by the use of gateway technology (Invitrogen) allowing addition of a C-terminal V5-his tag.

The plasmid pcDNA-NS4B-GFP encoding NS4B of genotype 1a fused in frame with a C-terminal GFP has been previously described. The plasmid NS5A(AH)GFP is constructed as previously reported. Gus-his vector is obtained from Roche.

The plasmid pcDNA3.1-5' UTR pos which encodes the 5' UTR of the positive viral strand, is generated by amplification of the 5' UTR positive sequence from the Bart791 plasmid with primers containing EcoRV restriction sites, digestion with EcoRV and ligation into the corresponding site in pcDNA3.1 (Invitrogen). The plasmid pcDNA3.1-3' negative terminus which encodes the 3' terminal region of the negative RNA strand is generated the same way except that the EcoRV-flanked insert is ligated in an inverse orientation.

The plasmids pcDNA3.1-3' UTR pos and 5' negative terminus are similarly generated except that the inserted gene is flanked by HindIII and XhoI restriction sites.

The vector encoding the delta virus genomic RNA sequence is cloned by inserting NheI flanked HDV sequence into a pSPT19 vector (Roche Diagnostics) cut with XbaI.

The plasmid FL-J6/JFH-5'C19Rluc2AUbi that consists of the full-length HCV genome and expresses *Renilla* luciferase was a gift from Dr. Charles M. Rice.

In Vitro RNA Transcription and Fluorescent and Radioactive Labeling.

Plasmid DNA of the 5' and 3' terminal regions of the negative and positive viral strands are linearized with XbaI. The plasmid DNA of the delta genomic sequence is linearized with XbaI. Linearized plasmids are then treated with proteinase K, followed by phenol-chloroform extraction and precipitation with ethanol. The DNA is resuspended in RNase free water to a final concentration of 1 µg/µl. 4 µs of DNA are used as a template for transcription with the T7 MEGAscript (Ambion) according to the manufacturer's protocol. The template DNA is digested by the addition of 5 U of RQ1 DNase (Ambion) and a 15-min incubation at 37° C. The unincorporated ribonucleotides are removed by size exclusion with a Micro Bio-Spin P-30 column (Bio-Rad), and the transcribed RNA is extracted with phenol-chloroform, followed by precipitation in ethanol. The RNA pellet is washed with 70% ethanol and resuspended in $H_2O$. Determination of the RNA concentration is performed by measurement of the optical density at 260 nm. The integrity of the RNA and its concentration are confirmed by 1% agarose gel electrophoresis and ethidium bromide staining.

The RNA sequences are labeled with Cy5 by using Label IT kit (Mirus) according to the manufacturer protocol followed by purification on a microspin column (Mirus) and ethanol precipitation. The number of fluorescent labels per RNA molecule is determined by measuring the spectrophotometric absorbance of the nucleic-dye conjugate at 260 nm and the $\lambda_{MAX}$ for Cy5 (650 nm). This is proportional to the probe's length and is used to adjust binding experiments results.

Cy3-labeled RNA probes used to study RNA binding by HuR and HuD are purchased from IDT.

Radioactive labeling of RNA probes with 32P is done as previously described.

Device Design:

The microfluidic device used for screening anti-viral compounds is fabricated according to methods described in the priority patent application US/2008/076804 and US/2008/076806, both of which are incorporated herein by reference.

The performance of RNA binding assay with the fluidic device as well as imaging and data analyses are carried out in accordance with the methods disclosed in the above-referenced priority applications.

Screening of Inhibitory Compound Library.

The compounds of the library can be obtained from commercial sources, solubilized in Dimethyl sulfoxide (DMSO) and spotted onto epoxy coated glass substrates slide (CEL Associates) using an OmniGrid Micro (GeneMachines) microarrayer and a CMP3B pin (TeleChem International, Inc.) as a microarray. For the primary screen, compounds are spotted at a high concentration (~1 mM) in duplicates. The array is allowed to dry, and was then aligned and bonded to a microfluidic device. Two large devices (2400 unit cells per device) are used for the primary screen. The rest of the procedure is done similarly to the procedure described above (RNA binding assay). In brief, the device is subjected to surface patterning that results in a circular area coated with biotinylated anti-GFP antibodies within each unit cell. Next, NS4B-GFP expressed prepared "off chip" using coupled transcription/translation rabbit reticulocyte system (Promega) in the presence of microsomal membranes (Promega) is loaded into the chip and bound to the surface biotinylated anti-GFP antibodies. Cy5-labeled 3' neg terminus RNA probe is then loaded at a concentration of about 1-5 nM. Each unit cell is then isolated followed by an approximately 30 min incubation to allow binding of the protein to surface biotinylated anti-GFP antibodies, solvation of library compounds, and equilibration of proteins and target RNA. Next, MITOMI is performed trapping surface-bound complexes while expelling any solution phase molecules. After a brief wash to remove untrapped unbound material, the device is scanned and results analyzed. The ratio of bound RNA to expressed protein is calculated for each data point by measuring the median signal of Cy3 to median signal of bodipy. Results are normalized to signal measured in unit cells containing no inhibitory compound. Greater than 90% inhibition is defined as the cutoff for inhibition in the primary screen. Compounds which are above this cutoff and are subjected to a secondary screen. This secondary screen is performed similarly, except that two smaller devices (640 unit cells per each) are used, the spotted compound concentration is about 10 fold lower than in the primary screen, and 3-10 replicates are spotted for each compound. Inhibition greater than about 2.5 fold is considered significant.

Determination of IC50 for In Vitro RNA Binding.

For an accurate measurement of IC50s, serial dilutions of the inhibitory compound are loaded onto the microfluidic device by continuous flow while maintaining a steady concentration of the compound in the flow channel. This helps to avoid losses of the spotted compounds from incomplete solubilization and/or binding of the compound to PDMS. The experiment is performed essentially as described for the RNA binding assay for transmembrane proteins except that the expressed protein and the Cy5-labeled HCV RNA probes are incubated in the device in the presence of the inhibitory compounds or their absence. IC50s are measured as described in the Statistical Analysis section below.

Expression and Purification of Recombinant NS4B.

GST-NS4B and GST are expressed in *E. coli* BL21 and purified as described elsewhere. NS4B is fused in frame with an N-terminal 6his-MISTIC protein (membrane-integrating sequence for translation of 1M protein constructs). Overnight cultures of *E. coli* transformed with mistic-NS4B plasmid are diluted 1:100 in 400 ml of fresh medium and grown at about 37° C. to an OD of between about 0.5 to about 2. Isopropyl-β-D-thiogalactopyranoside (IPTG) (Invitrogen) is then added to a final concentration of between about 0.1 mM to about 5 mM. After about 1 to about 4 hours growth at 37° C., cells are pelleted and resuspended in about 30 ml lysis buffer (~50 mM NaCl, ~50 mM Tris HCL (pH7-8.5), ~100 mM Imidazole, ~10 mM Decylmaltoside, Complete EDTA free protease inhibitors (Roche Applied Science)). Cells are lysed by one cycle in a French Press at a pressure of about 10,000 psi for 0.5-5 minutes, followed by centrifugation at 5,000-15,000 g for 1-10 minutes at 0-10° C. The supernatant is loaded on nickel column (Amersham). Following washes, protein is eluted in a buffer containing 125-1000 mM Imidazole. Glycerol is added at a final concentration of 5-25% and samples are stored at about −20° C. Purification is monitored by SDS-PAGE. Total protein concentration is measured using the RC-DC assay (Bio-Rad). NS4B-mistic is identified by Western blot analyses using monoclonal antibodies against 6-his (Santa Cruz Biotechnology) and NS4B (Virostat). 6his-mistic is expressed and purified in a similar manner.

GST Pull Down Assay.

1 μg of purified GST-NS4B or GST is incubated for about an hour at 37° C. in about a 25-100 μl reaction mixture containing $^{32}$P-labeled in vitro transcribed HCV RNA (corresponding to the 3' terminus of the negative viral strand) and binding buffer (~10mM DTT, ~10 mM Na HEPES (pH 7-8), ~33 mM NaCl, ~0.1 mM EDTA, ~10 mM MgCl2). 10-100 μl of tRNA pre-coated glutathione-agarose beads (Sigma) are then added, followed by 0.5-3 hours or more incubation at between about room temperature and about 0° C. or about 4° C. to allow binding of GST to the beads. The beads are then washed one to about five times in binding buffer and bound RNA is measured by liquid scintillation counting of sample aliquots. Control incubations with an RNA probe prepared in the absence of T7 RNA polymerase are used for background subtraction.

RNA Filter Binding Assay.

Assays are performed essentially as described. Briefly, various concentrations of mistic-NS4B protein or mistic control are incubated for about 0.5 to about 3 hours at about 30° C. with ~3.3 nM $^{32}$P-labeled in vitro transcribed HCV RNA probe in binding buffer (~50 mM HEPES pH 7.0-8.0, ~50 mM NaCl, ~1 mM $MgCl_2$, ~10 ng/μl tRNA, and ~0.2 mM Decylmaltoside) in a final volume of about 20 μl to about 100 μl. Membranes are pre-soaked in the binding buffer and assembled in a dot blot apparatus (Schleicher & Schull) from top to bottom as follows: nitrocellulose (Biorad), Hybond N+ (Amersham Biosciences), Whatman 3 mm filter paper. The binding reactions are loaded onto the dot-plot apparatus and filtered through the membranes. After washing, the membranes are air-dried and visualized by Phospho-imaging. Results represent the percentage of bound RNA calculated by dividing the signal detected in the nitrocellulose membrane by the sum of the signals detected in the nitrocellulose and the Hybond membranes.

Cell Cultures and Electroporation.

Huh-7.5 cells are maintained in Dulbecco's modified minimal essential medium (Gibco) supplemented with 1% L-glutamine (Gibco), 1% penicillin, 1% streptomycin (Gibco), 1× nonessential amino acids (Gibco) and 10% fetal bovine serum (Omega Scientific). Cell lines are passaged twice weekly after treatment with 0.05% trypsin-0.02% EDTA and seeding at a dilution of 1:5. Subconfluent Huh-7.5 cells are trypsinized and collected by centrifugation at 700 g for 5 min. The cells are then washed three times in ice-cold RNase-free PBS (BioWhittaker) and resuspended at between about $0.5*10^7$ cells/ml and about $2.5*10^7$ cells/ml in PBS. Wild type or mutant FL-J6/JFH-5° C.19Rluc2AUbi RNA for electroporation is generated by in vitro transcription of XbaI-linearized DNA templates using the T7 MEGAscript kit (Ambion), followed by purification, essentially as described above (In vitro RNA transcription and fluorescent labeling). About 1-10 μg of RNA is mixed with 400 μl of washed Huh-7.5 cells in a 2 mm-gap cuvette (BTX) and immediately pulsed (0.82 kV, five 99 μs pulses) with a BTX-830 electroporator. After a 5-30 min recovery at about 25° C., pulsed cells are diluted into 2-25 ml of prewarmed growth medium. Cells from several electroporations are pooled to a common a stock and seeded in 6 well plates (about $5*10^5$ cells per well). After about 48 hours or 12-72 hr, medium is replaced and cells are grown in the presence of serial dilutions of the various inhibitory compounds (Sigma) identified in the screen. Untreated cells are used as a negative control for water soluble compounds. For compounds solubilized in DMSO, untreated cells are grown in the presence of corresponding concentrations of the solvent as a negative control. Medium is changed daily. After 72 hr of treatment, cells are subjected to an alamar blue based viability assay and luciferase assay.

Viability Assay.

Following about 48, about 72, or about 96 hrs of treatment, cells are incubated for 1-5 hrs at about 37° C. in the presence of 1-20% Alamar Blue reagent (TREK Diagnostic Systems). Plates are then scanned and fluorescence was detected by using FLEXstation II 384 (Molecular Devices, Inc.). Depending on the inhibitory compound's solvent, water (other compounds not in DMSO) or DMSO (D042, (allylnorapomorphine), R-108, Tropicamide, Thalidomide, Glyburide, LFM-A13), signal is normalized relatively to untreated samples or samples grown in the presence of DMSO, respectively.

Luciferase Assay.

Viral RNA replication is determined using *Renilla* luciferase assay (Promega). The same samples subjected to the viability assay described above are analyzed in this assay. According to the manufacturer's protocol, cells are washed with ice cold PBS and scraped off the plate into about 100 μl, 250 μl, or about 400 μl of ice-cold *Renilla* lysis buffer. About 10-20 or about 30 μl of the cell lysates are then loaded onto 96 well plates. About 50 μl, 100 μl, or about 200 μl of the *Renilla* luciferase assay buffer containing the assay substrate are injected and luciferase activity is measured using a Berthold LB 96 V luminometer. As above, signal is normalized relative to untreated samples or samples grown in the presence of the corresponding concentration of DMSO.

Luciferase activity detected in samples treated with 100 u/ml Interferon alpha B2 (PBL biomedical labs) is used as a positive control, demonstrating three log reduction at about 72 hr treatment. The experiment is repeated four times, each time with triplicates. IC50s are measured by fitting data to a three parameter logistic curve using the formula $Y=a+(b-a)/(1+10^{\wedge}(X-c))$ (BioDataFit, Chang Bioscience, Inc).

Real-Time PCR.

About $5\times10^4$ Huh7.5 ells are infected with cell culture-grown HCV titered at about $1.4\times10^4$ TCID50/ml, as described. About 2 hours after infection, cells are washed three times in culture medium. Cells are then treated daily with various concentrations of indazole compound. After about 72 hours, samples are subjected to the viability assay described above, following which TRIzol Reagent (Invitrogen) is added and total cell RNA is extracted in triplicates according to the manufacturer's instructions. Reverse transcription is then performed using random hexamers and Superscript II reverse transcriptase (Invitrogen, Carlsbad, Calif.). Real-time PCR is performed on the resulting cDNA to quantify the amounts of HCV and actin RNA (in separate reactions) in each sample. Standards are made using an in vitro-transcribed HCV RNA and human actin standard (Applied Biosystems, Foster City, Calif.). HCV is quantified using primers AGAGCCATAGTGGTCT (SEQ ID NO: 3) and CCAAATCTCCAGGCATTGAGC (SEQ ID NO: 4) and probe 6-carboxyfluorescein-CACCGGAATTGCCAGGAC-GACCGG-6 (SEQ ID NO: 5) carboxytetramethylrhodamine. Actin is quantified using beta-actin control reagents (Applied Biosystems) according to the manufacturer's instructions. HCV RNA level is adjusted to actin level and normalized relative to untreated samples.

Selection of Resistant Mutants.

Established HCV replicons-harboring cells and Huh7 cells electroporated de novo with a genotype 1b subgenomic HCV replicon (Bart 791) are passaged in the presence of neomycin and increasing concentrations of subject compounds (about 0.1 to about 160 μM or about 1-16 μM). Colonies that are able to grow in the presence of the compound are isolated and propagated for 5-10 passages and subjected to sequence analysis, as previously described.

Whole Cell RNA Electroporation.

Whole cell RNA is extracted from indazole-resistant replicon clones and from untreated replicon cells using TRIzol reagent (Invitrogen). Equal amounts of whole cell RNA (~50 μg) are electroporated into Huh7.5 cells as described above. Cells are grown under G418 selection in the presence or absence of subject compound for 3 weeks. The number of colonies is determined using Image J (NIH) following fixation and staining with Crystal violet.

Statistical Analysis.

Dissociation equilibrium constants ae determined by fitting data to the equation describing equilibrium binding; $Y=a*X/(b+X)$ (a and b represent maximum binding and Kd, respectively) by nonlinear least squares regression fitting (BioDataFit, Chang Bioscience). IC50s are measured by fitting data to a three parameter logistic curve using the formula $Y=a+(b-a)/(1+10^{\wedge}(X-c))$ (a, b and c represent minimum binding, maximum binding and logEC50, respectively)(BioDataFit, Chang Bioscience, Inc).

Specificity of hits identified in the small molecule screen: To determine the specificity of the hits identified in the small molecule screen, the HuR protein (one of the human RNA binding protein used to validate our RNA binding assay) is selected. Interestingly, other than binding to its target RNA sequence, 4A, this protein has been previously shown by others (*Virology* 274, 378-390 (2000), which is incorporated herein by reference) to bind the 3' terminus of the negative HCV strand. Binding of HuR to the consensus 4A RNA sequence is tested in the presence of the inhibitory molecules shown to inhibit RNA binding by NS4B.

Example 2

To demonstrate the in vivo efficacy of indazole-based isosteres of clemizole core in treating patients infected with HCV, patients chronically-infected with HCV are treated with one or more compounds of the present invention at a dose of about 100 milligrams, p.o. QD, BID, or QID for about 8 weeks. After the first three to four weeks of monotherapy, pegylated interferon (about 180 micrograms Pegasus (Roche) s.q. per week) is added. Thereafter the patients are continued on the pegylated interferon and nitazoxanide (about 500 mg. (Romark) p.o. BID. It is expected that HCV viral loads will decrease upon treatment with one or more compounds of the present invention.

Example 3

Chemical Synthesis Synthetic Method 1

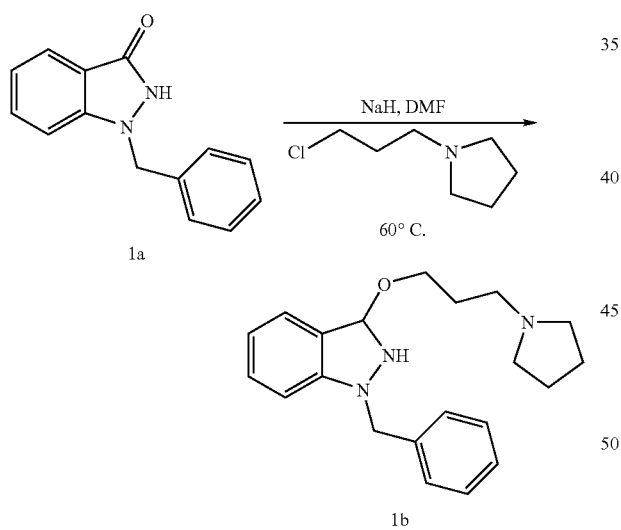

1-Benzyl-1H-indazol-3(2H)-one 1a (44 mg; 0.2 mmol) was dissolved in DMF (1 mL). NaH (12 mg, 0.3 mmol, 60% in mineral oil) was added, the resulting mixture was stirred at room temperature for 10 min. Followed by the addition of 1-(3-chloropropyl)pyrrolidine, the reaction mixture was heated at 60° C. for 2 h and monitored by LC-MS. The crude reaction mixture was purified by prep-HPLC to afford the desired product 1b (48.1 mg, 0.143 mmol, 72%). 1b was converted to the hydrochloride salt by treatment with HCl-ether-methanol.

The compounds is listed below can be prepared following Synthetic Method 1.

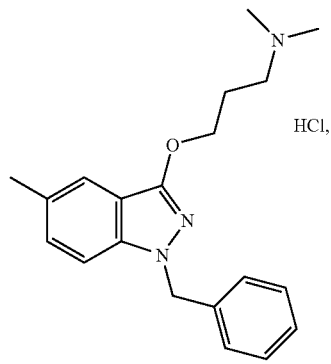

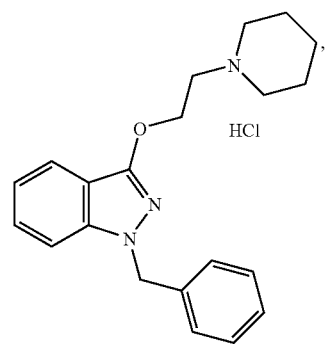

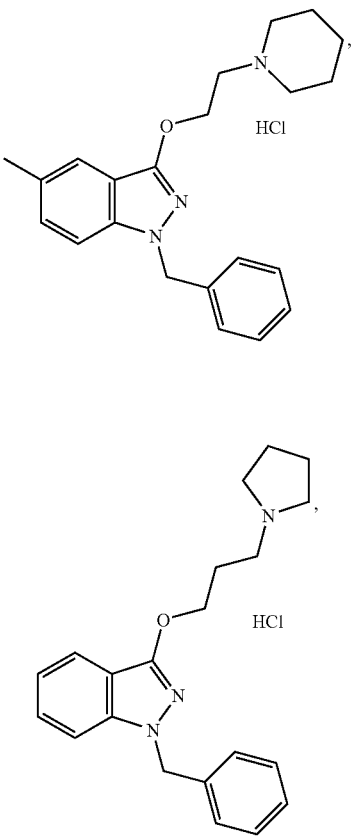

-continued
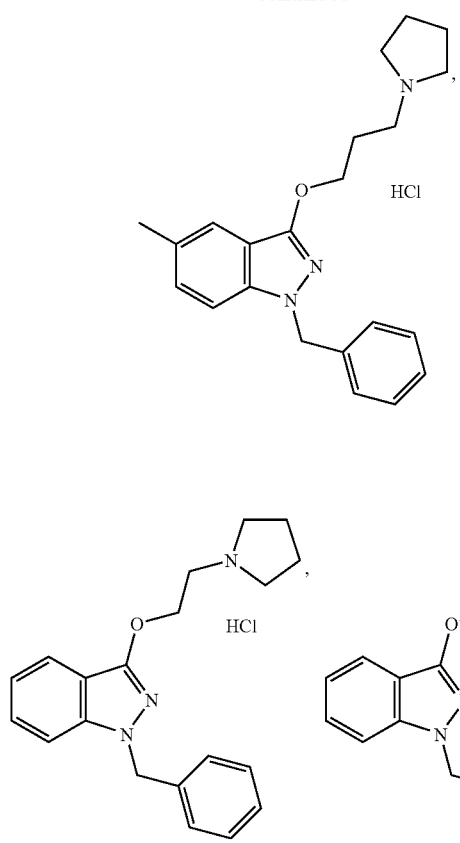
-continued
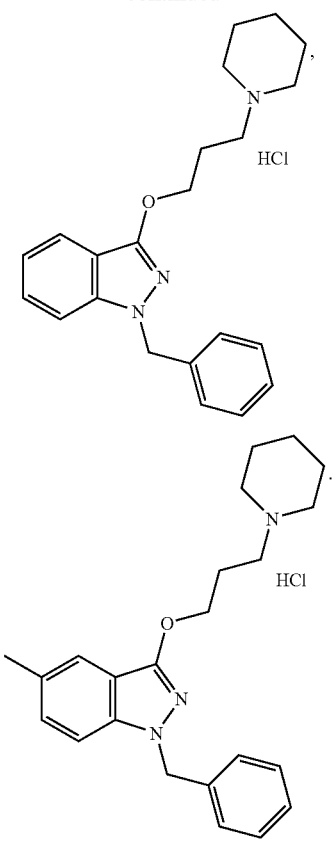
Synthetic Method 2
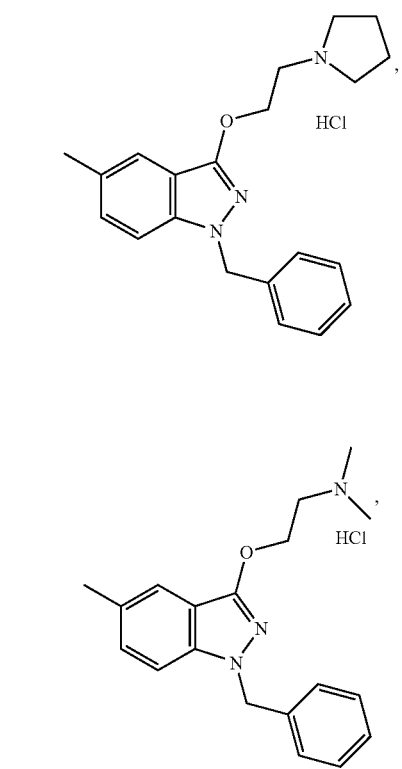
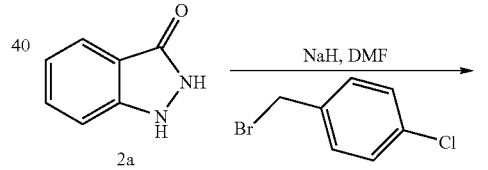
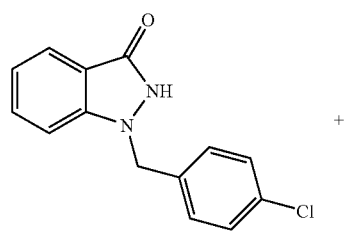
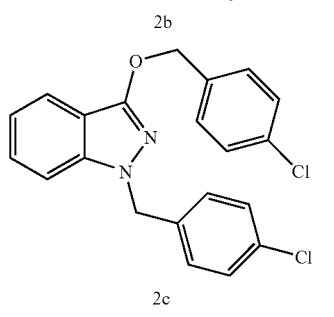

-continued

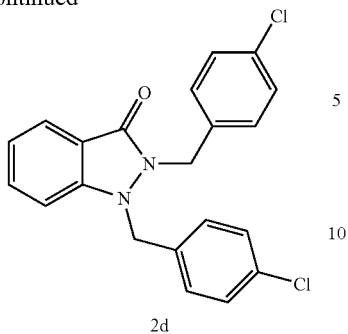
2d 1H-indazol-3(2H)-one 2a (268.3 mg; 2.0 mmol) was dissolved in DMF (5 mL). NaH (120 mg, 3.0 mmol, 60% in mineral oil) was added and the resulting mixture was stirred at room temperature for 10 min. This was followed by the addition of 1-(bromomethyl)-4-chlorobenzene and the reaction mixture was stirred at room temperature for additional 2 h. The reaction was monitored by LC-MS. The crude reaction mixture was purified by prep-HPLC to afford the desired product 2b (290.1 mg, 1.12 mmol, 56%) as major product along with side products 2c and 2d.

The compounds is listed below can be prepared following Synthetic Method 2.

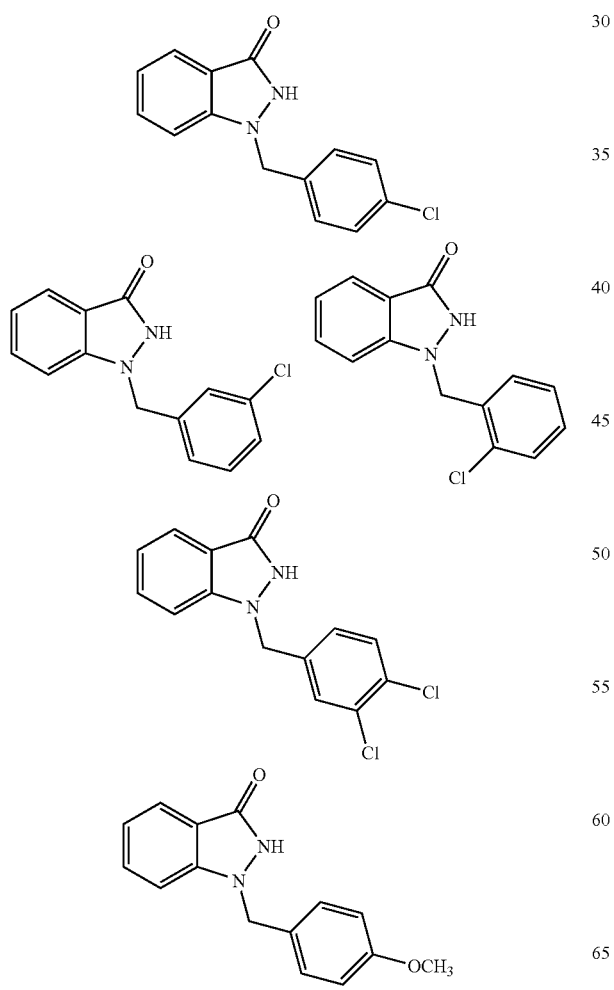

-continued

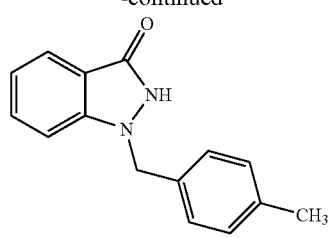

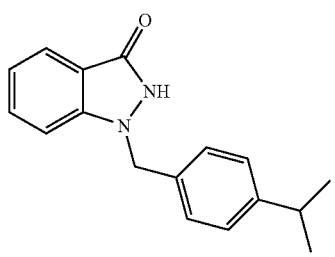

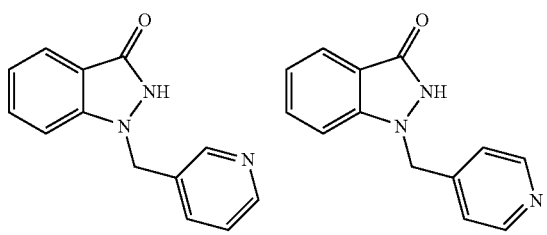

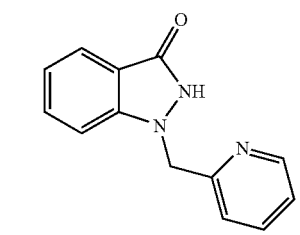

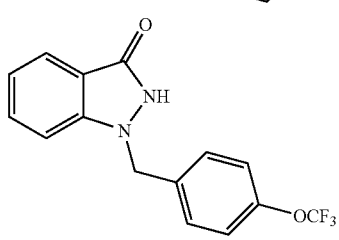

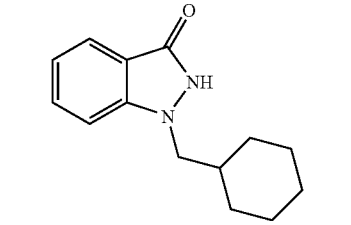

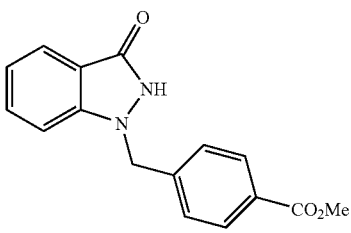

-continued

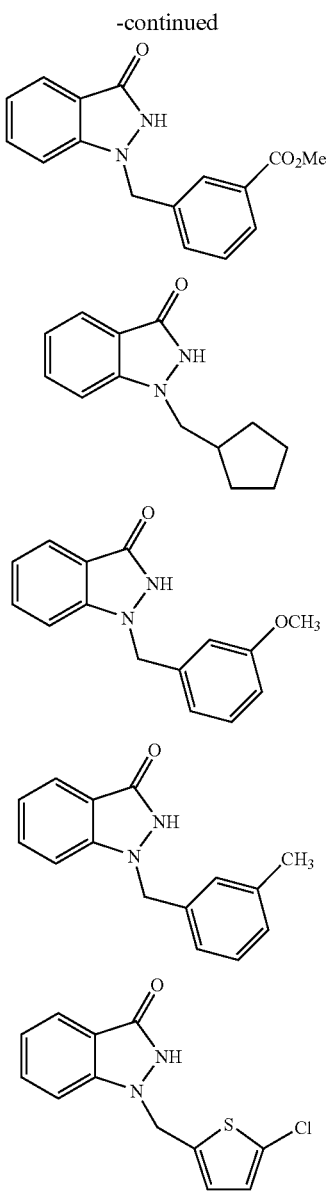

Synthetic Method 3

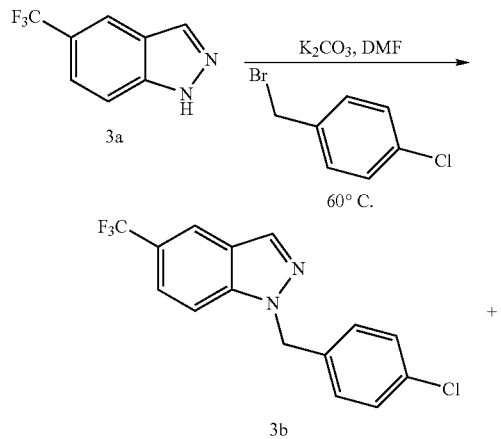

-continued

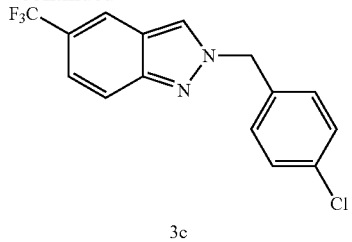

3c

Indazole compounds can be synthesized according to methods disclosed in the literature, e.g. Lukin et al. *J. Org. Chem.* 2006, 71, 8166-8172 and Souers et al. *J. Med. Chem.* 2005, 48, 1318-1321. A mixture of 5-(trifluoromethyl)-1H-indazole 3a (0.46 g, 2.5 mmol), $K_2CO_3$ (1.04 g, 7.5 mmol) in DMF (8 mL) was stirred at room temperature for 30 min. To the mixture was added p-chlorobenzyl bromide (0.77 g, 3.75 mmol). The resulting mixture was heated at 60° C. for 6 h. After cooling, the mixture was poured into water (30 mL). The precipitate was filtered and washed with water and dried. The crude product was purified by chromatography (hexane/dichloromethane, 1:1 to 1:3) to give 1-(4-chlorobenzyl)-5-(trifluoromethyl)-1H-indazole 3b (120 mg, 15%) and 2-(4-chlorobenzyl)-5-(trifluoromethyl)-2H-indazole 3c (60 mg, 7.7%).

1-(4-Chlorobenzyl)-5-(trifluoromethyl)-1H-indazole: $^1$H NMR (300 MHz, $CDCl_3$) δ 8.15 (s, 1H), 8.08 (d, 1H), 7.56 (dd, 1H), 7.41 (d, 1H), 7.28 (d, 2H), 7.12 (d, 2H), 5.60 (s, 2H).

MS calcd for $(C_{15}H_{10}ClF_3N_2+H)^+$: 310.9. MS found: $(M+H)^+=310.7$ 2-(4-Chlorobenzyl)-5-(trifluoromethyl)-2H-indazole: $^1$H NMR (300 MHz, $CDCl_3$) δ 8.04 (s 1H), 7.99 (s, 1H), 7.45 (dd, 1H), 7.35 (d, 2H), 7.22 (d, 2H), 5.60 (s, 2H).

MS calcd for $(C_{15}H_{10}ClF_3N_2+H)^+$: 310.9. MS found: $(M+H)^+=310.7$

The compounds listed below can be prepared following Synthetic Method 3.

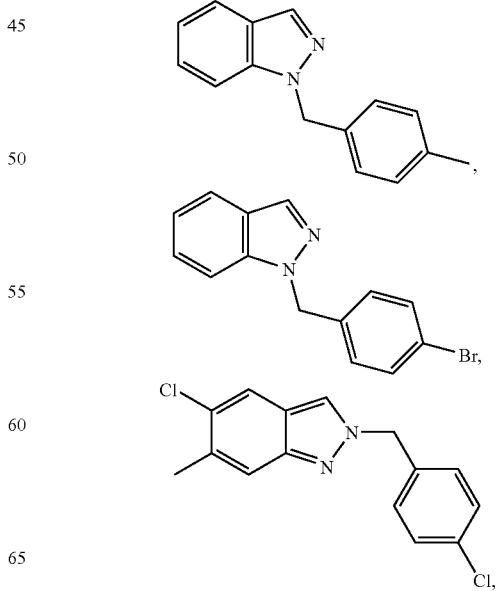

119
-continued

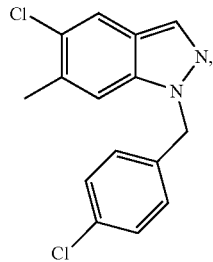

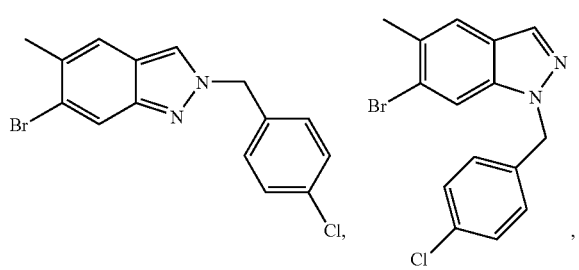

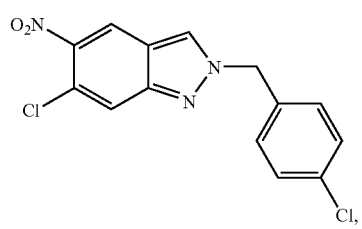

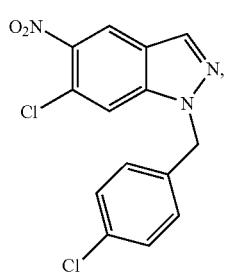

120
-continued

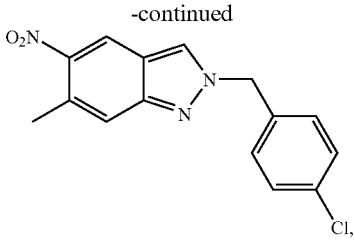

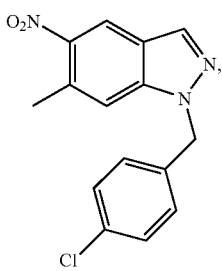

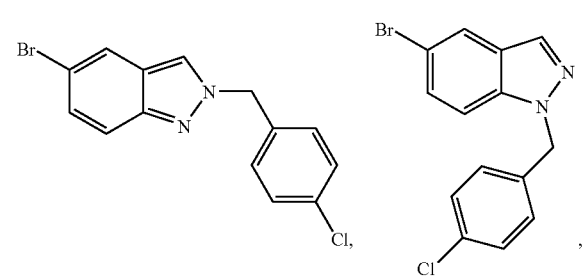

Example 4

Table 3 shown below illustrates the effects of indazole isosteres on HCV RNA replication (AV) and cell viability (Viab) using the Luciferase and Alamar Blue assays described herein. Compound activities were measured at two concentrations to determine whether the effects were dose-dependent. Numerical values represent the percent of normal activity (either viral replication or cell viability) remaining after compound treatment; these values have also been binned to provide a rough measure of relative activity.

The amount of residual luciferase activity (indicating HCV replication) in the treated cells relative to the no drug control for each compound was determined at two concentrations of compound, 5 micromolar and 10 micromolar, and recorded in the table. In addition, these percentages were converted to a scoring system as follows: "+">80% residual activity; "++"=55-80% residual activity; "+++"=20-54% residual activity; "++++"<20% residual activity. Thus a compound scored as +++ in the replication assay has greater antiviral activity (AV) than a compound scored as +.

TABLE 3

In-vitro activity of the compounds of the invention in the RNA replication inhibition assay described herein.

| Residual Luciferase activity[1] | <20% ++++ (Compound No.) | 20-54% +++ (Compound No.) | 55-80% ++ (Compound No.) | >80% + (Compound No.) |
|---|---|---|---|---|
| 5 micromolar | | 193, 198, 199, 210, | 187, 191, 192, 196, 208, 204, 212 | 184, 185, 186, 188, 189, 190, 194, 195, 197, 206, 200, 207, 201, 202, 209, 203, 211, 205 |
| 10 micromolar | 191, 193, 198, 199 | 184, 187, 188, 192, 196, 197, 208, 203, 210, 204, 212 | 190, 194, 206, 200, 207, 201, 211, 205, | 185, 186, 189, 195, 202, 209, |

[1]Luciferase reporter activity is stated as a percentage of the luciferase reporter activity in a treated cell population compared to the luciferase activity in an untreated control population of same cell type.

TABLE 4

In-vitro activity of the compounds of the invention in the cell viability assay described herein.

| Cell Viability[2] | 90% or greater (Compound No.) | 75% or greater (Compound No.) | 50% or greater (Compound No.) | <50% (Compound No.) |
|---|---|---|---|---|
| 5 micromolar | 184, 185, 186, 187, 188, 189, 190, 191, 192, 193, 194, 195, 196, 197, 199, 206, 200, 207, 201, 202, 209, 203, 210, 204, 211, 205, | 198, 208, 212 | | |
| 10 micromolar | 184, 185, 186, 189, 190, 191, 192, 194, 195, 196, 197, 200, 207, 201, 202, 209, 203, 211, | 187, 188, 193, 198, 199, 206, 208, 210, 204, 205, 212 | | |

[2]Cell viability is stated as a percentage of viable cells in a treated population of cells in comparison to an untreated population of same cell type.

TABLE 5

Structures of the compounds listed in Tables 3 and 4

Compound 184

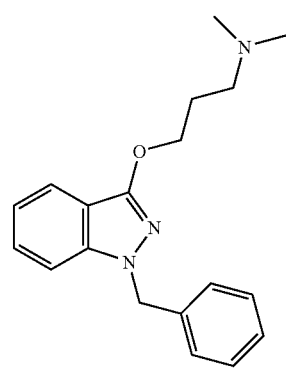 [SMILES: CN(C)CCCOc1nn(Cc2ccccc2)c2ccccc12]

Compound 185

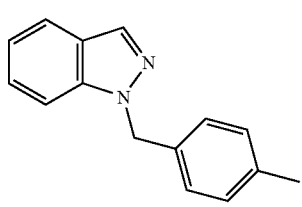 [SMILES: Cc1ccc(Cn2ncc3ccccc32)cc1]

TABLE 5-continued

Structures of the compounds listed in Tables 3 and 4

Compound 186

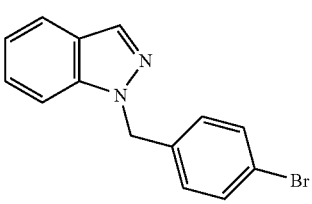 [SMILES: Brc1ccc(Cn2ncc3ccccc32)cc1]

Compound 187

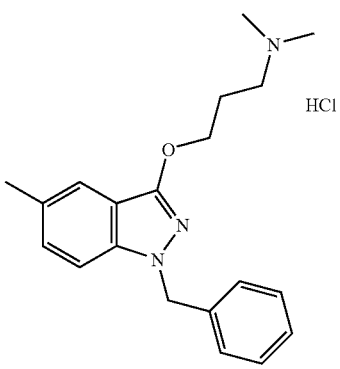

TABLE 5-continued
Structures of the compounds listed in Tables 3 and 4
Compound 188
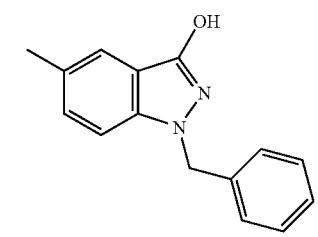 [SMILES: Cc1ccc2c(c1)c(O)nn2Cc1ccccc1]
Compound 189
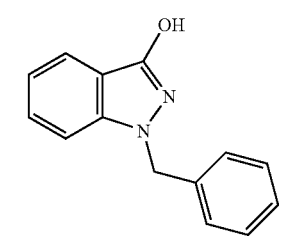 [SMILES: Oc1nn(Cc2ccccc2)c2ccccc12]
Compound 190
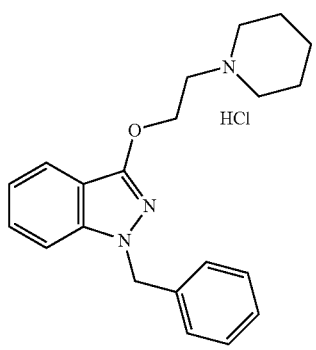 [SMILES: c1ccc(Cn2nc(OCCN3CCCCC3)c3ccccc32)cc1 ; Cl]
Compound 191
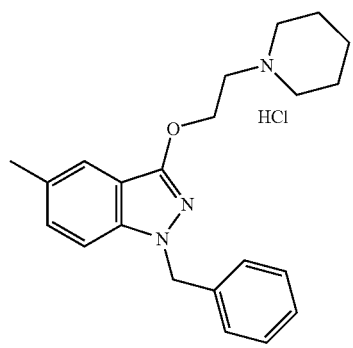 [SMILES: Cc1ccc2c(c1)c(OCCN1CCCCC1)nn2Cc1ccccc1 ; Cl]
TABLE 5-continued
Structures of the compounds listed in Tables 3 and 4
Compound 192
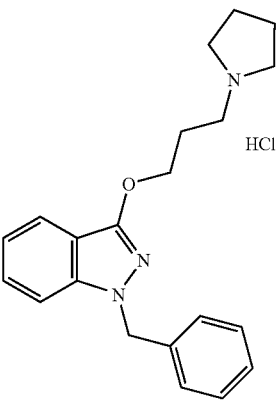 [SMILES: c1ccc(Cn2nc(OCCCN3CCCC3)c3ccccc32)cc1 ; Cl]
Compound 193
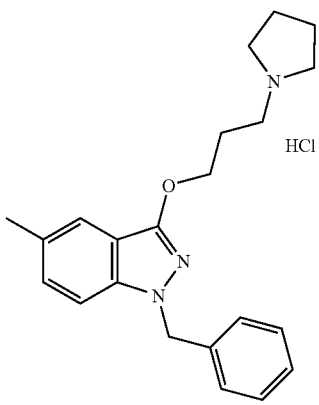 [SMILES: Cc1ccc2c(c1)c(OCCCN1CCCC1)nn2Cc1ccccc1 ; Cl]
Compound 194
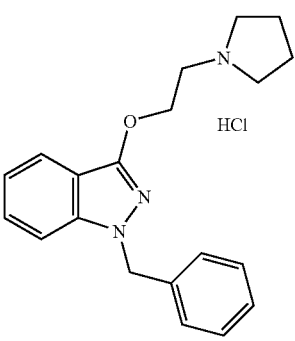 [SMILES: c1ccc(Cn2nc(OCCN3CCCC3)c3ccccc32)cc1 ; Cl]
Compound 195
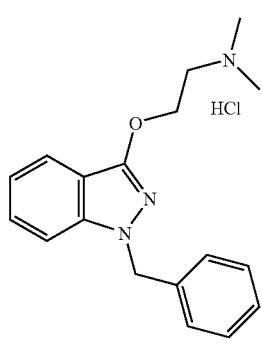 [SMILES: CN(C)CCOc1nn(Cc2ccccc2)c2ccccc12 ; Cl]

TABLE 5-continued
Structures of the compounds listed in Tables 3 and 4
Compound 196
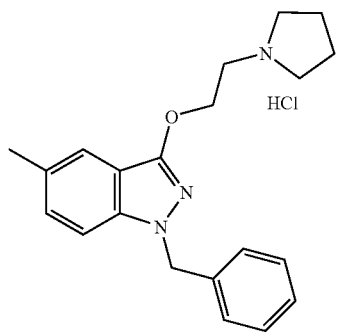 [SMILES: Cc1ccc2c(c1)c(OCCN1CCCC1)nn2Cc1ccccc1 ; Cl]
Compound 197
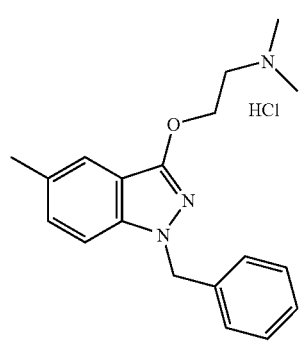
Compound 198
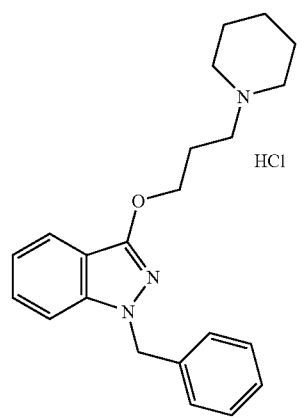 [SMILES: c1ccc(Cn2nc(OCCCN3CCCCC3)c3ccccc32)cc1 ; Cl]
Compound 199
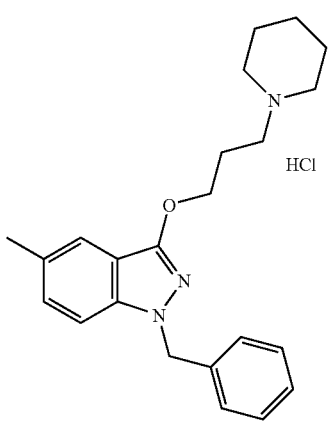 [SMILES: Cc1ccc2c(c1)c(OCCCN1CCCCC1)nn2Cc1ccccc1 ; Cl]
TABLE 5-continued
Structures of the compounds listed in Tables 3 and 4
Compound 200
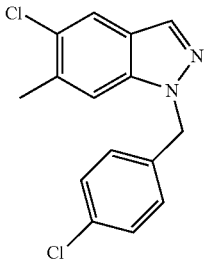 [SMILES: Cc1cc2c(cnn2Cc2ccc(Cl)cc2)cc1Cl]
Compound 201
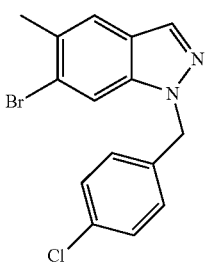 [SMILES: Cc1cc2cnn(Cc3ccc(Cl)cc3)c2cc1Br]
Compound 202
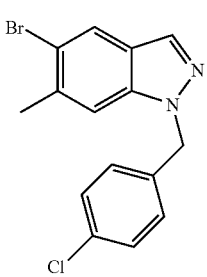
Compound 203
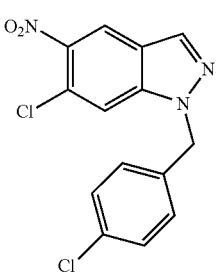 [SMILES: O=[N+]([O-])c1cc2cnn(Cc3ccc(Cl)cc3)c2cc1Cl]
Compound 204
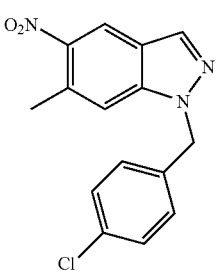 [SMILES: Cc1cc2c(cnn2Cc2ccc(Cl)cc2)cc1[N+](=O)[O-]]

TABLE 5-continued

Structures of the compounds listed in Tables 3 and 4

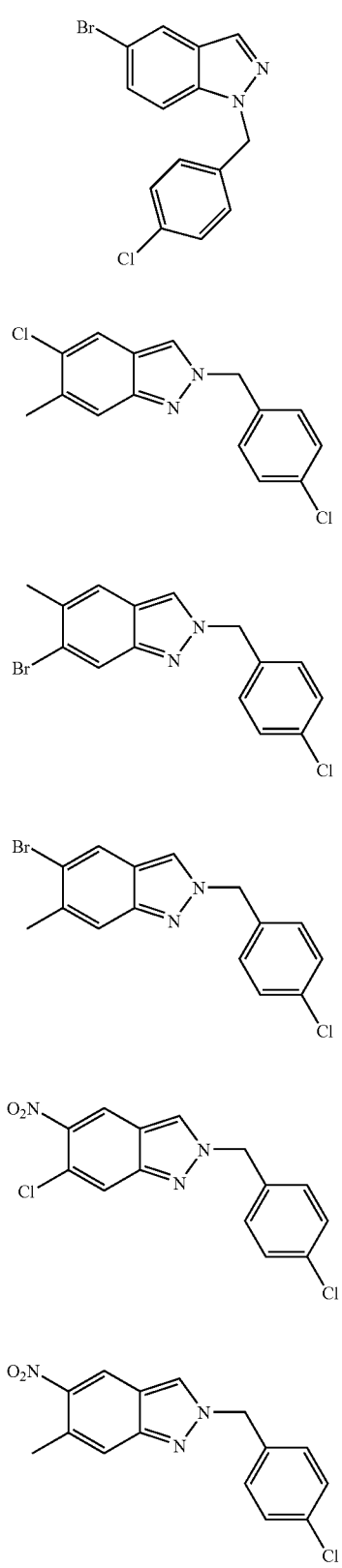

Compound 205

Compound 206

Compound 207

Compound 208

Compound 209

Compound 210

TABLE 5-continued

Structures of the compounds listed in Tables 3 and 4

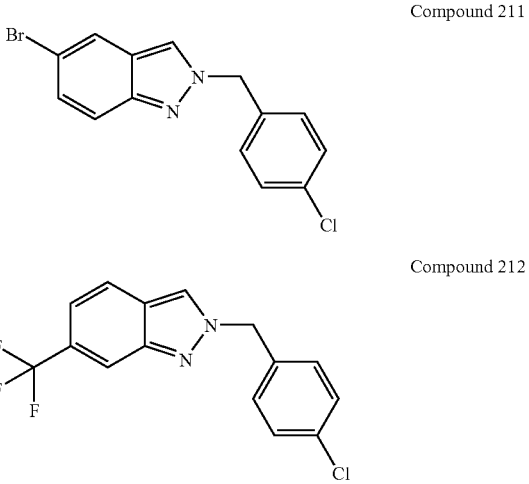

Compound 211

Compound 212

Example 5

Replication Assay Protocol

In an embodiment, the replication assay protocol can include the following stages. It should be noted that the following replication assay protocol is non-limiting, and presented as an illustrative embodiment of a replication assay protocol.

Stage 1: RNA Transcription

1) Linearize the FL-J6/JFH-5'C19Rluc2AUbi plasmid with XbaI at 37° C. for 2 hrs, and run on 1% agarose gel to check completeness of digestion.

2) Digest the 5' overhangs by treatment with mung bean nuclease at 30° C. for 30 min.

3) For linearization of the Bart79I-luc plasmid (similar to Bart79I plasmid as described in Elazar et al. J. Virol. 2003, 77(10):6055-61 except that the neomycinphospho-transferase gene has been replaced with the gene encoding firefly luciferase) use ScaI restriction endonuclease, then examine the linearized template DNA on a gel to confirm that cleavage is complete, follow this with proteinase k digestion.

4) Purify templates by digestion with proteinase K for 30 min, phenol-chloroform extraction, ethanol precipitation, and then resuspend at 1 µg/µl.

5) For the transcription reaction, use 1 µg of purified template by using the T7 Megascript kit for FL-J6/JFH-5'C19Rluc2AUbi (Ambion, Austin, Tex.) or the RiboMax™ kit for Bart79I-luc (Promega, Madison, Wis.). Incubate reactions at 37° C. for 4 h.

6) Add DNAse for 15 min.

7) Extract with an equal volume of phenol/chloroform and then with an equal volume of chloroform. Recover aqueous phase and transfer to new tube.

8) Precipitate the RNA by adding 1 volume of isopropanol and mixing well.

9) Chill the mixture for at least 15 min at −20° C. Centrifuge at 4° C. for 15 min at maximum speed to pellet the RNA.

10) Carefully remove the supernatant solution and resuspend the RNA in RNase/DNase-free Water at 1 µg/µl.

11) Run on a gel and check RNA concentration.

12) Make aliquots and store in −80° C.

Stage 2: Electroporating Huh7.5 Cells
1) Wash cells once with PBS, trypsinize.
2) Resuspend cells in a total volume of 5 ml per 10 cm plate of complete medium (pull all together) in 50 ml tubes.
3) Pellet cells at 1000×RPM for 5 min at 4° C. Aspirate sup and resuspend in 10 ml ice cold RNAse free filtered 1×PBS (BioWhitaker)—pipette up and down ~5 times gently to get rid of cell clumps.
4) Pellet cells again at 1000×RPM as before and again resuspend in 10 ml ice cold PBS (BioWhitaker).
5) Remove a 10 µl aliquot to determine cell concentration.
6) Pellet cells again and resuspend in a final concentration of $1.5 \times 10^7$ cells/ml in ice cold RNAse free-PBS.
Need: $6 \times 10^6$ cells in 0.4 ml per each electroporation (ep) and 5 µg of FL-J6/JFH-5'C19Rluc2AUbi RNA or Bart79I-luc RNA.
7) Place 5 µg RNA aliquot in an eppendorf tube (1 tube per ep).
8) Remove 0.4 ml of the cell suspension and add to the RNA. Mix twice by pipetting.
9) Immediately transfer 0.4 ml to a 2 mm gap ep cuvette.
10) Pulse the cells: 820v, 5 pulses, 99 µsec, 220 ms interval, unipolar.
11) Allow cells to rest for 15 min.
12) Transfer cells using the Pasteur pipette in the cuvette package to medium. Make a common stock from all tubes.
13) Plate 10,000 cells/well in 96 well plates.
14) Rotate plate a little for even cell plating.
15) Incubate for 24 hr before treatment.
Stage 3: Treating Plates
1) About 24 hr following electroporation prepare medium with the desired concentration of the drug.
2) Aspirate the medium and add 100 µl of fresh medium and drug. Leave untreated wells at the beginning and again at the end.
3) Repeat daily for 2 more days.
Stage 4: Harvesting (Day 5 from Electroporation)
1) Alamar Blue Assay—
a) Include medium for background subtraction (and also for seeing change in color easily).
b) Aspirate medium.
c) Make a stock of medium plus 10% Alamar blue. Total volume per well is 100 µl.
d) Incubate for 2-2.5 hrs at 37° C. (or until there is a color change).
e) Read plates at flex station.
2) *Renilla* Luciferase assay—
a) Aspirate medium with Alamar blue.
b) Wash with 1×PBS.
c) Aspirate completely (aspirate, then tilt and aspirate remainders of buffer again).
d) Make sure which lysis buffer is needed: firefly or *renilla*.
e) Add 30 µl of 1× lysis buffer (add 1 volume of 5× lysis buffer to 4 volumes of sterile water).
f) Shake the plate for 15 min.
g) Freeze at −80° C. At this point, one can stop or continue to the next phase.
Stage 5: Reading by Luminometer
a) Thaw the plate.
b) Leave plate on ice until ready to read.
c) Prepare substrate reagent you need; for the *renilla*: thaw *renilla* buffer, make 1 volume 100× *Renilla* luc substrate plus 100 vol luc assay buffer+2 ml for priming luminometer. (e.g., for 4 ml *Renilla* lucsubstrate, add 40 ul assay buffer). For the firefly; thaw 10 ml firefly buffer and add to the luciferase reagent.
d) Read plates using a standard luminometer according to the manufacturer's directions.

Example 6

HERG Channel Assay

Drugs belonging to different classes have been shown to be associated with QT prolongation and in some cases serious ventricular arrhythmias. The most common mechanism for these adverse events is the inhibition of one or more cardiac potassium channels, in particular hERG. This current is important for cardiac myocyte repolarization and is a common target for drugs that prolong the QT interval. Test articles in this study are therefore characterized to determine their ability to inhibit the hERG channel. Ion channel activity is measured using a stably transfected Chinese Hamster Ovary (CHO) cell line expressing the hERG mRNA. The pharmacology of this cloned channel expressed in the CHO cell line is very similar to that observed in native tissue.

Experimental Methods
Cells:
AVIVA's CHO cell line, which stably expresses hERG channels, is used for the study. Cells are cultured in DMEM/F12 containing 10% FBS, 1% penicillin/streptomycin and 500 µg/ml G418. Before testing, cells are harvested using Accumax (Innovative Cell Technologies).
Solutions:
For electrophysiological recordings, the following solutions are used:
External Solution: 2 mM CaCl2; 2 mM MgCl2; 4 mM KCl; 150 mM NaCl; 10 mM Glucose; 10 mM HEPES; 310-320 mOsm; pH 7.4 (adjusted with 1M NaOH.);
Internal Solution: 140 mM KCl; 10 mM MgCl2; 6 mM EGTA; 5 mM HEPESNa; mM ATP-Mg; 300-320 mOsm; pH 7.25 (adjusted with 1M KOH).
Electrophysiology:
Whole cell recordings are performed using PX 7000A (Axon Instruments) with VIVA's SealChip™ technology. Cells are voltage clamped at a holding potential of −80 mV. The hERG current is then activated by a depolarizing step to −50 mV for 300 ms. This first step at −50 mV is used as a baseline for measuring peak amplitude of the tail current. Next, a voltage step to +20 mV is applied for 5 seconds to activate the channels. Finally a step back to −50 mV for 5 seconds removed activation and the deactivating tail current is recorded.
Compound Handling and Dilutions:
All compounds are prepared from either 10 or 30 mM DMSO stock solutions. Solutions are mixed by sonication for 20 min, followed by vigorous vortexing. Prior to testing, compounds are diluted to test concentrations in glass vials using External Solution. Dilutions are prepared no longer than 20 min prior to use. Equal amounts of DMSO (0.1%) are present in all final dilutions.
Electrophysiology Procedures
After achieving whole cell configuration, cells are monitored for 90 seconds to assess stability and then washed with External Solution for 66 seconds. The voltage protocol described above is then applied to the cells every 12 seconds throughout the procedure. Only stable cells with recording parameters above threshold (see Quality Control section) are allowed to enter the drug addition procedure. External solution containing 0.1% DMSO (vehicle) is applied to the cells to establish a baseline. After allowing the current to stabilize for 3 to 5 min, test articles are applied. Test article solutions are added to cells in 4 separate additions. Cells are kept in test solution until effect of the test article reaches steady state, to a maximum of about 12 min. Next, about 1 μM cisapride (positive control) is added. Finally, washout with External Solution is performed until the recovery current reached a steady state.

Data Analysis

Data analysis is performed using DataXpress (Axon Instruments), Clampfit (Axon Instruments) and Origin (Originlab Corporation) software.

Quality Control

Data included in the report originates from experiments that satisfy all of the following criteria:

a) Recording Parameters: membrane resistance (Rm): >200 MΩ; access resistance (Ra): <15MΩ; tail current amplitude: >150 pA Following these procedures, several compounds provided by the present invention are found to lack substantial cross reactivity with hERG channel.

b) Pharmacological Parameters: 1 μM cisapride: >95% inhibition

| Compound | HERG IC$_{50}$ (μM) |
|---|---|
| 184 | 1.4 |

Experiment 7

HCV Treatment with Indazole in Combination HCV Protease Inhibitors

The synergistic antiviral activity of indazole analogues in combination with one or more protease inhibitors that inhibit HCV replication can be assayed as follows. Following electroporation with a full-length J6/JFH (genotype 2a) HCV RNA genome harboring a luciferase reporter gene, Huh7.5 cells are grown in the presence of various concentrations of the individual compounds and their combinations. Luciferase assays are performed in about 72 hours. In parallel, the viability of cells in the presence of the compounds is assessed by an Alamar Blue-based assay. Cells harboring the above HCV replicon with the luciferase reporter gene are treated with four different concentrations of protease inhibitor in the absence or presence of three different concentrations of indazole analogue.

To characterize the enhanced antiviral effect observed for the combination treatments, a sub-set of the generated combination data is analyzed using CalcuSyn™ (Biosoft, Inc., Cambridge, UK). As determined by this software, the data points analyzed are those where the drugs are mixed at a fixed molar ratio matching their equipotent concentrations. This molar ratio is maintained during serial dilutions, as previously described (Korba, 1996; Iyer et al., 2004).

The results are further analyzed using the MacSynergy mathematic model to better quantify the degree of the observed synergy. In this model, the effect of the combination is determined by subtracting the actual experimental values from theoretical additive values, calculated from the dose-response curves for single compound treatments based on Bliss Independence theory. When presented as a three-dimensional differential surface plot, synergy is demonstrated by peaks above a theoretical additive plane and antagonism as depressions below it. Only statistically significant effects based on the 95% confidence interval are considered at any given concentrations of the two compounds. As suggested by Prichard et al., data sets assessed at the 95% confidence level are interpreted as follows: volumes of synergy or antagonism at values of <25 μM$^2$ are considered insignificant, those at values of >25 but <50 μM$^2$ are considered minor but significant, those at values of >50 but <100 μM$^2$ are considered moderate and probably important in vivo, and those at values of >100 μM$^2$ are considered strong and likely to be important in vivo.

Experiment 8

Assaying for Genotypes Specific Effects of Combination Treatment

In order to determine whether or not any observed synergy of treatment with an indazole analogue of the present invention in combination with a protease inhibitor is genotype-specific, the experiments outlined above are repeated using genotype 1b luciferase reporter gene assays. Huh7.5 cells are electroporated with a subgenomic Bart 79I HCV RNA replicon harboring a luciferase reporter gene, and grown in the presence of increasing concentrations of the individual compounds or their combinations. As described above, luciferase assays and Alamar Blue-based viability assays are performed at about 72 hr.

Experiment 9

Focus Formation Assay of HCV Replication Inhibition

The effect of treatment with one or more compounds of the present invention alone or in combination with a protease inhibitor in inhibiting direct viral replication (versus activity of a luciferase gene) is determined by focus formation assays. Huh7.5 cells are infected in triplicates with cell culture-grown HCV titered at about 1.2×10$^4$ TCID50/ml, as described. About 2 hours after infection, cells are washed two to three or four times with culture medium. Cells are then treated daily with five different concentrations of subject compounds in the absence or presence of five different concentrations of protease inhibitor. After about 72 hours samples are subjected to an Alamar Blue-based viability assay, followed by fixation and immunofluorescence staining with anti-core antibody. Foci are counted under inverted microscope using the 20× magnification. It is expected that the average number of foci in untreated wells is higher than the wells with each drug alone in a dose dependent manner. This assay can be performed to show that when combined, the two drugs may result in substantially more potent antiviral effects than the single agent in all concentrations tested suggesting synergistic or additive effects, in the context of authentic viral infection.

Experiment 10

Assaying Combinations of Indazole Analogue with Either Interferon, a Nucleoside Analog or a Non-Nucleoside Analog Polymerase Inhibitors The antiviral activity of one or more compounds of the present invention is studied in combination with interferon using the 2a luciferase reporter gene assays, as described above. Escalating doses of one or more compounds of the present invention are added to a standard dose response study of interferon to generate a 4 by 4 matrix of concentrations. The calculated EC50 of interferon alone is compared with an EC50 of 1.8 units/ml previously determined by others in genotype 2a (Takanobu Kato, JCM, 2005). The synergy volume for the 95% CI synergy plot is calculated to assay for additive or synergistic effects. Similarly, 2 dimensional analysis using CalcuSyn™ is used to check for statistically significant deviation of the isobole from the line of additivity, as well as combination indices that indicate additive or synergistic effects.

The effect of combination treatment of indazole with HCV polymerase inhibitors is also assayed. Two polymerase inhibitors are chosen: NM283 (valopicitabine) a nucleoside analog, and HCV796, a non-nucleoside analogue, both shown to have an antiviral effect in HCV patients. As described above, a 4 by 6 matrix is generated by adding increasing doses of one or more compounds of the present invention to 5 different concentrations of each polymerase inhibitor. Luciferase reporter gene assays are performed as above and data analyzed using MacSynergy. The synergy volume for the 95% Cl synergy plot is calculated to assay for additive, antagonistic, or synergistic effects. Similarly, 2 dimensional analysis using CalcuSyn™ is used to check for statistically significant deviation of the isobole from the line of additivity, as well as combination indices that indicate additive, antagonistic, or synergistic effects.

Experiment 11

Assaying the Frequency of Phenotypic Resistance

One of the major goals in using combination antiviral drugs is to delay and/or decrease the emergence of viral resistance. The efficacy of treating cells infected with HCV with one or more compounds of the present invention in combination with a protease inhibitor to delay and/or decrease the emergence of viral resistance is tested as described herein. Huh7 cells electroporated de novo with a genotype 1b subgenomic HCV replicon (Bart 79I) are treated in duplicates with various concentrations of subject compound and protease inhibitor, either alone or in combination. G418 is included to provide the selective pressure on HCV replicon cells such that cells bearing wild type replicons are expected to die while cells bearing resistant replicons are expected to grow and form visible colonies after about 3 weeks of treatment. Plates are stained with crystal violet and the number of colonies is used to calculate the frequency of resistance (number of colonies/number of input cells). It is expected that the higher the inhibitor concentration, the lower the resistance frequency. It is further expected that compounds which in combination with a protease inhibitor provide a delay and/or decrease the emergence of viral resistance, will exhibit a lower resistance frequency when tested in combination with a protease inhibitor.

Experiment 12

Assaying for Cross-Resistance Between Compounds of the Present Invention and Protease Inhibitors Established HCV replicon-harboring cells are passaged in the presence of either one or more compounds of the present invention or protease inhibitor in 5 replicates yielding colonies that are able to grow in the presence of 2-5× the EC50 of the respective compound. Colonies were pooled, expanded, passaged 15-20 times and the HCV RNA replicating in the cells is subjected to sequence analysis. If protease inhibitor treated pooled clones harbor replicons with mutations that map to the NS4B or the 3' negative terminus, cross-resistance is indicated. If protease inhibitor treated pooled clones do not harbor replicons with mutations that map to the NS4B or the 3' negative terminus, cross resistance is not indicated. Similarly, if pooled clones treated with one or more compounds of the present invention harbor mutations that map to the NS3 coding region, cross resistance is indicated; and, if pooled clones treated with one or more compounds of the present invention do not harbor mutations that map to the NS3 coding region, cross resistance is not indicated.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A method of treating a subject infected with a virus from the Flaviviridae family, the method comprising administering to said subject an indazole compound, or a pharmaceutically acceptable salt, in an amount that is effective in reducing viral load of said virus in said subject, wherein the indazole compound is a compound of Formula II-a, or a pharmaceutically acceptable salt:

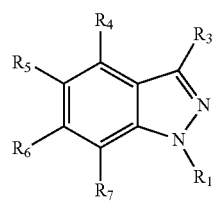

Formula II-a wherein $R_1$ is selected from the group consisting of: —H and

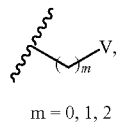

$m = 0, 1, 2$ wherein V is selected from the group consisting of alkyl, cycloalkyl, heterocyclo, aryl, and heteroaryl, wherein V is optionally substituted or unsubstituted;

$R_3$ is selected from the group consisting of —H, —OH, —O(CH$_2$)$_n$X, or —(CH$_2$)$_n$X, wherein n is 1, 2, 3, or 4, and X is selected from the group consisting of —NH$_2$, —NH(alkyl), —N(alkyl)$_2$, —OH, —O-alkyl, —O-aryl, —SO$_2$(alkyl), —SO$_2$NH$_2$, —SO$_2$NH(alkyl), NHSO$_2$(alkyl), heteroaryl, N-attached heterocyclo, and C-attached heterocyclo;

each of $R_4$-$R_7$ is independently selected from the group consisting of: —H, —Br, —Cl, —F, —I, —CH$_3$, —CN, —OH, —OCH$_3$, —NO$_2$, —NH$_2$, —NHCO(alkyl), —NHCO(aryl),

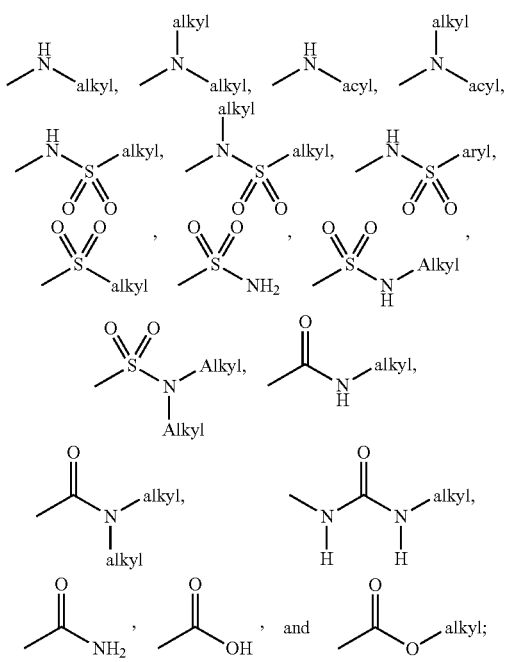

or optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system.

2. The method of claim 1, further comprising administering a therapeutic agent including an NS5A inhibitor.

3. The method of claim 1, further comprising a therapeutic agent including an NS3 helicase inhibitor.

4. The method of claim 1, wherein the virus of the Flaviviridae family is selected from the group consisting of: a flavivirus; a pestivirus; a Hepatitis C virus; a yellow fever virus; a Dengue virus; a Japanese Encephalitis virus; a Murray Valley Encephalitis virus; a St. Louis Encephalitis virus; a West Nile virus; a tick-borne encephalitis virus; a Kunjin virus; a Central European encephalitis virus; a Russian spring-summer encephalitis virus; a Powassan virus; a Kyasanur Forest disease virus; and a Omsk hemorrhagic fever virus.

5. The method of claim 1, wherein the virus of the Flaviviridae family is a Hepatitis C virus.

6. The method of claim 5, wherein the Hepatitis C virus is of a genotype selected from the group consisting of genotype 1, genotype 2, genotype 3, genotype 4, genotype 5, and genotype 6.

7. A method of treating a subject infected with a virus from the Flaviviridae family, the method comprising administering to said subject a compound having the structure:

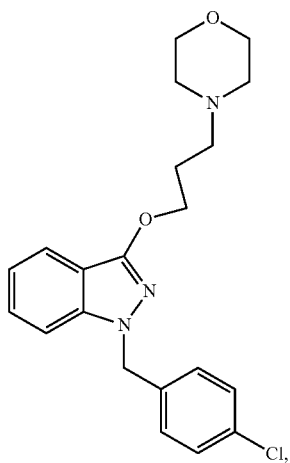 [SMILES: Clc1ccc(Cn2nc(OCCCN3CCOCC3)c3ccccc32)cc1]

or a pharmaceutically acceptable salt, in an amount that is effective in reducing viral load of said virus in said subject.

8. The method of claim 7, further comprising administering one or more additional therapeutic agents selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

9. The method of claim 1, further comprising administering a therapeutic agent including an HCV NS3 protease inhibitor.

10. The method of claim 1, further comprising administering a therapeutic agent selected from the group consisting of: an HCV NS5B RNA-dependent RNA polymerase inhibitor and a nucleoside analog.

11. The method of claim 1, further comprising administering a therapeutic agent selected from the group consisting of: a thiazolide and a sustained release thiazolide.

12. The method of claim 1, further comprising administering a therapeutic agent selected from the group consisting of: an interferon-alpha and a pegylated interferon.

13. The method of claim 1, further comprising administering a therapeutic agent selected from the group consisting of: ribavirin, levovirin, and viramidine.

14. The method of claim 1, further comprising administering is therapeutic agent including a TLR7 agonist.

15. The method of claim 1, further comprising administering a therapeutic agent including a TLR9 agonist.

16. The method of claim 1, further comprising administering a therapeutic agent including a cyclophilin inhibitor.

17. The method of claim 1, further comprising administering a therapeutic agent including an alpha-glucosidase inhibitor.

* * * * *